United States Patent
Hoffman et al.

(10) Patent No.: US 9,732,353 B2
(45) Date of Patent: Aug. 15, 2017

(54) STACKED HERBICIDE TOLERANCE EVENT 8264.42.32.1, RELATED TRANSGENIC SOYBEAN LINES, AND DETECTION THEREOF

(75) Inventors: Thomas Hoffman, Zionsville, IN (US); Ning Zhou, Zionsville, IN (US); Dayakar Pareddy, Carmel, IN (US); Yunxing Cory Cui, Carmel, IN (US); Dawn Marie Parkhurst, Avon, IN (US); Nathan Bard, Madison, WI (US); Sandra Grace Toledo, West Lafayette, IN (US); Gregory Alan Bradfisch, Carmel, IN (US); Bruce Held, Ames, IA (US); Vaithilingam Sekar, Ames, IA (US); Lauren Clark, Whitetown, IN (US); Sean Michael Russell, Carmel, IN (US); Kelly Ann Smith, Lebanon, IN (US); Yang Wang, Johnston, IA (US); Terry R. Wright, Carmel, IN (US)

(73) Assignees: Dow AgroSciences LLC, Indianapolis, IN (US); M.S. Technologies, L.L.C., Adel, IA (US)

( * ) Notice: Subject to any disclaimer, the term of this patent is extended or adjusted under 35 U.S.C. 154(b) by 589 days.

(21) Appl. No.: 13/548,720

(22) Filed: Jul. 13, 2012

(65) Prior Publication Data
US 2013/0055453 A1    Feb. 28, 2013

Related U.S. Application Data

(60) Provisional application No. 61/507,444, filed on Jul. 13, 2011, provisional application No. 61/515,634, filed on Aug. 5, 2011.

(51) Int. Cl.
C12N 15/82 (2006.01)
A01H 5/10 (2006.01)

(52) U.S. Cl.
CPC .......... *C12N 15/8274* (2013.01); *A01H 5/10* (2013.01); *C12N 15/8275* (2013.01);
(Continued)

(58) Field of Classification Search
CPC .. C12N 5/10; C12N 15/8274; C12N 15/8275; C12N 15/8277; A01H 5/00
See application file for complete search history.

(56) References Cited

U.S. PATENT DOCUMENTS 7,626,077 B2  12/2009  Held et al.
7,695,914 B2  4/2010  Bing et al.
(Continued)

FOREIGN PATENT DOCUMENTS

CN   1561167 A   1/2005
CN   1561168     1/2005
(Continued)

OTHER PUBLICATIONS

GenBank nucleotide sequence GQ497217.1.*
(Continued)

*Primary Examiner* — Amjad Abraham
*Assistant Examiner* — Weihua Fan
(74) *Attorney, Agent, or Firm* — James Daly, IV; Barnes & Thornburg LLP

(57) ABSTRACT

This invention relates to soybean event pDAB8264.42.32.1 and includes novel expression cassettes and transgenic inserts comprising multiple traits conferring resistance to glyphosate, aryloxyalkanoate, and glufosinate herbicides. This invention also relates in part to methods of controlling resistant weeds, plant breeding and herbicide tolerant plants. In some embodiments, the event sequence can be "stacked"

(Continued)

with other traits, including, for example, other herbicide tolerance gene(s) and/or insect-inhibitory proteins. This invention further relates in part to endpoint TAQMAN PCR assays for the detection of Event pDAB8264.42.32.1 in soybeans and related plant material. Some embodiments can perform high throughput zygosity analysis of plant material and other embodiments can be used to uniquely identify the zygosity of and breed soybean lines comprising the event of the subject invention. Kits and conditions useful in conducting these assays are also provided.

25 Claims, 4 Drawing Sheets

(52) U.S. Cl.
CPC ... *C12N 15/8277* (2013.01); *C12Y 114/11017* (2013.01); *C12Y 203/01183* (2013.01); *C12Y 205/01019* (2013.01)

(56) References Cited

U.S. PATENT DOCUMENTS

| | | | |
|---|---|---|---|
| 7,696,341 | B2 | 4/2010 | Bing et al. |
| 7,723,575 | B2 | 5/2010 | Alibhai et al. |
| 7,750,207 | B2 | 7/2010 | Wu et al. |
| 7,786,353 | B2 | 8/2010 | Fernandes |
| 7,807,791 | B2 | 10/2010 | Sekar et al. |
| 7,834,146 | B2 | 11/2010 | Kovalic et al. |
| 7,883,850 | B2 | 2/2011 | Song et al. |
| 8,916,752 | B2 | 12/2014 | Wright et al. |
| 2002/0013958 | A1 | 1/2002 | Lalgudi et al. |
| 2003/0157239 | A1 | 8/2003 | Oliveira et al. |
| 2004/0031072 | A1 | 2/2004 | La Rosa et al. |
| 2005/0216969 | A1 | 9/2005 | Song et al. |
| 2006/0282915 | A1 | 12/2006 | Malven et al. |
| 2007/0083945 | A1 | 4/2007 | Byrum et al. |
| 2007/0143873 | A1 | 6/2007 | Pratelli et al. |
| 2007/0143876 | A1 | 6/2007 | Song et al. |
| 2008/0051288 | A1 | 2/2008 | Cressman et al. |
| 2009/0093366 | A1 | 4/2009 | Wright et al. |
| 2009/0104700 | A1 | 4/2009 | Samuel et al. |
| 2010/0197503 | A1* | 8/2010 | Hawkes et al. ............... 504/348 |
| 2010/0251432 | A1 | 9/2010 | Lira et al. |
| 2013/0055453 | A1 | 2/2013 | Hoffman et al. |
| 2015/0080218 | A1 | 3/2015 | Wright et al. |

FOREIGN PATENT DOCUMENTS

| | | | |
|---|---|---|---|
| CN | 101 020 905 | | 8/2007 |
| CN | 101020905 | | 8/2007 |
| CN | 101297040 | | 10/2008 |
| EP | 2309843 | | 4/2011 |
| JP | 2004-27091 A | | 6/2002 |
| JP | 2008-295322 A | | 12/2008 |
| UA | A200714839 | | 4/2008 |
| WO | WO 2004/011601 | | 2/2004 |
| WO | WO 2004/074443 | | 9/2004 |
| WO | WO 2006/045633 | | 5/2006 |
| WO | WO2006108675 | | 10/2006 |
| WO | WO 2006130436 | | 12/2006 |
| WO | WO2007053482 | * | 5/2007 ............... A01H 5/00 |
| WO | WO 2007053482 | | 5/2007 |
| WO | WO2008/141154 | | 11/2008 |
| WO | WO 2009/037329 | | 3/2009 |
| WO | PCT/US2009/47080 | * | 12/2009 ............... A01H 5/00 |
| WO | WO 2009/152359 | | 12/2009 |
| WO | WO 2010/002984 | | 1/2010 |
| WO | WO 2010/008760 | | 1/2010 |
| WO | WO 2010/015627 | | 2/2010 |
| WO | WO 2010/079032 | | 7/2010 |
| WO | PCT/US10/57886 | * | 5/2011 ............... A01H 5/00 |
| WO | WO2011063413 | * | 5/2011 ............... A01H 5/00 |
| WO | WO 2011/066382 A | | 6/2011 |
| WO | WO2011066360 A1 | | 6/2011 |
| WO | WO2011066384 A1 | | 6/2011 |
| WO | WO2012075426 A1 | | 6/2012 |

OTHER PUBLICATIONS

Schmutz, Jeremy, et al. "Genome sequence of the palaeopolyploid soybean." nature 463.7278 (2010): 178-183.*
Zhong, Gan-Yuan. "Genetic issues and pitfalls in transgenic plant breeding." Euphytica 118.2 (2001): 137-144.*
Schmutz, J., et al. "Genome sequence of the palaeopolyploid soybean." nature 463(7278): 178-183.*
Ron Brunoehler, Going public cuts soybean seed costs, Corn and Soybean digest, Feb. 2000.*
Lam, Hon-Ming, et al. "Resequencing of 31 wild and cultivated soybean genomes identifies patterns of genetic diversity and selection." Nature genetics 42.12 (2010): 1053-1059.*
Heck, G. R., et al. Crop Science 45.1 (2005): 329-339.*
Zeng et al, Plant Cell Rep (2004) 22:478-482.*
XP-002732015, AAD-12, 2mepsps, pat, Glycine max (L) Merr. (DAS44406 OECD UI DAS-44406-6 AFFRC Feb. 7, 2011.
EMBL Accession No. HN002532, GSS_Ba205J12.R GSS_Ba Glycine soja genomic 3', genomic survey sequence, May 9, 2010.
XP-002732015, AAD-12, 2mepsps, pat. Glycine max (L.) Merr. (DAS44406 OECD UI DAS-44406-6 AFFRC Feb. 7, 2011.
Lam, Hon-Ming, et al. "Resequencing of 31 wild and cultivated soybean genomes identifies patterns of genetic diversity and selection," 2010, Nature genetics 42,1053-1059.
Schmutz, J., et al. "Genome sequence of the palaeopolyploid soybean," 2010, Nature, 463, 178-183.
Zhong, Gan-Yuan, "Genetic issues and pitfalls in transgenic plant breeding," 2001, Euphytica 118, 137-144.
Database Geneseq [Online] Jul. 24, 2008 (Jul. 24, 2008), "B. napas PCR primer RflRV."
GenBank accession: HQ403648—Eleusine indica 5-enolpyruvylshikimate-3-phosphate synthase (epsps-R) mRNA, complete cds; plastid—May 27, 2011.
GenBank accession: HQ403647—Eleusine indica 5-enolpyruvylshikimate-3-phosphate synthase (EPSPS-S) mRNA, complete cds; plasmid—May 27, 2011.
GenBank accession: GU256772—Mutant Zoysia japonica 5-enolpyruvyl shikimate 3-phosphate synthase (EPSPS) mRNA, complete cds—Jan. 27, 2010.
GenBank accession: GU256771—Zoysia japonica 5-enolpyruvyl shikimate 3-phosphate synthase (EPSPS) mRNA, complete cds.—Jan. 27, 2010.
http://www.bch.biodic.go.jp/download/en_lmo/H23_9_6_DAS44406.pdf—aad-12, 2mepsps, pat, Glycine max (L.) Merr. (OAS44406 OECU UI: OAS-44406-6)—Feb. 7, 2011.
GenBank accession: XM_002436379—Sorghum bicolor hypothetical protein, mRNA—Jul. 13, 2009.
GenBank accession: GX744067—Sequence 12246 from U.S. Pat. No. 7,834,146—Dec. 13, 2010.
GenBank accession: GX619320—Sequence 5 from U.S. Pat. No. 7,807,791—Dec. 13, 2010.
GenBank accession: GX315220—Sequence 9295 from U.S. Pat. No. 7,750,207—Dec. 12, 2010.
GenBank accession: GX270866—Sequence 47 from U.S. Pat. No. 7,723,575—Aug. 13, 2010.
GenBank accession: GY007493—Sequence 3 from U.S. Pat. No. 7,883,850—Apr. 30, 2011.
GenBank accession: JA216562—Sequence 39 from patent EP2309843—Apr. 26, 2011.
GenBank accession: FW377938—Transgenic plant event detection—Sep. 30, 2010.
GenBank accession: GX006377—Sequence 27 from U.S. Pat. No. 7,696,341—Aug. 13, 2010.
GenBank accession: GX006374—Sequence 24 from U.S. Pat. No. 7,696,341—Aug. 13, 2010.
GenBank accession: GX003492—Sequence 27 from U.S. Pat. No. 7,695,914—Aug. 13, 2010.

(56) References Cited

OTHER PUBLICATIONS

GenBank accession: GX003489—Sequence 24 from U.S. Pat. No. 7,695,914—Aug. 13, 2010.
GenBank accession: HD115809—Sequence 29 from Patent WO2010079032—Aug. 11, 2010.
GenBank accession: GQ497217—Glycine max transgenic GMO cassette genomic sequence—Sep. 28, 2009.
GenBank accession: FJ410919—Binary vector pWY109, complete sequence—Jan. 12, 2009.
GenBank accession: EU554319—Yeast selection vector pIS421, complete sequence—Sep. 23, 2008.
GenBank accession: DQ156557—Zea mays transgenic phosphinothricin acetyltransferase gene, partial cds; and beta lactamase and phosphinothricin acetyltransferase genes, complete cds—Mar. 1, 2006.
GenBank accession: AC217803—Canis familiaris chromosome 21, clone WORK_REGION, complete sequence—Feb. 28, 2008.
GenBank accession: AC187003—Canis Familiaris chromosome 21, clone XX-427H12, complete sequence—Jul. 29, 2006.
GenBank accession: AK157167—Mus musculus activated spleen cDNA, Riken full-length enriched library, clone: F830205P13 product: unclassifiable, full insert sequence—Oct. 16, 2010.
GenBank accession: AK081799—Mus musculus 16 days embryo head cDNA, Riken full-length enriched library, clone: C130078E19 product: unclassifiable, full insert sequence—Oct. 6, 2010.
GenBank accession: AB073156—Arabidopsis thaliana DNA, chromosome 4 centromere region, BAC clone: F13F19—Feb. 14, 2004.
GenBank accession: BT090294—Soybean clone JCVI-FLGm-4121 unknown mRNA—Aug. 6, 2009.
GenBank. Accesion AY395700—Eleusine indica 5-enolpyruvylshikimate-3-phosphate synthase (EPSPS-S) mRNA, partial cds—Oct. 29, 2006.
GenBank. Accesion AJ417034—Eleusine indica platid partial mRNA for 5-enolpyruvylshikimate-3-phosphate synthase (EPSPS-S gene)—Apr. 15, 2005.
GenBank. Accesion X63374—Z.mays mRNA for EPSP-synthase—May 18, 2005.
GenBank. Accesion AY106729—Zea mays PCO094563 mRNA sequence—Jun. 2, 2008.
GenBank. Accesion CQ868456—Sequence 3 from Patent WO2004074443—Sep. 13, 2004.
GenBank. Accession GP765237—Sequence 5 from U.S. Pat. No. 7,626,077—Dec. 14, 2009.
GenBank. Accession D1012786—Chimera gene with several herbicide resistant genes, plant cell and plant resistant to several herbicides—Feb. 21, 2008.
GenBank. Accession CS434496—Sequence 14 from Patent WO2006045633—Oct. 24, 2006.
GenBank. Accession EU090199—Brassica napus transgenic line Rf1 right border junction sequence of transgenic event genomic sequence—Nov. 7, 2007.
GenBank. Accession GU574780—MISSA recipient vector BIBAC-LTR, complete sequence—May 6, 2010.
GenBank. Accession GN123171—Sequence 6067 from Patent WO2009037329—Apr. 24, 2009.
GenBank. Accession GN123168—Sequence 6064 from Patent WO2009037329—Apr. 24, 2009.
GenBank. Accession GN123173—Sequence 6069 from Patent WO2009037329—Apr. 24, 2009.
GenBank. Accession XM_002980455—Selaginella moellendorffii hypothetical protein, mRNA—Aug. 13, 2010.
Database Geneseq [Online] Jul. 9, 2009 (Jul. 9, 2007), <<Soybean nucleic acid Seq ID No. 133298, retrieved from EBI accession No. GSN:ARD51602 Database accession No. ARD51602.
ARD51602, Database GeneSeq[online], Apr. 12, 2007/.
A59344, Database DDBJ[online], Mar. 6, 1998, A59344.1, http://getentry.ddbj.nig.ac.jp/getentry/na/A59344/?filetype=html.
A02774, Database DDBJ[online], Mar. 25, 1993, A02774.1, http://getentrv.ddbj.nig.ac.jp/getentrv/na/A02774/?filetype=html.
AAN50226, Database GeneSeq[online], Oct. 24, 2003.
AB027254, Database DDBJfonline], Jan. 24, 2004.
BC100043, Database DDBJ[online], Aug. 15, 2005.
ARU42167, Database GeneSeqlonline], Aug. 21, 2008.
AQY41271, Database GeneSeq[online], Jul. 10, 2008.
Pakula, AA et al., "Genetic analysis of protein stability and function," 1989, Anna. Rev. Genet, 23, pp. 289-310. (abstract only).
Fraenkel, AE. et al., "Characterization of diphtheria fusion proteins targeted to the human interleukin-3 receptor," 2000, Protein Eng., vol. 13, No. 8, 575-581.
Database NCBI Reference Sequence: XM_002582376.1 from Sep. 16, 2009.
Database NCBI Reference Sequence: XM:_002980455.1 from Aug. 13, 2010 (see sequence).
https://www.jpo.go.jp/shiryou/s_sonata/hyoujun_gijutsu/kakusan/001.html.
Shaner, D. L. "Role of translocation as a mechanism of resistance to glyphosate." Weed Science 57.1 (2009): 118-123.
GenBank; AK286292.1. Glycine max cDNA, clone: GMFL01-25-J19 [online] Nov. 19, 2008 [retrieved on Mar. 14, 2012]. Available on the internet: <URL:http:www.ncbi.nlm.nih.gov/nuccore/AK286292.1>.
GenBank EU721743.1. Glycine max clone BAC 71B1. [online] Dec. 5, 2008 [retrieved Mar. 14, 2012]. Available on the internet: <URL:http://www.ncbi.nlm.nih.gov/nuccore/EU721743>.
Database Geneseq [Online] Jul. 9, 2009 (Jul. 9, 2009), "Soybean nucleic acid Seq ID No. 133298.", XP002721468, retrieved from EBI accession No. GSN:ARD51602.
Database Geneseq [Online] Jul. 9, 2009 (Jul. 9, 2009), "Soybean nucleic acid Seq ID No. 33302.", XP002721469, retrieved from EBI accession No. GSN:ARC51605.
Database EMBL [Online] Oct. 28, 2006 (Oct. 28, 2006), "GM_WBa0024I05.r GM_WBa Glycine max genomic clone GM_WBa0024I05 3', genomic survey sequence.", XP002721470, retrieved from EBI accession No. EM_GSS:ED626487.
Database EMBL [Online] May 9, 2010 (May 9, 2010), "GSS_Ba098E14. R GSS_Ba Glycine soja genomic 3', genomic survey sequence.", XP002721471, retrieved from EBI accession No. EM_GSS:HN019107.
Database EMBL [Online] Nov. 1, 2008 (Nov. 1, 2008), "Glycine max clone BAC 71B1, * Sequencing in Progress*, 3 unordered pieces.", XP002721472, retrieved from EBI accession No. EM HTG:EU721743.
Database EMBL [Online] Nov. 18, 2004 (Nov. 18, 2004), "Com seedling-derived polynucleotide (cpds), Seq ID 5567.", XP002721473, retrieved from EBI accession No. GSN:ADS70551.
Database Geneseq [Online] Aug. 23, 2007 (Aug. 23, 2007), "Cry1F event 281-24-236 transgene, Seq ID 1.", XP002721474, retrieved from EBI accession No. GSN:AGD74685.
Database Geneseq [Online] Jul. 24, 2008 (Jul. 24, 2008), "B. napas PCR primer Rf1RV.", XP002721475, retrieved from EBI accession No. GSN:ARW87360.
Database Geneseq [Online] Apr. 1, 2010 (Apr. 1, 2010), "miRNA targeted gene sequence Seq ID No. 237.", XP002721475, retrieved from EBI accession No. GSN:AXU86864.
GenBank accession: AM182233—Zea mays transgenic insert TC-1507, 5' region—Jan. 8, 2007.
Japanese Agriculture, Forestry and Fisheries Research Council (AFFRC), 'Herbicide allyloxymethyl alkanoate system and glyphosate and glufosinate-resistance (modified aad-12, 2mepsps, pat, Glycine max (L.) Merr.) (DAS44406, OECD UI : DAS-44400-6)', Application by Dow Chemical Japan Co., Ltd for first use approval of genetically modified organisms according to the provisions of the Act for Securing Biodiversity, Feb. 7, 2011, [retrieved from internet on Jun. 8, 2016] <URL: http://www.s.affrc.go.jp/docs/commitee/diversity/110415/pdf/siryo_2-2.pdf>.
"Glycine max chromosome 15, whole genome shotgun sequence" [Jan. 11, 2010, online] retrieved from GenBank [retrieved on Jun. 23, 2016], accession No. CM000848 http://www.ncbi.nlm.nih.gov/nuccore/283570559?sat=16&satkey=5691280.
GenBank accession: AK286292—Glycine max cDNA, clone: GMFLO1-25419—Nov. 19, 2008.

(56) References Cited

OTHER PUBLICATIONS

XP-002732015, Soybean tolerant to aryloxyalkanoate herbicide, glyphosate herbicide, and glufosinate herbicide (Modified aad-12, 2mepsps, pat, Glycine max (L.) Merr.) (DAS44406, ECD UI: DAS-444Ø6-6)—Feb. 7, 2011.
https://www.env.go.jp/press/files/jp/17785.pdf.

* cited by examiner ual and related patent references.

SEQUENCE LISTING

```
<160> NUMBER OF SEQ ID NOS: 21

<210> SEQ ID NO 1
<211> LENGTH: 1246
<212> TYPE: DNA
<213> ORGANISM: Artificial
<220> FEATURE:
<223> OTHER INFORMATION: 5' border

<400> SEQUENCE: 1
```

```
agcttatggt tttgtttcaa tacaaggaga caataaatta gtttagaata ttatttttga    60
aacctatatt attacaatta tatggacata ttagacacat gacaagtata atttgttttt   120 ttttttacctc tctaatatat cctcatttgt taccatttct ccacacagtt taagttgaga   180
attaattttc aatattgcaa agttatactt atgatttgaa atcttgtaa acacaaatga    240 atccgatttt ttttttttt taaagggaaa gcaaatgaat ctgattatgt atgtatgtgt    300
ttttttcttt ctctgcgtaa tcatatatct cttttaaaca cttcaaaaca agatttagaa   360
ttttcattgt aagatattca atcttcaacg cttctttaag gaggtgacat ttttttttatt  420 actttaggct tatttttatt agatatttgg ttcatttctt taatagtacc accaagacca   480
tttgcattta atgaatact agcatctaag attcaaaata aataattctt tccaacgaca    540
tcaattaaga gcataaattt gagttcaaca aaatttgaca ttccgtatta tcataagata   600
atacaagtta tacaacatcc acaaagaata aaggtgtatc atttaaatga cagctaacat   660
caaacaaaga tgtctgtaaa aaaaaacatc aagcaaagat gaagaatttt ttttttttct   720
tctgtgtgtg tgataagcaa caaagaaaat cccacatgct tggacaggaa agaggaaaa   780 aaacttcata aatatgtaaa tgcttcacaa catgagtcat gctaatatta attatgttat    840
aagaaaaatt caaataaaag aaaaagtata gagtagaaaa aaaggtgtat agaaaaaaga   900
tagagaagag gtgtgtttaa tttctttctt tcttttttata tgtgtttaac ttcttttaac  960
ataataaata tttatacata taataagtag aagtagaaga caattagaga aaacttagaa   1020
agtcatatta tatacatttt tataatatt tcttagaaac acattcttat tcttattgtt     1080
aaaagaaact aatcatatta tatccttacc agcaggagaa gtcaattcaa atttaacaaa   1140
aggatgaata tttataaaat aataattttt tttgacataa tttataacaa aaaataattt    1200 tttttttgt aactagaggt ttctatccta attttttatt ctctga                   1246

<210> SEQ ID NO 2
<211> LENGTH: 504
<212> TYPE: DNA
<213> ORGANISM: Artificial
<220> FEATURE:
<223> OTHER INFORMATION: 3' border

<400> SEQUENCE: 2
tacacatgta tgaccccttg atttattaat tttaaaaaat gtgcatgcca attaccaaca    60
ataccaatag gatcccaatt aaaccgatag agaaagcgag gtaatcatac acccgttttc   120
ggctacatgg gggtggtgag gcgatgctat tctcacatgc catttttcgtt cctactacga  180 ccgctccaac catcatctcg aattccattg tcggtggaga aacccaaggc ccgcattgga   240
cagtgacgac agtgagggta acgctatcag aatgcgtgcg catcaagcag ccaaaacgac   300
ggcgttggca tttacgaagt ggcgttttgg ttgtatccga agcggcagag gggcgtttag   360
gtaaattcgg gaagcgaaaa gcaatgagaa atagcgaaac gcttcgtatc tcttcactac   420
tactactact actacacttg gtttctggta gtagtgtttt ttgttacgca cacaccaaaa   480
cggctctctc gcagcccaaa agct                                          504

<210> SEQ ID NO 3
<211> LENGTH: 25
<212> TYPE: DNA
<213> ORGANISM: Artificial
<220> FEATURE:
<223> OTHER INFORMATION: Primer 4232-WF1

<400> SEQUENCE: 3
```
gatttctgca tcatttatga ccagg 25

<210> SEQ ID NO 4
<211> LENGTH: 25
<212> TYPE: DNA
<213> ORGANISM: Artificial
<220> FEATURE:
<223> OTHER INFORMATION: Primer 4232-WF3

<400> SEQUENCE: 4
tgtaaatgct tcacaacatg agtca 25

<210> SEQ ID NO 5
<211> LENGTH: 25
<212> TYPE: DNA
<213> ORGANISM: Artificial
<220> FEATURE:
<223> OTHER INFORMATION: Primer 4232-WF4

<400> SEQUENCE: 5
atgtaaatgc ttcacaacat gagtc 25

<210> SEQ ID NO 6
<211> LENGTH: 26
<212> TYPE: DNA
<213> ORGANISM: Artificial
<220> FEATURE:
<223> OTHER INFORMATION: Primer 4232-WR1

<400> SEQUENCE: 6
tttctacagc tagcacaaca agacct 26

<210> SEQ ID NO 7
<211> LENGTH: 28
<212> TYPE: DNA
<213> ORGANISM: Artificial
<220> FEATURE:
<223> OTHER INFORMATION: Primer 4232-WR2

<400> SEQUENCE: 7
cgtatctgat actaaccagt tcgaattc 28

<210> SEQ ID NO 8
<211> LENGTH: 25
<212> TYPE: DNA
<213> ORGANISM: Artificial
<220> FEATURE:
<223> OTHER INFORMATION: Primer 4232-WR3

<400> SEQUENCE: 8
aagagatacg aagcgtttcg ctatt 25

<210> SEQ ID NO 9
<211> LENGTH: 26
<212> TYPE: DNA
<213> ORGANISM: Artificial
<220> FEATURE:
<223> OTHER INFORMATION: Primer 4232-WR4

<400> SEQUENCE: 9
aaacactact accagaaacc aagtgt 26

<210> SEQ ID NO 10
<211> LENGTH: 26
<212> TYPE: DNA

```
<213> ORGANISM: Artificial
<220> FEATURE:
<223> OTHER INFORMATION: Primer ED_v1_C1

<400> SEQUENCE: 10
gagtaaagga gaccgagagg atggtt                                          26

<210> SEQ ID NO 11
<211> LENGTH: 24
<212> TYPE: DNA
<213> ORGANISM: Artificial
<220> FEATURE:
<223> OTHER INFORMATION: Primer PAT_11

<400> SEQUENCE: 11
acagagccac aaacaccaca agag                                            24

<210> SEQ ID NO 12
<211> LENGTH: 27
<212> TYPE: DNA
<213> ORGANISM: Artificial
<220> FEATURE:
<223> OTHER INFORMATION: Primer 4232_3'F

<400> SEQUENCE: 12
cgcaatgtgt tattaagttg tctaagc                                         27

<210> SEQ ID NO 13
<211> LENGTH: 26
<212> TYPE: DNA
<213> ORGANISM: Artificial
<220> FEATURE:
<223> OTHER INFORMATION: Primer 4232_3'R

<400> SEQUENCE: 13
ctctatcggt ttaattggga tcctat                                          26

<210> SEQ ID NO 14
<211> LENGTH: 18
<212> TYPE: DNA
<213> ORGANISM: Artificial
<220> FEATURE:
<223> OTHER INFORMATION: Primer 4232_3'P labeled with FAM and MGB

<400> SEQUENCE: 14
atgccaatta ccaacaat                                                   18

<210> SEQ ID NO 15
<211> LENGTH: 24
<212> TYPE: DNA
<213> ORGANISM: Artificial
<220> FEATURE:
<223> OTHER INFORMATION: Primer GMS116 F

<400> SEQUENCE: 15
gtaatatggg ctcagaggaa tggt                                            24

<210> SEQ ID NO 16
<211> LENGTH: 23
<212> TYPE: DNA
<213> ORGANISM: Artificial
<220> FEATURE:
<223> OTHER INFORMATION: Primer GMS116 R

<400> SEQUENCE: 16
atggagaaga acattggaat tgc                                             23
```

```
<210> SEQ ID NO 17
<211> LENGTH: 23
<212> TYPE: DNA
<213> ORGANISM: Artificial
<220> FEATURE:
<223> OTHER INFORMATION: Probe GMS116 labeled with HEX and BHQ1

<400> SEQUENCE: 17
ccatggcccg gtaccatctg gtc                                             23

<210> SEQ ID NO 18
<211> LENGTH: 12011
<212> TYPE: DNA
<213> ORGANISM: Artificial
<220> FEATURE:
<223> OTHER INFORMATION: pDAB8264 T-strand insert and partial flanking
      sequences

<400> SEQUENCE: 18
agcttatggt tttgtttcaa tacaaggaga caataaatta gtttagaata ttatttttga      60
aacctatatt attacaatta tatggacata ttagacacat gacaagtata atttgttttt    120
tttttacctc tctaatatat cctcatttgt taccatttct ccacacagtt taagttgaga    180
attaattttc aatattgcaa agttatactt atgatttgaa atcttgtaa acacaaatga     240 atccgatttt ttttttttt taaagggaaa gcaaatgaat ctgattatgt atgtatgtgt     300
tttttctttt ctctgcgtaa tcatatatct cttttaaaca cttcaaaaca agatttagaa    360
ttttcattgt aagatattca atcttcaacg cttcttaaag gaggtgacat ttttttttatt   420 actttaggct tatttttatt agatatttgg ttcatttctt taatagtacc accaagacca    480
tttgcattta aatgaatact agcatctaag attcaaaata ataattctt tccaacgaca     540 tcaattaaga gcataaattt gagttcaaca aaatttgaca ttccgtatta tcataagata    600
atacaagtta tacaacatcc acaaagaata aggtgtatc atttaaatga cagctaacat     660
caaacaaaga tgtctgtaaa aaaaaacatc aagcaaagat gaagaatttt ttttttttct    720
tctgtgtgtg tgataagcaa caaagaaaat cccacatgct tggacaggaa agaggaaaa     780 aaacttcata aatatgtaaa tgcttcacaa catgagtcat gctaatatta attatgttat    840
aagaaaaatt caaataaaag aaaaagtata gagtagaaag aaaggtgtat agaaaaaga     900 tagagaagag gtgtgtttaa tttctttctt tcttttttata tgtgtttaac ttcttttaac   960
ataataaata tttatacata taataagtag aagtagaaga caattagaga aaacttagaa    1020
agtcatatta tatacatttt tataatatttt tcttagaaac acattcttat tcttattgtt   1080
aaaagaaact aatcatatta tatccttacc agcaggagaa gtcaattcaa atttaacaaa    1140
aggatgaata tttataaaat aataattttt tttgacataa tttataacaa aaaataattt    1200
ttttttttgt aactagaggt ttctatccta atttttttatt ctctgaccag tcagcatcat   1260
cacaccaaaa gttaggcccg aatagtttga aattagaaag ctcgcaattg aggtctacag    1320
gccaaattcg ctcttagccg tacaatatta ctcaccggat cctaaccggt gtgatcatgg    1380
gccgcgatta aaaatctcaa ttatatttgg tctaatttag tttggtattg agtaaaacaa    1440
attcgaacca aaccaaaata taaatatata gttttatat atatgccttt aagactttt     1500 atagaatttt ctttaaaaaa tatctagaaa tatttgcgac tcttctggca tgtaatattt    1560
cgttaaatat gaagtgctcc attttttatta acttaaata attggttgta cgatcacttt    1620
cttatcaagt gttactaaaa tgcgtcaatc tctttgttct tccatattca tatgtcaaaa    1680
```

```
cctatcaaaa ttcttatata tcttttttcga atttgaagtg aaatttcgat aatttaaaat    1740
taaatagaac atatcattat ttaggtatca tattgatttt tatacttaat tactaaattt    1800
ggttaacttt gaaagtgtac atcaacgaaa aattagtcaa acgactaaaa taaataaata    1860
tcatgtgtta ttaagaaaat tctcctataa gaatatttta atagatcata tgtttgtaaa    1920
aaaaattaat ttttactaac acatatattt acttatcaaa aatttgacaa agtaagatta    1980
aaataatatt catctaacaa aaaaaaaacc agaaaatgct gaaaacccgg caaaaccgaa    2040
ccaatccaaa ccgatatagt tggtttggtt tgattttgat ataaaccgaa ccaactcggt    2100
ccatttgcac ccctaatcat aatagcttta atatttcaag atattattaa gttaacgttg    2160
tcaatatcct ggaaattttg caaaatgaat caagcctata tggctgtaat atgaatttaa    2220
aagcagctcg atgtggtggt aatatgtaat ttacttgatt ctaaaaaaat atcccaagta    2280
ttaataattt ctgctaggaa gaaggttagc tacgatttac agcaaagcca gaatacaatg    2340
aaccataaag tgattgaagc tcgaaatata cgaaggaaca atatttttta aaaaaatacg    2400
caatgacttg gaacaaaaga agtgatata tttttttgttc ttaaacaagc atcccctcta    2460
aagaatggca gttttccttt gcatgtaact attatgctcc cttcgttaca aaaattttgg    2520
actactattg ggaacttctt ctgaaaatag tggccaccgc ttaattaagg cgcgccgacg    2580
aatgtccccg atcaaatctg agggacgtta aagcgatgat aaattggaac cagaatatag    2640
aatctttgtt ctgctctagc ttttcttctg tacatttttt acgattagac tatgattttc    2700
attcaataac caaaattctg aagtttgtca tcaagttgct caatcaaact tgtaccggtt    2760
tgtttcggtt ttatatcagc tcactgttac acttttaacca aaatcggttt atgtcttaat    2820
aaaggaattg agtcggttta actcatatcc gtaccaatgc gacgtcgtgt ccgcgtttca    2880
gtagctttgc tcattgtctt ctacgggaac tttcccggac ataggaaccg ccctttcgtt    2940
atcctcatcc atcgtgaaat caggaaataa atgttcgaag atttgaggtc aaaagtcgaa    3000
tttcatgttg tctcttctat ttagatacaa aattgaagca attttcacca atttaatgcc    3060
aaaatttaaa acaacgctga taaagtgaaa cttgattcga tttatatttc aaccgaaact    3120
gctgaagcaa gaagaaaaag cgtaattaca cataacaaga acgctaccgc aaactactaa    3180
acgccaaacc caatcaaaaa gtaaaacgca gacgcttaag tgagaaaccc agaaaacaca    3240
aacgcggatc gggggatcca ctagttctag agcttaattc ttgacgaaag tgctcagcac    3300
atcgaagtag tcggggaagg tcttccgggt gcacccaggg tcccggatgg tgacggggac    3360
ctcggcacag gcggcaaggg agaaagccat cgccatcctg tggtcgtcgt acgtgtcgat    3420
cgccgtcacg ttcagcttct ccggcggcgt gatgatgcag tagtccggcc cttcctcaac    3480
agatgctccc agcttggtta gctccgtccg gatcgcaacc atcctctcgg tctccttttac    3540 tctccaggaa gccacgtctc tgatggctgt cgggccatcg gcaaagaggg caaccacagc    3600
aagagtcatg gcgacatcag gcatcttgtt catgttgaca tcaatcgcct tgaggtgttt    3660
cctcccaaat ggctcccgcg gtgggccagt aacagttacg ctagtctcgg tccatgtaac    3720
cttcgctccc atcatctcca gtacctcagc aaacttcaca tcaccctgca aactggtggt    3780
gccacaacct tccacagtca cagtccctcc agtaattgca gcaccagcca agaaatagct    3840
tgcgcttgag gcatcacctt caacataggc attttaggg gacttgtatt tttgacctcc    3900
cttaatgtag aatctgtccc agctatcaga atgctctgct ttcacaccaa aacgctccat    3960
caatctcaat gtcatttcga cgtacggaat ggagattaat ttatcaatga tttcaatctc    4020
```

| | |
|---|---|
| cacatcccca agagccaaag gagcagccat cagcaaggca ctcaagtact gactgctgat | 4080 |
| ggagccagac agcttgacct tgccaccagg tagccctccg attccattga cacgaacagg | 4140 |
| tgggcagtca gtgccaagga acaatcaac atctgcacca agctgcttca atccgacaac | 4200 |
| caagtcgcca atgggtctct ccctcattct tggtactcca tcaagcacgt aagttgcatt | 4260 |
| tccaccagca gcagtaacag ctgctgtcaa ggaccgcatt gcgattccag cattccccaa | 4320 |
| gaagagctgc acttcctctt tagcatcctc aactgggaac tttccaccac agccaacaac | 4380 |
| tacagctctt ttggcagctt tgtccgcttc gacagagaga ccaagagtcc tcaaggcccc | 4440 |
| gagcatgtag tggacatcct cactgttcag caggttatca accactgttg tccctcgga | 4500 |
| cagggcggcg agtaggagga tccggttgga aagcgacttg gaccccggca gcttgacggt | 4560 |
| gccggagatc tccttgatgg gctgcagcac gatctcctcg gcgccggcca tgcaccggat | 4620 |
| ccttccgccg ttgctgacgt tgccgaggct tctggaggag cggcgggcga cggggaggct | 4680 |
| ggcggtggac ttgagcccct ggaacggagc gacggcggtg ccgacgagg ccatcatcac | 4740 |
| ggtgggcgcc atagacagcg gcggcaggta cgacagcgtc tcgaacttct tgttgccgta | 4800 |
| ggccggccac acctgcatac attgaactct ccaccgttg ctgggaaggg tggagaagtc | 4860 |
| gttagccttc ttggtggtgg ggaaggcggc gttggactta aggccggtga acggagccac | 4920 |
| catgttggcc tgagcagggg cggtccggct aacggtcgcg actgaggagg agatcgaagc | 4980 |
| catggggatc tgcgcattta acaagaaatt gaacagtcaa ttggggattt tcattatcca | 5040 |
| taactaaatt ttgaagaaat tggaatacta acgtcacca cttaaaaccc taatccagat | 5100 |
| gaatcgttat cgaaccagat ataaccaaaa ggggcaaaat tgactcgaaa accctagttc | 5160 |
| tcgatacacg gctaggtaat gacaatcgca cacagacaaa tctggttata cagaacttcg | 5220 |
| aagcaagaaa aaaacgatga agaatggatc atccaataaa tcgactagac tcaatcttca | 5280 |
| caggtttatc gatccagcaa acttaaaaga cggaccttta ttttcaaact ggaatgggac | 5340 |
| aaaacccgaa actctattgt cgtaaaatca gatcgcggag acagtaacag aaaaaacatt | 5400 |
| aaaaagtaat ggaaagacct aaaccccctga tctaattaca aacaaatcat acctgttctt | 5460 |
| cgcctgaggg gttcgaaatc gataagcttg gatcctctag agtcgagaga aattgatgtc | 5520 |
| tgtagaagaa gaagaacggt taagagtaga tttgggtgag aaagatgtga aattgttttt | 5580 |
| ataggcaaag acgagagtc tattttttga gcaatcagat cgcatattaa atctaacggc | 5640 |
| tgagatatcg atccgtgtgt acaataaaat gatgtataaa ccgtcgatct gttttaatcg | 5700 |
| acggttcata ttagtgatcc gcgtgatggc agtgatagcc actaagaatc gtcttttgtt | 5760 |
| ttacatgtgg cgccacaaat tagggtaatg aagcggcaat attttggaac tcggaaaata | 5820 |
| aaattgcgcc atcacattat ttgaaaattt tcacatgctt ttattttaaa acccacgaa | 5880 |
| ttacaagtta caaccgaaaa agatttataa tatagtgatt tatactaatt ttgtagtagc | 5940 |
| ttaatgtata ttgatactgg aaaaacaatg acaatcatat gttagtatta tcaagttatc | 6000 |
| gtattgatat tgatattgga acatacaatg ggtattgcct tctttcgacc ataaatatca | 6060 |
| ccaaatttac aaagtttgtg tataccaagt tatcaattgt aaatgggatg tcaacatttt | 6120 |
| aatttccctt tgagaaacta tagaccacaa gaacacactt caatagataa agtaactatt | 6180 |
| tacataagag gttttaaaat cacattaaca aaaataatta ccaaccggca ctcacaaata | 6240 |
| caaacagagc acacgacatg tcaaagccac aagtaaattc gttgagtggt ggtttcatta | 6300 |
| caattgtgtc acttgcagca caaactatct tgctctggga atcatctcag catcaaagat | 6360 |
| catgctcact tcaggggaac ttagtgtatc catgcctcga ctcatatttc tcctcgacat | 6420 |

```
gcatcctgca ggggcgcgcc atgcccgggc aagcggccgc acaagtttgt acaaaaaagc      6480
aggctccgcg gtgactgact gaaaagcttg tcgacctgca ggtcaacgga tcaggatatt      6540
cttgtttaag atgttgaact ctatggaggt ttgtatgaac tgatgatcta ggaccggata      6600
agttcccttc ttcatagcga acttattcaa agaatgtttt gtgtatcatt cttgttacat      6660
tgttattaat gaaaaaatat tattggtcat tggactgaac acgagtgtta aatatggacc      6720
aggccccaaa taagatccat tgatatatga attaaataac aagaataaat cgagtcacca      6780
aaccacttgc cttttttaac gagacttgtt caccaacttg atacaaaagt cattatccta      6840
tgcaaatcaa taatcataca aaaatatcca ataacactaa aaaattaaaa gaaatggata      6900
atttcacaat atgttatacg ataaagaagt tacttttcca agaaattcac tgattttata      6960
agcccacttg cattagataa atggcaaaaa aaaacaaaaa ggaaaagaaa taagcacga       7020 agaattctag aaaatacgaa atacgcttca atgcagtggg acccacggtt caattattgc      7080
caattttcag ctccaccgta tatttaaaaa ataaaacgat aatgctaaaa aaatataaat      7140
cgtaacgatc gttaaatctc aacggctgga tcttatgacg accgttagaa attgtggttg      7200
tcgacgagtc agtaataaac ggcgtcaaag tggttgcagc cggcacacac gagtcgtgtt      7260
tatcaactca aagcacaaat acttttcctc aacctaaaaa taaggcaatt agccaaaaac      7320
aactttgcgt gtaaacaacg ctcaatacac gtgtcatttt attattagct attgcttcac      7380
cgccttagct ttctcgtgac ctagtcgtcc tcgtcttttc ttcttcttct tctataaaac      7440
aatacccaaa gcttcttctt cacaattcag atttcaattt ctcaaaatct taaaaacttt      7500
ctctcaattc tctctaccgt gatcaaggta aatttctgtg ttccttattc tctcaaaatc      7560
ttcgattttg ttttcgttcg atcccaattt cgtatatgtt ctttggttta gattctgtta      7620
atcttagatc gaagacgatt ttctgggttt gatcgttaga tatcatctta attctcgatt      7680
agggtttcat aaaatcatc cgatttgttc aaataatttg agttttgtcg aataattact       7740
cttcgatttg tgatttctat ctagatctgg tgttagtttc tagtttgtgc gatcgaattt      7800
gtcgattaat ctgagttttt ctgattaaca gagatctcca tggctcagac cactctccaa      7860
atcacaccca ctggtgccac cttgggtgcc acagtcactg tgttcacct gccacactt        7920 gacgatgctg gtttcgctgc cctccatgca gcctggcttc aacatgcact cttgatcttc      7980
cctgggcaac acctcagcaa tgaccaacag attacctttg ctaaacgctt tggagcaatt      8040
gagaggattg gcggaggtga cattgttgcc atatccaatg tcaaggcaga tggcacagtg      8100
cgccagcact ctcctgctga gtgggatgac atgatgaagg tcattgtggg caacatggcc      8160
tggcacgccg actcaaccta catgccagtc atggctcaag agctgtgtt cagcgcagaa       8220 gttgtcccag cagttggggg cagaacctgc tttgctgaca tgagggcagc ctacgatgcc      8280
cttgatgagg caacccgtgc tcttgttcac caaaggtctg ctcgtcactc ccttgtgtat      8340
tctcagagca agttgggaca tgtccaacag gccgggtcag cctacatagg ttatggcatg      8400
gacaccactg caactcctct cagaccattg gtcaaggtgc atcctgagac tggaaggccc      8460
agcctcttga tcggccgcca tgcccatgcc atccctggca tggatgcagc tgaatcagag      8520
cgcttccttg aaggacttgt tgactgggcc tgccaggctc ccagagtcca tgctcaccaa      8580
tgggctgctg gagatgtggt tgtgtgggac aaccgctgtt tgctccaccg tgctgagccc      8640
tgggatttca agttgccacg tgtgatgtgg cactccagac tcgctggacg cccagaaact      8700
gagggtgctg ccttggtttg agtagttagc ttaatcacct agagctcggt caccagcata      8760
```

```
attttttatta atgtactaaa ttactgtttt gttaaatgca attttgcttt ctcgggattt   8820
taatatcaaa atctatttag aaatacacaa tattttgttg caggcttgct ggagaatcga   8880
tctgctatca taaaaattac aaaaaaattt tatttgcctc aattatttta ggattggtat   8940
taaggacgct taaattattt gtcgggtcac tacgcatcat tgtgattgag aagatcagcg   9000
atacgaaata ttcgtagtac tatcgataat ttatttgaaa attcataaga aaagcaaacg   9060
ttacatgaat tgatgaaaca atacaaagac agataaagcc acgcacattt aggatattgg   9120
ccgagattac tgaatattga gtaagatcac ggaatttctg acaggagcat gtcttcaatt   9180
cagcccaaat ggcagttgaa atactcaaac cgccccatat gcaggagcgg atcattcatt   9240
gtttgtttgg ttgcctttgc caacatggga gtccaaggtt gcggccgcgc gccgacccag   9300
cttccttgta caaagtggtt gcggccgctt aattaaattt aaatgcccgg gcgtttaaac   9360
gcggccgctt aattaaggcc ggcctgcagc aaacccagaa ggtaattatc caagatgtag   9420
catcaagaat ccaatgttta cgggaaaaac tatggaagta ttatgtaagc tcagcaagaa   9480
gcagatcaat atgcggcaca tatgcaacct atgttcaaaa atgaagaatg tacagataca   9540
agatcctata ctgccagaat acgaagaaga atacgtagaa attgaaaaag aagaaccagg   9600
cgaagaaaag aatcttgaag acgtaagcac tgacgacaac aatgaaaaga agaagataag   9660
gtcggtgatt gtgaaagaga catagaggac acatgtaagg tggaaaatgt aagggcggaa   9720
agtaacctta tcacaaagga atcttatccc ccactactta tccttttata tttttccgtg   9780 tcattttttgc ccttgagttt tcctatataa ggaaccaagt tcggcatttg tgaaaacaag   9840
aaaaaatttg gtgtaagcta ttttctttga agtactgagg atacaacttc agagaaattt   9900
gtaagtttgt agatctccat gtctccggag aggagaccag ttgagattag gccagctaca  9960
gcagctgata tggccgcggt ttgtgatatc gttaaccatt acattgagac gtctacagtg  10020
aactttagga cagagccaca aacaccacaa gagtggattg atgatctaga gaggttgcaa  10080
gatagatacc cttggttggt tgctgaggtt gagggtgttg tggctggtat tgcttacgct  10140
gggccctgga aggctaggaa cgcttacgat tggacagttg agagtactgt ttacgtgtca  10200
cataggcatc aaaggtttggg cctaggatcc acattgtaca cacatttgct taagtctatg  10260
gaggcgcaag gttttaagtc tgtggttgct gttataggcc ttccaaacga tccatctgtt  10320
aggttgcatg aggctttggg atacacagcc cggggtacat gcgcgcagc tggatacaag  10380 catggtggat ggcatgatgt tggtttttgg caaagggatt ttgagttgcc agctcctcca  10440
aggccagtta ggccagttac ccagatctga ggtaccctga gcttgagctt atgagcttat  10500
gagcttagag ctcggatcca ctagtaacgg ccgccagtgt gctggaattc gcccttgact  10560
agataggcgc ccagatcggc ggcaatagct tcttagcgcc atcccgggtt gatcctatct  10620
gtgttgaaat agttgcggtg ggcaaggctc tctttcagaa agacaggcgg ccaaaggaac  10680
ccaaggtgag gtgggctatg gctctcagtt ccttgtggaa gcgcttggtc taaggtgcag  10740
aggtgttagc gggatgaagc aaaagtgtcc gattgtaaca agatatgttg atcctacgta  10800
aggatattaa agtatgtatt catcactaat ataatcagtg tattccaata tgtactacga  10860
tttccaatgt ctttattgtc gccgtatgta atcggcgtca caaataatc cccggtgact  10920 ttcttttaat ccaggatgaa ataatatgtt attataattt ttgcgatttg gtccgttata  10980
ggaattgaag tgtgcttgcg gtcgccacca ctcccatttc ataattttac atgtatttga  11040
aaataaaaaa tttatggtat tcaatttaaa cacgtatact tgtaaagaat gatatcttga  11100
aagaaatata gtttaaatat ttattgataa aataacaagt caggtattat agtccaagca  11160
```

```
aaaacataaa tttattgatg caagtttaaa ttcagaaata tttcaataac tgattatatc    11220
agctggtaca ttgccgtaga tgaaagactg agtgcgatat tatggtgtaa tacatagcgg    11280
ccgggtttct agtcaccggt taggatccgt ttaaactcga ggctagcgca tgcacataga    11340
cacacacatc atctcattga tgcttggtaa taattgtcat tagattgttt ttatgcatag    11400
atgcactcga aatcagccaa ttttagacaa gtatcaaacg gatgtgactt cagtacatta    11460
aaaacgtccg caatgtgtta ttaagttgtc taagcgtcaa tttgatttac acatgtgatga   11520 ccccttgatt tattaattttt aaaaaatgtg catgccaatt accaacaata ccaataggat    11580
cccaattaaa ccgatagaga aagcgaggta atcatacacc cgttttcggc tacatggggg    11640
tggtgaggcg atgctattct cacatgccat tttcgttcct actacgaccg ctccaaccat    11700
catctcgaat tccattgtcg gtggagaaac ccaaggcccg cattggacag tgacgacagt    11760
gagggtaacg ctatcagaat gcgtgcgcat caagcagcca aaacgacggc gttggcattt    11820
acgaagtggc gttttggttg tatccgaagc ggcagagggg cgtttaggta aattcgggaa    11880
gcgaaaagca atgagaaata gcgaaacgct tcgtatctct tcactactac tactactact    11940
acacttggtt tctggtagta gtgttttttg ttacgcacac accaaaacgg ctctctcgca    12000
gcccaaaagc t                                                        12011

<210> SEQ ID NO 19
<211> LENGTH: 1550
<212> TYPE: DNA
<213> ORGANISM: Artificial
<220> FEATURE:
<223> OTHER INFORMATION: 5' border and T-strand insert
<220> FEATURE:
<221> NAME/KEY: T-strand insert
<222> LOCATION: (1247)..(1550)

<400> SEQUENCE: 19
agcttatggt tttgtttcaa tacaaggaga caataaaatta gtttagaata ttattttttga    60 aacctatatt attacaatta tatggacata ttagacacat gacaagtata atttgttttt    120
tttttacctc tctaatatat cctcatttgt taccatttct ccacacagtt taagttgaga    180
attaattttc aatattgcaa agttatactt atgatttgaa aatcttgtaa acacaaatga    240
atccgatttt ttttttttt taaagggaaa gcaaatgaat ctgattatgt atgtatgtgt    300
ttttttcttt ctctgcgtaa tcatatatct cttttaaaca cttcaaaaca agatttagaa    360
ttttcattgt aagatattca atcttcaacg cttctttaag gaggtgacat ttttttttatt    420 actttaggct tattttttatt agatatttgg ttcatttctt taatagtacc accaagacca    480
tttgcattta aatgaatact agcatctaag attcaaaata aataattctt tccaacgaca    540
tcaattaaga gcataaattt gagttcaaca aaatttgaca ttccgtatta tcataagata    600
atacaagtta tacaacatcc acaaagaata aaggtgtatc atttaaatga cagctaacat    660
caaacaaaga tgtctgtaaa aaaaaacatc aagcaaagat gaagaatttt ttttttttct    720
tctgtgtgtg tgataagcaa caaagaaaat cccacatgct tggacaggaa agaggaaaa    780 aaacttcata aatatgtaaa tgcttcacaa catgagtcat gctaatatta attatgttat    840
aagaaaaatt caaataaaag aaaagtata gagtagaaag aaaggtgtat agaaaaaaga    900
tagagaagag gtgtgtttaa tttctttctt tctttttata tgtgtttaac ttcttttaac    960
ataataaata tttatacata taataagtag aagtagaaga caattagaga aaacttagaa    1020
agtcatatta tatacatttt tataatatttt tcttagaaac acattcttat tcttattgtt   1080
```

```
aaaagaaact  aatcatatta  tatccttacc  agcaggagaa  gtcaattcaa  atttaacaaa   1140
aggatgaata  tttataaaat  aataatttt   tttgacataa  tttataacaa  aaaataattt   1200
ttttttttgt  aactagaggt  ttctatccta  attttttatt  ctctgaccag  tcagcatcat   1260
cacaccaaaa  gttaggcccg  aatagtttga  aattagaaag  ctcgcaattg  aggtctacag   1320
gccaaattcg  ctcttagccg  tacaatatta  ctcaccggat  cctaaccggt  gtgatcatgg   1380
gccgcgatta  aaaatctcaa  ttatatttgg  tctaatttag  tttggtattg  agtaaaacaa   1440
attcgaacca  aaccaaaata  taaatatata  gttttatat   atatgccttt  aagacttttt   1500
atagaatttt  ctttaaaaaa  tatctagaaa  tatttgcgac  tcttctggca               1550

<210> SEQ ID NO 20
<211> LENGTH: 680
<212> TYPE: DNA
<213> ORGANISM: Artificial
<220> FEATURE:
<223> OTHER INFORMATION: 3' border and T-strand insert
<220> FEATURE:
<221> NAME/KEY: T-strand insert
<222> LOCATION: (1)..(176)

<400> SEQUENCE: 20
gcacatagac  acacacatca  tctcattgat  gcttggtaat  aattgtcatt  agattgtttt     60
tatgcataga  tgcactcgaa  atcagccaat  tttagacaag  tatcaaacgg  atgtgacttc    120
agtacattaa  aaacgtccgc  aatgtgttat  taagttgtct  aagcgtcaat  ttgatttaca    180
catgtatgac  cccttgattt  attaatttta  aaaaatgtgc  atgccaatta  ccaacaatac    240
caataggatc  ccaattaaac  cgatagagaa  agcgaggtaa  tcatacaccc  gttttcggct    300
acatgggggt  ggtgaggcga  tgctattctc  acatgccatt  tcgttcccta  ctacgaccgc    360
tccaaccatc  atctcgaatt  ccattgtcgg  tggagaaacc  caaggcccgc  attggacagt    420
gacgacagtg  agggtaacgc  tatcagaatg  cgtgcgcatc  aagcagccaa  aacgacggcg    480
ttggcattta  cgaagtggcg  ttttggttgt  atccgaagcg  gcagaggggc  gtttaggtaa    540
attcgggaag  cgaaaagcaa  tgagaaatag  cgaaacgctt  cgtatctctt  cactactact    600
actactacta  cacttggttt  ctggtagtag  tgttttttgt  tacgcacaca  ccaaaacggc    660
tctctcgcag  cccaaaagct                                                   680

<210> SEQ ID NO 21
<211> LENGTH: 10256
<212> TYPE: DNA
<213> ORGANISM: Artificial
<220> FEATURE:
<223> OTHER INFORMATION: plasmid pDAB8264

<400> SEQUENCE: 21
agtcagcatc  atcacaccaa  aagttaggcc  cgaatagttt  gaaattagaa  agctcgcaat     60
tgaggtctac  aggccaaatt  cgctcttagc  cgtacaatat  tactcaccgg  atcctaaccg    120
gtgtgatcat  gggccgcgat  taaaaatctc  aattatattt  ggtctaattt  agtttggtat    180
tgagtaaaac  aaaattcgaac  caaaccaaaa  tataaatata  tagttttat   atatatgcct    240 ttaagacttt  ttatagaatt  tctttaaaaa  aatatctaga  aatatttgcg  actcttctgg    300
catgtaatat  ttcgttaaat  atgaagtgct  ccatttttat  taactttaaa  taattggttg    360
tacgatcact  ttcttatcaa  gtgttactaa  aatgcgtcaa  tctctttgtt  cttccatatt    420
catatgtcaa  aacctatcaa  aattcttata  tatctttttc  gaatttgaag  tgaaatttcg    480
```

```
ataatttaaa attaaataga acatatcatt atttaggtat catattgatt tttatactta      540
attactaaat ttggttaact ttgaaagtgt acatcaacga aaaattagtc aaacgactaa      600
aataaataaa tatcatgtgt tattaagaaa attctcctat aagaatattt taatagatca      660
tatgtttgta aaaaaaatta attttttacta acacatatat ttacttatca aaaatttgac    720
aaagtaagat taaaataata ttcatctaac aaaaaaaaaa ccagaaaatg ctgaaaaccc      780
ggcaaaaccg aaccaatcca aaccgatata gttggtttgg tttgattttg atataaaccg      840
aaccaactcg gtccatttgc acccctaatc ataatagctt taatatttca agatattatt      900
aagttaacgt tgtcaatatc ctggaaattt tgcaaaatga atcaagccta tatggctgta     960
atatgaattt aaaagcagct cgatgtggtg gtaatatgta atttacttga ttctaaaaaa    1020
atatcccaag tattaataat ttctgctagg aagaaggtta gctacgattt acagcaaagc    1080
cagaatacaa tgaaccataa agtgattgaa gctcgaaata tacgaaggaa caaatatttt    1140
taaaaaaata cgcaatgact tggaacaaaa gaaagtgata tattttttgt tcttaaacaa    1200
gcatcccctc taaagaatgg cagttttcct ttgcatgtaa ctattatgct cccttcgtta    1260 caaaatttt ggactactat tgggaacttc ttctgaaaat agtggccacc gcttaattaa      1320
ggcgcgccga cgaatgtccc cgatcaaatc tgagggacgt taaagcgatg ataaattgga    1380
accagaatat agaatctttg ttctgctcta gcttttcttc tgtacatttt ttacgattag    1440
actatgattt tcattcaata accaaaattc tgaagtttgt catcaagttg ctcaatcaaa    1500
cttgtaccgg tttgtttcgg tttatatca gctcactgtt acactttaac caaaatcggt      1560
ttatgtctta ataaaggaat tgagtcggtt taactcatat ccgtaccaat gcgacgtcgt    1620
gtccgcgttt cagtagcttt gctcattgtc ttctacggga actttcccgg acataggaac    1680
cgccctttcg ttatcctcat ccatcgtgaa atcaggaaat aaatgttcga agatttgagg    1740 tcaaagtcg aatttcatgt tgtctcttct atttagatac aaaattgaag caatttttcac    1800 caatttaatg ccaaaattta aaacaacgct gataaagtga aacttgattc gatttatatt    1860
tcaaccgaaa ctgctgaagc aagaagaaaa agcgtaatta cacataacaa gaacgctacc    1920
gcaaactact aaacgccaaa cccaatacaa aagtaaaacg cagacgctta agtgagaaac    1980
ccagaaaaca caaacgcgga tcggggggatc cactagttct agagcttaat tcttgacgaa    2040
agtgctcagc acatcgaagt agtcgggaa ggtcttccgg gtgcacccag ggtcccggat     2100
ggtgacgggg acctcggcac aggcggcaag ggagaaagcc atcgccatcc tgtggtcgtc    2160
gtacgtgtcg atcgccgtca cgttcagctt ctccggcggc gtgatgatgc agtagtccgg    2220
cccttcctca acagatgctc ccagcttggt tagctccgtc cggatcgcaa ccatcctctc    2280
ggtctccttt actctccagg aagccacgtc tctgatggct gtcgggccat cggcaaagag    2340
ggcaaccaca gcaagagtca tggcgacatc aggcatcttg ttcatgttga catcaatcgc    2400
cttgaggtgt ttcctcccaa atggctcccg cggtgggcca gtaacagtta cgctagtctc    2460
ggtccatgta accttcgctc ccatcatctc cagtacctca gcaaacttca catcaccctg    2520
caaactggtg gtgccacaac cttccacagt cacagtccct ccagtaattg cagcaccagc    2580
caagaaatag cttgcgcttg aggcatcacc ttcaacatag gcattttag gggacttgta     2640 ttttttgacct cccttaatgt agaatctgtc ccagctatca gaatgctctg ctttcacacc    2700
aaaacgctcc atcaatctca atgtcatttc gacgtacgga atggagatta atttatcaat    2760
gatttcaatc tccacatccc caagagccaa aggagcagcc atcagcaagg cactcaagta    2820
```

```
ctgactgctg atggagccag acagcttgac cttgccacca ggtagccctc cgattccatt    2880
gacacgaaca ggtgggcagt cagtgccaag gaaacaatca acatctgcac caagctgctt    2940
caatccgaca accaagtcgc caatgggtct ctccctcatt cttggtactc catcaagcac    3000
gtaagttgca tttccaccag cagcagtaac agctgctgtc aaggaccgca ttgcgattcc    3060
agcattcccc aagaagagct gcacttcctc tttagcatcc tcaactggga actttccacc    3120
acagccaaca actacagctc ttttggcagc tttgtccgct tcgacagaga gaccaagagt    3180
cctcaaggcc ccgagcatgt agtggacatc ctcactgttc agcaggttat caaccactgt    3240
tgtcccctcg gacagggcgg cgagtaggag gatccggttg gaaagcgact tggaccccgg    3300
cagcttgacg gtgccggaga tctccttgat gggctgcagc acgatctcct cggcgccggc    3360
catgcaccgg atccttccgc cgttgctgac gttgccgagg cttctggagg agcggcgggc    3420
gacggggagg ctggcggtgg acttgagccc ctggaacgga gcgacggcgg tggccgacga    3480
ggccatcatc acgtgtgggcg ccatagacag cggcggcagg tacgacacgcg tctcgaactt    3540
```

```
gtacaaaaaa gcaggctccg cggtgactga ctgaaaagct tgtcgacctg caggtcaacg    5280
gatcaggata ttcttgttta agatgttgaa ctctatggag gtttgtatga actgatgatc    5340
taggaccgga taagttccct tcttcatagc gaacttattc aaagaatgtt ttgtgtatca    5400
ttcttgttac attgttatta atgaaaaaat attattggtc attggactga acacgagtgt    5460
taaatatgga ccaggcccca ataagatcc attgatatat gaattaaata caagaataa     5520 atcgagtcac caaaccactt gccttttta acgagacttg ttcaccaact tgatacaaaa    5580
gtcattatcc tatgcaaatc aataatcata caaaaatatc aataacact aaaaaattaa    5640 aagaaatgga taatttcaca atatgttata cgataaagaa gttacttttc caagaaattc    5700
actgatttta taagcccact tgcattagat aaatggcaaa aaaaacaaa aaggaaaaga    5760 aataaagcac gaagaattct agaaaatacg aaatacgctt caatgcagtg ggacccacgg    5820
ttcaattatt gccaatttc agctccaccg tatatttaaa aaataaaacg ataatgctaa    5880
aaaaatataa atcgtaacga tcgttaaatc tcaacggctg gatcttatga cgaccgttag    5940
aaattgtggt tgtcgacgag tcagtaataa acggcgtcaa agtggttgca gccggcacac    6000
acgagtcgtg tttatcaact caaagcacaa atacttttcc tcaacctaaa ataaggcaa    6060 ttagccaaaa acaactttgc gtgtaaacaa cgctcaatac acgtgtcatt ttattattag    6120
ctattgcttc accgccttag cttttctcgtg acctagtcgt cctcgtcttt tcttcttctt    6180
cttctataaa acaatacca agcttcttc ttcacaattc agatttcaat ttctcaaaat     6240
cttaaaaact ttctctcaat tctctctacc gtgatcaagg taaatttctg tgttccttat    6300
tctctcaaaa tcttcgattt tgttttcgtt cgatcccaat ttcgtatatg ttctttggtt    6360
tagattctgt taatcttaga tcgaagacga ttttctgggt ttgatcgtta gatatcatct    6420
taattctcga ttagggtttc ataaatatca tccgatttgt tcaaataatt tgagttttgt    6480
cgaataatta ctcttcgatt tgtgatttct atctagatct ggtgttagtt tctagttttgt    6540 gcgatcgaat ttgtcgatta atctgagttt ttctgattaa cagagatctc catggctcag    6600
accactctcc aaatcacacc cactggtgcc accttgggtg ccacagtcac tggtgttcac    6660
cttgccacac ttgacgatgc tggtttcgct gccctccatg cagcctggct tcaacatgca    6720
ctcttgatct tccctgggca acacctcagc aatgaccaac agattacctt tgctaaacgc    6780
tttggagcaa ttgagaggat tggcggaggt gacattgttg ccatatccaa tgtcaaggca    6840
gatggcacag tgcgccagca ctctcctgct gagtgggatg acatgatgaa ggtcattgtg    6900
ggcaacatgg cctggcacgc cgactcaacc tacatgccag tcatggctca aggagctgtg    6960
ttcagcgcag aagttgtccc agcagttggg ggcagaacct gctttgctga catgagggca    7020
gcctacgatg cccttgatga ggcaacccgt gctcttgttc accaaaggtc tgctcgtcac    7080
tcccttgtgt attctcagag caagttggga catgtccaac aggccgggtc agcctacata    7140
ggttatggca tggacaccac tgcaactcct ctcagaccat ggtcaaggt gcatcctgag    7200 actggaaggc ccagcctctt gatcggccgc catgcccatg ccatccctgg catggatgca    7260
gctgaatcag agcgcttcct tgaaggactt gttgactggg cctgccaggc tcccagagtc    7320
catgctcacc aatgggctgc tggagatgtg gttgtgtggg acaaccgctg tttgctccac    7380
cgtgctgagc cctgggattt caagttgcca cgtgtgatgt ggcactccag actcgctgga    7440
cgcccagaaa ctgagggtgc tgccttggtt tgagtagtta gcttaatcac ctagagctcg    7500
gtcaccagca taattttat taatgtacta aattactgtt ttgttaaatg caatttgct     7560
```

```
ttctcgggat ttaatatca aaatctattt agaaatacac aatattttgt tgcaggcttg    7620
ctggagaatc gatctgctat cataaaaatt acaaaaaaat tttatttgcc tcaattattt    7680
taggattggt attaaggacg cttaaattat ttgtcgggtc actacgcatc attgtgattg    7740
agaagatcag cgatacgaaa tattcgtagt actatcgata atttatttga aaattcataa    7800
gaaaagcaaa cgttacatga attgatgaaa caatacaaag acagataaag ccacgcacat    7860
ttaggatatt ggccgagatt actgaatatt gagtaagatc acggaatttc tgacaggagc    7920
atgtcttcaa ttcagcccaa atggcagttg aaatactcaa accgccccat atgcaggagc    7980
ggatcattca ttgtttgttt ggttgccttt gccaacatgg gagtccaagg ttgcggccgc    8040
gcgccgaccc agctttcttg tacaaagtgg ttgcggccgc ttaattaaat ttaaatgccc    8100
gggcgtttaa acgcggccgc ttaattaagg ccggcctgca gcaaacccag aaggtaatta    8160
tccaagatgt agcatcaaga atccaatgtt tacgggaaaa actatggaag tattatgtaa    8220
gctcagcaag aagcagatca atatgcggca catatgcaac ctatgttcaa aaatgaagaa    8280
tgtacagata caagatccta tactgccaga atacgaagaa gaatacgtag aaattgaaaa    8340
agaagaacca ggcgaagaaa agaatcttga agacgtaagc actgacgaca acaatgaaaa    8400
gaagaagata aggtcggtga ttgtgaaaga gacatagagg acacatgtaa ggtggaaaat    8460
gtaagggcgg aaagtaacct tatcacaaag gaatcttatc ccccactact tatccttta    8520 tatttttccg tgtcattttt gcccttgagt tttcctatat aaggaaccaa gttcggcatt    8580
tgtgaaaaca agaaaaaatt tggtgtaagc tattttcttt gaagtactga ggatacaact    8640
tcagagaaat ttgtaagttt gtagatctcc atgtctccgg agaggagacc agttgagatt    8700
aggccagcta cagcagctga tatggccgcg gtttgtgata tcgttaacca ttacattgag    8760
acgtctacag tgaactttag gacagagcca caaacaccac aagagtggat tgatgatcta    8820
gagaggttgc aagatagata cccttggttg gttgctgagg ttgagggtgt tgtggctggt    8880
attgcttacg ctgggccctg gaaggctagg aacgcttacg attggacagt tgagagtact    8940
gtttacgtgt cacataggca tcaaaggttg ggcctaggat ccacattgta cacacatttg    9000
cttaagtcta tggaggcgca aggttttaag tctgtggttg ctgttatagg ccttccaaac    9060
gatccatctg ttaggttgca tgaggctttg ggatacacag cccgggtac attgcgcgca    9120 gctggataca agcatggtgg atggcatgat gttggttttt ggcaaaggga ttttgagttg    9180
ccagctcctc caaggccagt taggccagtt acccagatct gaggtaccct gagcttgagc    9240
ttatgagctt atgagcttag agctcggatc cactagtaac ggccgccagt gtgctggaat    9300
tcgcccttga ctagataggc gcccagatcg gcggcaatag cttcttagcg ccatcccggg    9360
ttgatcctat ctgtgttgaa atagttgcgg tgggcaaggc tctctttcag aaagacaggc    9420
ggccaaagga acccaaggtg aggtgggcta tggctctcag ttccttgtgg aagcgcttgg    9480
tctaaggtgc agaggtgtta gcgggatgaa gcaaaagtgt ccgattgtaa caagatatgt    9540
tgatcctacg taaggatatt aaagtatgta ttcatcacta atataatcag tgtattccaa    9600
tatgtactac gatttccaat gtctttattg tcgccgtatg taatcggcgt cacaaaataa    9660
tccccggtga ctttcttta atccaggatg aaataaatatg ttattataat ttttgcgatt    9720
tggtccgtta taggaattga agtgtgcttg cggtcgccac cactcccatt tcataatttt    9780
acatgtattt gaaaaataaa aatttatggt attcaattta aacacgtata cttgtaaaga    9840
atgatatctt gaaagaaata tagtttaaat atttattgat aaaataacaa gtcaggtatt    9900
atagtccaag caaaaacata aatttattga tgcaagttta aattcagaaa tatttcaata    9960
```

```
actgattata tcagctggta cattgccgta gatgaaagac tgagtgcgat attatggtgt  10020
aatacatagc ggccgggttt ctagtcaccg gttaggatcc gtttaaactc gaggctagcg  10080
catgcacata gacacacaca tcatctcatt gatgcttggt aataattgtc attagattgt  10140
ttttatgcat agatgcactc gaaatcagcc aattttagac aagtatcaaa cggatgtgac  10200
ttcagtacat taaaaacgtc cgcaatgtgt tattaagttg tctaagcgtc aatttg      10256
```

STACKED HERBICIDE TOLERANCE EVENT 8264.42.32.1, RELATED TRANSGENIC SOYBEAN LINES, AND DETECTION THEREOF

CROSS REFERENCE TO RELATED APPLICATION

This application claims the benefit under 35 U.S.C §119 (e) of provisional application Ser. No. 61/507,444 filed Jul. 13, 2011 and 61/515,634 filed Aug. 5, 2011. These applications are incorporated herein by reference in their entirety for all purposes.

BACKGROUND OF THE INVENTION

Glyphosate (N-phosphonomethylglycine), a broad-spectrum herbicide, inhibits 5-enolpyruvylshikimate-3-phosphate synthase (EPSPS), an enzyme in the shikimic acid metabolic pathway that produces the essential aromatic amino acids in plant cells. Inhibition of EPSPS effectively disrupts protein synthesis and thereby kills the affected plant cells. Because glyphosate is non-selective to plant cells, it kills both weeds and crop plants. Thus it is useful in agricultural production when one can modify the crop plants to be resistant to glyphosate, allowing the desirable plants to survive exposure to glyphosate.

Recombinant DNA technology has been used to isolate mutant EPSP synthases that are glyphosate-resistant. Such glyphosate-resistant mutant EPSP synthases can be transformed into plants and confer glyphosate-resistance upon the transformed plants. By way of example, a glyphosate tolerance gene was isolated from *Agrobacterium* strain CP4 as described in U.S. Pat. No. 5,633,435. This reference and all references cited are incorporated herein by reference.

Other glyphosate tolerance genes have been created through the introduction of mutations. These include the AroA gene isolated by Comai and described at U.S. Pat. Nos. 5,094,945, 4,769,061 and 4,535,060. A single mutant has been utilized, as described in U.S. Pat. No. 5,310,667, by substituting an alanine residue for a glycine residue between amino acid positions 80 and 120. Double mutants have been described in U.S. Pat. Nos. 6,225,114 and 5,866,775 in which, in addition to the above mutation, a second mutation (a threonine residue for an alanine residue between positions 170 and 210) was introduced into a wild-type EPSPS gene.

Other work resulted in the production of glyphosate resistant maize through the introduction of a modified maize EPSPS gene bearing mutations at residue 102 (changing threonine to isoleucine) and residue 106 (changing proline to serine) of the amino acid sequence encoded by GenBank Accession No. X63374. See U.S. Pat. Nos. 6,566,587 and 6,040,497.

Examples of events providing resistance to glyphosate in soybeans include soybean event GTS 40-3-2 (Padgette et al. 1995) and soybean event MON89788 (U.S. Pat. No. 7,608,761).

The widespread adoption of the glyphosate tolerant cropping system and the increasing use of glyphosate has contributed to the prevalence of glyphosate-resistant and difficult-to-control weeds in recent years. In areas where growers are faced with glyphosate resistant weeds or a shift to more difficult-to-control weed species, growers can compensate for gaps in the herbicide spectrum of glyphosate by tank mixing or alternating with other herbicides that will control the missed weeds.

The herbicide, 2,4-dichlorophenoxyacetic acid (2,4-D), can be used in concert with glyphosate to expect expand the spectrum of broadleaf or dicot weeds that may be tolerant or resistant to glyphosate. 2,4-D, which has been used as a herbicide for more than 60 years, provides broad spectrum, post-emergence control of a wide spectrum of annual, biennial, and perennial broadleaf weeds. In corn, soybean and cotton, 2,4-D (560-1120 g ae/ha rates) controls key weeds including; *Ambrosia artemisiifolia*, *Ambrosia trifida*, *Xanthium strumarium*, *Chenopodium album*, *Helianthus annuus*, *Ipomoea* sp., *Abutilon theophrasti*, *Conyza Canadensis*, and *Senna obtusifolia*. 2,4-D provides partial control of several key weeds including *Polygonum pensylvanicum*, *Polygonum persicaria*, *Cirsium arvense*, *Taraxacum officinale*, and *Amaranthus* sp. including *Amaranthus rudis*, and *Amaranthus palmeri*.

A limitation to further use of 2,4-D is that its selectivity to dicot crops like soybean or cotton is very poor, and hence 2,4-D is not typically used on (and generally not near) sensitive dicot crops. Additionally, 2,4-D's use in grass crops is somewhat limited by the nature of crop injury that can occur. 2,4-D in combination with glyphosate has been used to provide a more robust burndown treatment prior to planting no-till soybeans and cotton; however, due to these dicot species' sensitivity to 2,4-D, these burndown treatments must occur at least 14-30 days prior to planting (Agriliance, 2005).

One organism that has been extensively researched for its ability to degrade 2,4-D is *Ralstonia eutropha*, which contains a gene, tfdA, that codes for an enzyme (TfdA) that catalyzes the first step in the mineralization pathway. (See U.S. Pat. No. 6,153,401 and GENBANK Acc. No. M16730). TfdA catalyzes the conversion of 2,4-D acid to dichlorophenol (DCP) via an α-ketoglutarate-dependent dioxygenase reaction (Smejkal et al., 2001). DCP has little herbicidal activity compared to 2,4-D. tfdA has been used in transgenic plants to impart 2,4-D resistance in dicot plants (e.g., cotton and tobacco) normally sensitive to 2,4-D (Streber et al. (1989), Lyon et al. (1989), Lyon (1993), and U.S. Pat. No. 5,608,147).

A number of tfdA-type genes that encode proteins capable of degrading 2,4-D have been identified from the environment and deposited into the Genbank database. Many homologues are similar to TfdA (>85% amino acid identity) and have similar enzymatic properties to TfdA. However, there are a number of homologues that have a significantly lower identity to TfdA (25-50%), yet have the characteristic residues associated with α-ketoglutarate dioxygenase Fe (II) dioxygenases. Therefore, the substrate specificity of divergent TfdA proteins is not obvious.

An example of a 2,4-D-degrading gene with low homology (<35%) to tfdA is the aad-12 gene from *Delftia acidovorans* (Schleinitz et al. (2004) and Westendorf et al. (2002). The aad-12 gene encodes an S-enantiomer-specific α-ketoglutarate-dependent dioxygenase which has been used in plants to confer tolerance to certain phenoxy auxin herbicides, including, but not limited to: phenoxyalkanoate herbicides (e.g., phenoxyacetic acid herbicides such as 2,4-D and MCPA; and phenoxybutanoic acid herbicides such as 2,4-DB and MCPB) and pyridyloxyalkanoic acid herbicides (e.g., pyridyloxyacetic acid herbicides such as triclopyr and fluroxypyr), and including acid, salt, or ester forms of the active ingredient(s). (See, e.g., WO 2007/053482).

Glufosinate-ammonium ("glufosinate") is a non-systemic, non-selective herbicide in the phosphinothricin class of herbicides. Used primarily for post-emergence control of a wide range of broadleaf and grassy weeds, L-phosphinothricin, the active ingredient in glufosinate, controls weeds through the irreversible inhibition of glutamine-synthase, an enzyme which is necessary for ammonia detoxification in plants. Glufosinate herbicides are sold commercially, for example, under the brand names IGNITE® and LIB-ERTY®.

The enzyme phosphinothricin N-acetyl transferase (PAT), isolated from the soil bacterium *Streptomyces viridochromogenes*, catalyzes the conversion of L-phosphinothricin to its inactive form by acetylation. A plant-optimized form of the gene expressing PAT has been used in soybeans to confer tolerance to glufosinate herbicide. One such example of glufosinate resistant soybeans is event A5547-127. Most recently, the use of glufosinate herbicide in combination with the glufosinate-tolerance trait has been proposed as a non-selective means to effectively manage ALS- and glyphosate resistant weeds.

The expression of heterologous or foreign genes in plants is influenced by where the foreign gene is inserted in the chromosome. This could be due to chromatin structure (e.g., heterochromatin) or the proximity of transcriptional regulation elements (e.g., enhancers) close to the integration site (Weising et al., *Ann. Rev. Genet* 22:421-477, 1988), for example. The same gene in the same type of transgenic plant (or other organism) can exhibit a wide variation in expression level amongst different events. There may also be differences in spatial or temporal patterns of expression. For example, differences in the relative expression of a transgene in various plant tissues may not correspond to the patterns expected from transcriptional regulatory elements present in the introduced gene construct.

Thus, large numbers of events are often created and screened in order to identify an event that expresses an introduced gene of interest to a satisfactory level for a given purpose. For commercial purposes, it is common to produce hundreds to thousands of different events and to screen those events for a single event that has desired transgene expression levels and patterns. An event that has desired levels and/or patterns of transgene expression is useful for introgressing the transgene into other genetic backgrounds by sexual outcrossing using conventional breeding methods. Progeny of such crosses maintain the transgene expression characteristics of the original transformant. This strategy is used to ensure reliable gene expression in a number of varieties that are well adapted to local growing conditions.

BRIEF SUMMARY OF THE INVENTION

The subject invention can provide, in part, effective means for managing weed resistance, which helps preserve the usefulness of herbicide-tolerant technologies. The subject invention can also provide growers with great flexibility and convenience in weed control options.

More specifically, the present invention relates in part to the soybean (*Glycine max*) event designated pDAB8264.42.32.1 ("event pDAB8264.42.32.1") having representative seed deposited with American Type Culture Collection (ATCC) with Accession No. PTA-11993, and progeny derived thereof. The subject invention includes soybean plants comprising event pDAB8264.42.32.1 (and includes soybean plants comprising a transgenic insert between SEQ ID NO:1 and SEQ ID NO:2).

The transgenic insert present in the subject event and deposited seed comprises three herbicide tolerance genes: aad-12, 2mEpsps, and a pat gene. The aad-12 gene, derived from *Delftia acidovorans*, encodes the aryloxyalkanoate dioxygenase (AAD-12) protein, which confers tolerance to, e.g., 2,4-dichlorophenoxyacetic acid and pyridyloxyacetate herbicides. The 2mepsps gene, a modified EPSPS sequence isolated from maize, produces a protein which confers tolerance to glyphosate herbicides. The pat gene, from the soil bacterium *Streptomyces viridochromogenes*, confers tolerance to the herbicide glufosinate.

Other aspects of the invention comprise progeny plants, soybeans, seeds, and/or regenerable parts of the plants and seeds and progeny comprising soybean event pDAB8264.42.32.1, as well as food or feed products made from any thereof. The invention also includes plant parts of Event pDAB8264.42.32.1 that include, but are not limited to, pollen, ovule, flowers, shoots, roots, leaves, nuclei of vegetative cells, pollen cells, and other plant cells that comprise event pDAB8264.42.32.1. The invention further relates to soybean plants having tolerance to multiple herbicides including phenoxy auxinic and/or aryloxyalkanoate herbicides, glyphosate, and/or glufosinate. Such soybean plants may also be stacked with genes that confer tolerance to various other non-selective and selective herbicides, including but not limited to dicamba, imidazolinone, and HPPD herbicides. The invention further includes novel genetic compositions event pDAB8264.42.32.1 and aspects of agronomic performance of soybean plants comprising event pDAB8264.42.32.1.

This invention relates in part to plant breeding and herbicide tolerant plants. This invention includes a novel transformation event in soybean plants comprising a polynucleotide, as described herein, inserted into a specific site within the genome of a soybean cell.

In some embodiments, said event/polynucleotide can be "stacked" with other traits, including, for example, agronomic traits and/or insect-inhibitory proteins. However, the subject invention includes plants having the single event, as described herein.

The additional traits may be stacked into the plant genome, or into the same locus as event pDAB8264.42.32.1, for example via plant breeding, re-transformation of the transgenic plant containing event pDAB8264.42.32.1, or addition of new traits through targeted integration via homologous recombination.

Other embodiments include the excision of a portion or all of the transgenic insert and/or flanking sequences of Event pDAB8264.42.32.1. Upon excision, another and/or additional insert can be targeted to the specific chromosomal site of Event pDAB8264.42.32.1. The exemplified insert can be replaced, or further insert(s) can be stacked, in this manner, with the exemplified insert of the subject soybean event.

In one embodiment, the present invention encompasses a soybean chromosomal target site located on chromosome 15. In some embodiments, the target site comprises a heterologous nucleic acid. In some embodiments, the soybean chromosomal target site is located between the flanking sequences set forth in SEQ ID NO:1 and SEQ ID NO:2.

In one embodiment, the present invention encompasses a method of making a transgenic soybean plant comprising inserting a heterologous nucleic acid at a position on chromosome 15. In another embodiment, the heterologous nucleic acid is inserted on chromosome 15 near or between various exemplified polynucleotide segments as described herein.

Additionally, the subject invention provides assays for detecting the presence of the subject event in a sample (of soybeans, for example). The assays can be based on the DNA sequence of the recombinant construct, inserted into the soybean genome, and on the genomic sequences flanking the insertion site. Kits and conditions useful in conducting the assays are also provided.

Thus, the subject invention relates in part to the cloning and analysis of the DNA sequences of the whole exemplified insert and the border regions thereof (in transgenic soybean lines). These sequences are unique. Based on these insert and border (and junction) sequences, event-specific primers can be and were generated. PCR analysis demonstrated that these events can be identified by analysis of the PCR amplicons generated with these event-specific primer sets. Thus, these and other related procedures can be used to uniquely identify soybean lines comprising the event of the subject invention.

The subject invention also relates in part to endpoint TAQMAN PCR assays for the detection of event 8264.42.32.1. Some embodiments are directed to assays that are capable of zygosity analysis. The subject invention further relates, in part, to the use of a GMFL01-25-J19 (GenBank: AK286292.1) reference gene for use in determining zygosity. These and other related procedures can be used to uniquely identify the zygosity of event pDAB8264.42.32.1 and breed soybean lines comprising the event.

BRIEF DESCRIPTION OF THE SEQUENCES

Figure 1:
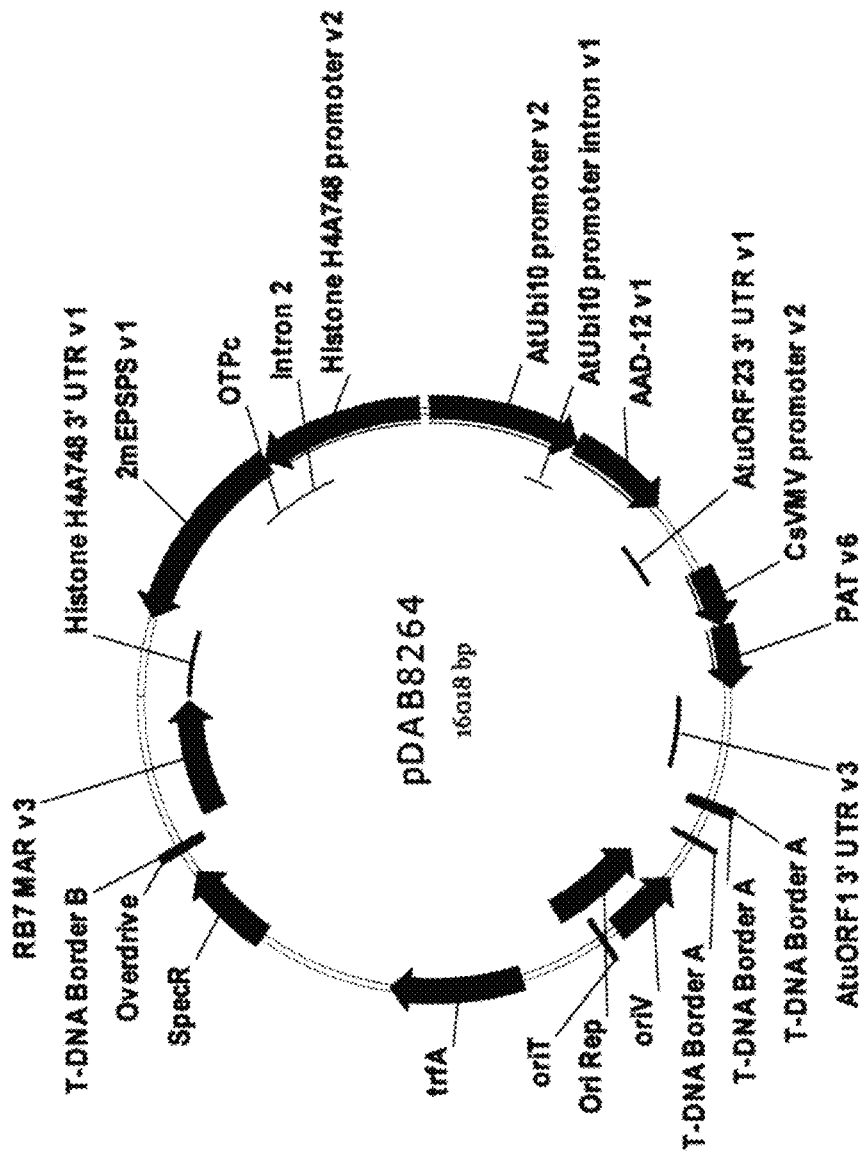
FIG. 1: is a plasmid map of pDAB8264.

SEQ ID NO:1 provides the 5' flanking border sequence for the subject soybean Event pDAB8264.42.32.1.
SEQ ID NO:2 provides the 3' flanking border sequence for the subject soybean Event pDAB8264.42.32.1.
SEQ ID NO:3 provides primer 4232_WF1.
SEQ ID NO:4 provides primer 4232_WF3.
SEQ ID NO:5 provides primer 4232_WF4.
SEQ ID NO:6 provides primer 4232_WR1.
SEQ ID NO:7 provides primer 4232_WR2.
SEQ ID NO:8 provides primer 4232_WR3.
SEQ ID NO:9 provides primer 4232_WR4.
SEQ ID NO:10 provides primer ED_v1_C1.
SEQ ID NO:11 provides primer PAT_11.
SEQ ID NO:12 provides primer 4232_3'F.
SEQ ID NO:13 provides primer 4232_3'R.
SEQ ID NO:14 provides probe 4232_3'P.
SEQ ID NO:15 provides primer GMS116F.
SEQ ID NO:16 provides primer GMS116R.
SEQ ID NO:17 provides probe GMS116Probe.
SEQ ID NO:18 provides the pDAB8264 T-strand insert and partial 5' and 3' genomic flanking sequences.
SEQ ID NO:19 provides the 5' genomic-to-insert sequence (including that junction) for the subject soybean Event pDAB8264.42.32.1.
SEQ ID NO:20 provides the 3' insert-to-plant junction for the subject soybean Event pDAB8264.42.32.1.

SEQ ID NO:21 provides the sequence for plasmid pDAB8264.

DETAILED DESCRIPTION OF THE INVENTION

The invention described herein includes novel transformation events of soybean plants (soybean) comprising a cassette for the expression of multiple herbicide tolerance genes inserted into a specific locus within the genome of a soybean cell. Specifically, novel soybean lines containing the pDAB8264.42.32.1 event were developed. This transgenic event provides tolerance to multiple herbicides including phenoxy auxinic and/or aryloxyalkanoate herbicides, glyphosate, and/or glufosinate. The tolerance to multiple herbicides enables growers to choose an optimal combination of herbicides to best manage their individual weed populations.

The exemplified transgenic insert comprising Event pDAB8264.42.32.1 includes genetic elements for the expression of three different herbicide tolerance genes: (1) a synthetic aad-12 gene; (2) a modified EPSPS sequence from maize encoding a protein containing mutations, as compared to the wild-type EPSPS polypeptide: at amino acid residues 102 (from threonine to isoleucine) and 106 (from proline to serine) and which confers resistance or tolerance to glyphosate herbicides; and (3) a pat gene which confers tolerance or resistance to the glufosinate herbicides. The aad-12 gene was derived from *Delftia acidovorans* and encodes an aryloxyalkanoate dioxygenase (AAD-12) protein enzyme capable of deactivating herbicides having an α-ketoglutarate moiety, including phenoxyalkanoate herbicides (e.g., phenoxyacetic acid herbicides such as 2,4-D and MCPA; and phenoxybutanoic acid herbicides such as 2,4-DB and MCPB) and pyridyloxyalkanoic acid herbicides (e.g., pyridyloxyacetic acid herbicides such as triclopyr and fluroxypyr), including acid, salt, or ester forms of the active ingredient(s)

The subject invention also provides assays for detecting the presence of the subject event in a sample. Aspects of the subject invention include methods of designing and/or producing any diagnostic nucleic acid molecules exemplified or suggested herein, particularly those based wholly or partially on the subject flanking sequences.

This invention relates in part to plant breeding and herbicide tolerant plants. In some embodiments, said polynucleotide sequence can be "stacked" with other traits (such as other herbicide tolerance gene(s) and/or gene(s) that encode insect-inhibitory proteins or inhibitory RNA sequences, for example). However, the subject invention also includes plants having a single event, as described herein.

More specifically, the subject invention relates in part to transgenic soybean Event pDAB8264.42.32.1, plant lines comprising these events, and the cloning and analysis of the DNA sequences of this insert, and/or the border regions thereof. Plant lines of the subject invention can be detected using sequences disclosed and suggested herein.

Figure 2:
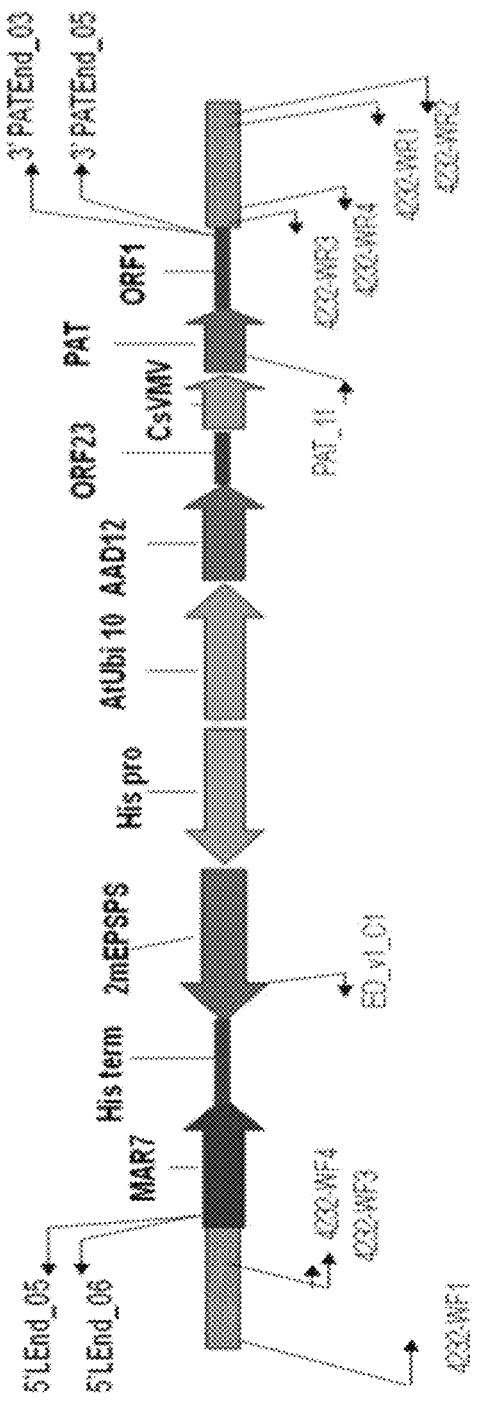
FIG. 2: is a schematic diagram depicting primer locations for confirming the 5' and 3' border sequence of soybean event pDAB8264.42.32.1.

In some embodiments, a polynucleotide segment exemplified or described herein (such as SEQ ID NO:1, SEQ ID NO:2, and/or the insert there between, as depicted in FIG. 2 for example) can be excised and subsequently re-targeted with additional polynucleotide sequence(s).

In some embodiments, this invention relates to herbicide-tolerant soybean lines, and the identification thereof. The subject invention relates in part to detecting the presence of the subject event in order to determine whether progeny of a sexual cross contain the event of interest. In addition, a method for detecting the event is included and is helpful, for example, for complying with regulations requiring the pre-market approval and labeling of foods derived from recombinant crop plants, for example. It is possible to detect the presence of the subject event by any well-known nucleic acid detection method such as polymerase chain reaction (PCR) or DNA hybridization using nucleic acid probes. Event-specific PCR assays are discussed herein. (See e.g. Windels et al. (Med. Fac. Landbouww, Univ. Gent 64/5b: 459462, 1999) for another example.) Some of these examples relate to using a primer set spanning the junction between the insert and flanking DNA.

Exemplified herein is soybean Event pDAB8264.42.32.1, and its selection and characterization for stability and expression at whole plant and molecular levels from generation to generation. Both flanking sequences of Event pDA8264.42.32.1 have been sequenced and are described herein as SEQ ID NO:1 and SEQ ID NO:2. Event specific assays were developed. It has also been mapped onto the soybean genome (soybean chromosome 15). Event pDAB8264.42.32.1 can be introgressed into elite cultivars where it will confer tolerance to phenoxy auxin, glyphosate and glufosinate herbicides in inbred and hybrid soybean lines.

The subject EPSPS gene encodes a mutant 5-enolpyruvyl-3-phosphoshikimic acid synthase (EPSPS). The wild-type EPSPS gene was originally isolated from Zea mays, and the sequence was deposited under GenBank accession number X63374. See also U.S. Pat. No. 6,566,587 (in particular, SEQ ID No. 3 therein).

To obtain high expression of heterologous genes in plants, it may be preferred to reengineer said genes so that they are more efficiently expressed in plant cells. Modification of the wild-type plant EPSPS nucleotide sequence can provide such resistance when expressed in a plant cell. As described in the '587 patent, when comparing an EPSPS polypeptide to the wild-type polypeptide, modification to substitute isoleucine for threonine at residue 102 and substitute serine for proline at position 106 of the protein, the result is the double mutant EPSPS polypeptide (2mEPSPS) used in the subject insert. When expressed in a plant cell, it provides tolerance to glyphosate. The subject EPSPS gene, also referred to as the "2mepsps gene" or DMMG, can alternatively be optimized to improve expression in both dicotyledonous plants as well as monocotyledonous plants, and in particular in soybean. Codon usage can be selected based upon preferred hemicot codon usage, i.e. redesigned such that the protein is encoded by codons having a bias toward both monocot and dicot plant usage. Deleterious sequences and superfluous restriction sites can be removed to increase the efficiency of transcription/translation of the 2mepsps coding sequence and to facilitate DNA manipulation steps. A hemicot-optimized version of the subject monocot gene is further detailed in U.S. provisional application (Ser. No. 61/419,703) filed on Dec. 3, 2010, entitled, "OPTIMIZED EXPRESSION OF GLYPHOSATE RESISTANCE ENCODING NUCLEIC ACID MOLECULES IN PLANT CELLS."

As previously referenced herein, the introduction and integration of a transgene into a plant genome involves some random events (hence the name "event" for a given insertion that is expressed). That is, with many transformation techniques such as Agrobacterium transformation, the "gene gun," and WHISKERS, it is unpredictable where in the genome a transgene will become inserted. Thus, identifying the flanking plant genomic DNA on both sides of the insert can be important for identifying a plant that has a given insertion event. For example, PCR primers can be designed that generate a PCR amplicon across the junction region of the insert and the host genome. This PCR amplicon can be used to identify a unique or distinct type of insertion event.

During the process of introducing an insert into the genome of plant cells, it is not uncommon for some deletions or other alterations of the insert and/or genomic flanking sequences to occur. Thus, the relevant segment of the plasmid sequence provided herein might comprise some minor variations. The same is true for the flanking sequences provided herein. Thus, a plant comprising a polynucleotide having some range of identity with the subject flanking and/or insert sequences is within the scope of the subject invention. Identity to the sequence of the present invention can be a polynucleotide sequence having at least 65% sequence identity, more preferably at least 70% sequence identity, more preferably at least 75% sequence identity, more preferably at least 80% identity, and more preferably at least 85% 86%, 87%, 88%, 89%, 90%, 91%, 92%, 93%, 94%, 95%, 96%, 97%, 98%, 99% sequence identity with a sequence exemplified or described herein. Hybridization and hybridization conditions as provided herein can also be used to define such plants and polynucleotide sequences of the subject invention. The sequence which comprises the flanking sequences plus the full insert sequence can be confirmed with reference to the deposited seed.

As "events" are originally random events, as part of this disclosure at least 2500 seeds of a soybean line comprising the event have been deposited and made available to the public without restriction (but subject to patent rights), with the American Type Culture Collection (ATCC), 10801 University Boulevard, Manassas, Va., 20110. The deposit has been designated as ATCC Deposit No. PTA-11993. 100 packets (25 seeds per packet) of Glycine max seeds (Soybean Seed Glycine max L.: pDAB8264.42.32.1) were deposited on Jul. 11, 2011. The deposit was tested on Jul. 26, 2011, and on that date, the seeds were viable. This deposit was made and will be maintained in accordance with and under the terms of the Budapest Treaty with respect to seed deposits for the purposes of patent procedure. The deposit will be maintained without restriction at the ATCC depository, which is a public depository, for a period of 30 years, or five years after the most recent request, or for the effective life of the patent, whichever is longer, and will be replaced if it becomes nonviable during that period.

The deposited seeds are part of the subject invention. Clearly, soybean plants can be grown from these seeds, and such plants are part of the subject invention. The subject invention also relates to DNA sequences contained in these soybean plants that are useful for detecting these plants and progeny thereof. Detection methods and kits of the subject invention can be directed to identifying any one, two, or even all three of these events, depending on the ultimate purpose of the test.

Definitions and examples are provided herein to help describe the present invention and to guide those of ordinary skill in the art to practice the invention. Unless otherwise noted, terms are to be understood according to conventional usage by those of ordinary skill in the relevant art. The nomenclature for DNA bases as set forth at 37 CFR §1.822 is used.

As used herein, the term "progeny" denotes the offspring of any generation of a parent plant which comprises soybean Event pDAB8264.42.32.1.

A transgenic "event" is produced by transformation of plant cells with heterologous DNA, i.e., a nucleic acid construct that includes a transgene of interest, regeneration of a population of plants resulting from the insertion of the transgene into the genome of the plant, and selection of a particular plant characterized by insertion into a particular genome location. The term "event" refers to the original transformant and progeny of the transformant that include the heterologous DNA. The term "event" also refers to progeny produced by a sexual outcross between the transformant and another variety that includes the genomic/transgene DNA. Even after repeated back-crossing to a recurrent parent, the inserted transgene DNA and flanking genomic DNA (genomic/transgene DNA) from the transformed parent is present in the progeny of the cross at the same chromosomal location. The term "event" also refers to DNA from the original transformant and progeny thereof comprising the inserted DNA and flanking genomic sequence immediately adjacent to the inserted DNA that would be expected to be transferred to a progeny that receives inserted DNA including the transgene of interest as the result of a sexual cross of one parental line that includes the inserted DNA (e.g., the original transformant and progeny resulting from selfing) and a parental line that does not contain the inserted DNA.

A "junction sequence" spans the point at which DNA inserted into the genome is linked to DNA from the soybean native genome flanking the insertion point, the identification or detection of one or the other junction sequences in a plant's genetic material being sufficient to be diagnostic for the event. Included are the DNA sequences that span the insertions in herein-described soybean events and similar lengths of flanking DNA. Specific examples of such diagnostic sequences are provided herein; however, other sequences that overlap the junctions of the insertions, or the junctions of the insertions and the genomic sequence, are also diagnostic and could be used according to the subject invention.

The subject invention relates in part to event identification using such flanking, junction, and insert sequences. Related PCR primers and amplicons are included in the invention. According to the subject invention, PCR analysis methods using amplicons that span across inserted DNA and its borders can be used to detect or identify commercialized transgenic soybean varieties or lines derived from the subject proprietary transgenic soybean lines.

The binary plasmid, pDAB8264 (SEQ ID NO:21) comprises the genetic elements depicted in FIG. 1. The following genetic elements (T-strand border sequences are not included) are contained within the T-strand region of pDAB8264. In Table 1, the residue numbering of the genetic elements is provided with respect to SEQ ID NO:21 disclosed herein.

TABLE 1

Residue Numbering of the Genetic Elements Comprising Binary Plasmid pDAB8264 (SEQ ID NO: 21).

| Genetic Element | Position | Reference |
| --- | --- | --- |
| RB7 MARv3 (Matrix Attachment Region) | 137 bp-1302 bp | Thompson and Myatt, (1997) Plant Mol. Biol., 34: 687-692.; WO9727207 |
| Intervening Sequence | 1303 bp-1341 bp | Not applicable |
| Histone H4A7 48 3'UTR (Untranslated Region) | 1342 bp-2002 bp | Chabouté et al., (1987) Plant Mol. Biol., 8: 179-191 |
| Intervening Sequence | 2003 bp-2025 bp | Not applicable |
| 2mEPSPS v1 | 2026 bp-3363 bp | U.S. Pat. No. 6,566,587 |
| OTPc (optimized transit peptide) | 3364 bp-3735 bp | U.S. Pat. No. 5,510,471 |
| Intervening Sequence | 3736 bp-3748 bp | Not applicable |
| Intron 2 | 3749 bp-4214 bp | Chaubet et al., (1992) J. Mol Bio., 225: 569-574 |
| Histone H4A7 48 Promoter | 4215 bp-5169 bp | Chabouté et al., (1987) Plant Mol. Biol., 8: 179-191 |
| Intervening Sequence | 5170 bp-5261 bp | Not applicable |
| AtUbi 10 Promoter (Arabidopsis thaliana Ubiquitin 10 Promoter) | 5262 bp-6583 bp | Callis, et al., (1990) J. Biol. Chem., 265: 12486-12493 |
| Intervening Sequence | 6584 bp-6591 bp | Not applicable |
| aad-12 v1 | 6592 bp-7473 bp | WO 2007/053482 |
| Intervening Sequence containing stop codons in all 6-frames | 7474 bp-7575 bp | Not applicable |
| AtuORF23 3' UTR (Agrobacterium tumefaciens Open Reading Frame 23 UTR) | 7576 bp-8032 bp | U.S. Pat. No. 5,428,147 |
| Intervening Sequence | 8033 bp-8146 bp | Not applicable |
| CsVMV Promoter (Cassava Vein Mosaic Virus Promoter) | 8147 bp-8663 bp | Verdaguer et al., (1996) Plant Mol. Biol., 31: 1129-1139 |
| Intervening Sequence | 8664 bp-8670 bp | Not applicable |
| pat v6 | 8671 bp-9222 bp | Wohlleben et al., (1988) Gene 70: 25-37 |
| Intervening Sequence containing stop codons in all 6-frames | 9223 bp-9324 bp | Not applicable |
| AtuORF1 3'UTR (Agrobacterium tumefaciens Open Reading Frame 1 UTR) | 9325 bp-10028 bp | Huang et al., (1990) J. Bacteriol. 172: 1814-1822 |

SEQ ID NOs: 19 and 20, respectively, are the 5' and 3' flanking sequences together with 5' and 3' portions of the insert sequence, as described in more detail below, and thus include the 5' and 3' "junction" or "transition" sequences of the insert and the genomic DNA. With respect to SEQ ID NO:19, residues 1-1246 are 5' genomic flanking sequence, and residues 1247-1550 are residues of the 5' end of the insert. With respect to SEQ ID NO:20, residues 1-176 are residues of the 3' end of the insert, and residues 177-680 are 3' genomic flanking sequence. The junction sequence or transition with respect to the 5' end of the insert thus occurs at residues 1246-1247 of SEQ ID NO:19. The junction sequence or transition with respect to the 3' end of the insert thus occurs at residues 176-177 of SEQ ID NO:20. Polynucleotides of the subject invention include those comprising, for example, 5, 10, 20, 50, 100, 150, or 200 bases, or possibly more, and any increments there between, on either side of the junction sequence. Thus, a primer spanning the junction sequence could comprise, for example, 5-10 bases that would hybridize with flanking sequence and 5-10 bases that would hybridize with insert sequence. Probes and amplicons could be similarly designed, although they would often be longer than primers.

The subject sequences (including the flanking sequences) are unique. Based on these insert and border sequences, event-specific primers were generated. PCR analysis demonstrated that these soybean lines can be identified in different soybean genotypes by analysis of the PCR amplicons generated with these event-specific primer sets. Thus, these and other related procedures can be used to uniquely identify these soybean lines. The sequences identified herein are unique.

Detection techniques of the subject invention are especially useful in conjunction with plant breeding, to determine which progeny plants comprise a given event, after a parent plant comprising an event of interest is crossed with another plant line in an effort to impart one or more additional traits of interest in the progeny. These PCR analysis methods benefit soybean breeding programs as well as quality control, especially for commercialized transgenic soybean seeds. PCR detection kits for these transgenic soybean lines can also now be made and used. This can also benefit product registration and product stewardship.

Furthermore, flanking soybean/genomic sequences can be used to specifically identify the genomic location of each insert. This information can be used to make molecular marker systems specific to each event. These can be used for accelerated breeding strategies and to establish linkage data.

Still further, the flanking sequence information can be used to study and characterize transgene integration processes, genomic integration site characteristics, event sorting, stability of transgenes and their flanking sequences, and gene expression (especially related to gene silencing, transgene methylation patterns, position effects, and potential expression-related elements such as MARS [matrix attachment regions], and the like).

In light of the subject disclosure, it should be clear that the subject invention includes seeds deposited for the subject event on Jul. 11, 2011—available under ATCC Deposit No. PTA-11993. The subject invention also includes a herbicide-tolerant soybean plant grown from a seed deposited with the ATCC under this accession number on this date. The subject invention further includes parts of said plant, such as leaves, tissue samples, seeds produced by said plant, pollen, meal (soy meal), and the like (wherein they comprise a transgenic insert flanked by SEQ ID NO:1 and SEQ ID NO:2). The subject invention further includes non-totipotent cells from any of the subject plants (including cells from the parts of such plants as listed above).

Still further, the subject invention includes descendant and/or progeny plants of plants grown from the deposited seed, preferably a herbicide-resistant soybean plant wherein said plant has a genome comprising a detectable wild-type genomic DNA/insert DNA junction sequence as described herein. As used herein, the term "soybean" means *Glycine max* and includes all varieties thereof that can be bred with a soybean plant.

The invention further includes processes of making crosses using a plant of the subject invention as at least one parent. For example, the subject invention includes an $F_1$ hybrid plant having as one or both parents any of the plants exemplified herein. Also within the subject invention is seed produced by such $F_1$ hybrids of the subject invention. This invention includes a method for producing an $F_1$ hybrid seed by crossing an exemplified plant with a different (e.g. in-bred parent) plant and harvesting the resultant hybrid seed. The subject invention includes an exemplified plant that is either a female parent or a male parent. Characteristics of the resulting plants may be improved by careful consideration of the parent plants.

A herbicide-tolerant soybean plant of the subject invention can be bred by first sexually crossing a first parental soybean plant consisting of a soybean plant grown from seed of any one of the lines referred to herein, and a second parental soybean plant, thereby producing a plurality of first progeny plants; then selecting a first progeny plant that is resistant to a herbicide (or that possesses at least one of the events of the subject invention); selfing the first progeny plant, thereby producing a plurality of second progeny plants; and then selecting from the second progeny plants a plant that is resistant to a herbicide (or that possesses at least one of the events of the subject invention). These steps can further include the back-crossing of the first progeny plant or the second progeny plant to the second parental soybean plant or a third parental soybean plant. A soybean crop comprising soybean seeds of the subject invention, or progeny thereof, can then be planted.

It is also to be understood that two different transgenic plants can also be mated to produce offspring that contain two independently segregating, added, exogenous genes. Selfing of appropriate progeny can produce plants that are homozygous for both added, exogenous genes. Back-crossing to a parental plant and out-crossing with a non-transgenic plant are also contemplated, as is vegetative propagation. Other breeding methods commonly used for different traits and crops are known in the art. Backcross breeding has been used to transfer genes for a simply inherited, highly heritable trait into a desirable homozygous cultivar or inbred line, which is the recurrent parent. The source of the trait to be transferred is called the donor parent. The resulting plant is expected to have the attributes of the recurrent parent (e.g., cultivar) and the desirable trait transferred from the donor parent. After the initial cross, individuals possessing the phenotype of the donor parent are selected and repeatedly crossed (backcrossed) to the recurrent parent. The resulting parent is expected to have the attributes of the recurrent parent (e.g., cultivar) and the desirable trait transferred from the donor parent.

The DNA molecules of the present invention can be used as molecular markers in a marker assisted breeding (MAB) method. DNA molecules of the present invention can be used in methods (such as, AFLP markers, RFLP markers, RAPD markers, SNPs, and SSRs) that identify genetically linked agronomically useful traits, as is known in the art. The herbicide-resistance trait can be tracked in the progeny of a cross with a soybean plant of the subject invention (or progeny thereof and any other soybean cultivar or variety) using the MAB methods. The DNA molecules are markers for this trait, and MAB methods that are well known in the art can be used to track the herbicide-resistance trait(s) in soybean plants where at least one soybean line of the subject invention, or progeny thereof, was a parent or ancestor. The methods of the present invention can be used to identify any soybean variety having the subject event.

Methods of the subject invention include a method of producing a herbicide-tolerant soybean plant wherein said method comprises introgressing Event pDAB8264.42.32.1 into a soybean cultivar. More specifically, methods of the present invention can comprise crossing two plants of the subject invention, or one plant of the subject invention and any other plant. Preferred methods further comprise selecting progeny of said cross by analyzing said progeny for an event detectable according to the subject invention. For example, the subject invention can be used to track the subject event through breeding cycles with plants comprising other desirable traits, such as agronomic traits such as those tested herein in various Examples. Plants comprising the subject event and the desired trait can be detected, identified, selected, and quickly used in further rounds of breeding, for example. The subject event/trait can also be combined through breeding, and tracked according to the subject invention, with an insect resistant trait(s) and/or with further herbicide tolerance traits. One embodiment of the latter is a plant comprising the subject event combined with a gene encoding resistance to the herbicide dicamba.

Thus, the subject invention can be combined with, for example, additional traits encoding glyphosate resistance (e.g., resistant plant or bacterial glyphosate oxidase (GOX)), glyphosate acetyl transferase (GAT), additional traits for glufosinate resistance (e.g. bialaphos resistance (bar)), traits conferring acetolactate synthase (ALS)-inhibiting herbicide resistance (e.g., imidazolinones [such as imazethapyr], sulfonylureas, triazolopyrimidine sulfonanilide, pyrmidinylthiobenzoates, and other chemistries [Csr1, SurA, et al.]), bromoxynil resistance traits (e.g., Bxn), traits for resistance to dicamba herbicide (see, e.g., U.S. 2003/0135879), traits for resistance to inhibitors of HPPD (4-hydroxlphenyl-pyruvate-dioxygenase) enzyme, traits for resistance to inhibitors of phytoene desaturase (PDS), traits for resistance to photosystem II inhibiting herbicides (e.g., psbA), traits for resistance to photosystem I inhibiting herbicides, traits for resistance to protoporphyrinogen oxidase IX (PPO)-inhibiting herbicides (e.g., PPO-1), and traits for resistance to phenylurea herbicides (e.g., CYP76B1). One or more of such traits can be combined with the subject invention to provide the ability to effectively control, delay and/or prevent weed shifts and/or resistance to herbicides of multiple classes.

It will be appreciated by those of skill in the art that the aad-12 gene used in the subject invention also provides resistance to compounds that are converted to phenoxyacetate auxin herbicides (e.g., 2,4 DB, MCPS, etc.). The butyric acid moiety present in the 2,4-DB herbicide is converted through β-oxidation to the phytotoxic 2,4-dichlorophenoxyacetic acid. Likewise, MCPB is converted through β-oxidation to the phytotoxic MCPA. The butanoic acid herbicides are themselves nonherbicidal, but are converted to their respective acid from by β-oxidation within susceptible plants to produce the acetic acid form of the herbicide that is phytotoxic. Plants incapable of rapid β-oxidation are not harmed by the butanoic acid herbicides. However, plants that are capable of rapid β-oxidation and can convert the butanoic acid herbicide to the acetic form are subsequently protected by AAD-12.

Methods of applying herbicides are well known in the art. Such applications can include tank mixes of more than one herbicide. Preferred herbicides for use according to the subject invention are combinations of glyphosate, glufosinate, and a phenoxy auxin herbicide (such as 2,4-D; 2,4-DB; MCPA; MCPB). Other preferred combinations include glyphosate plus 2,4-D or glufosinate plus 2,4-D mixtures. These three types of herbicides can be used in advantageous combinations that would be apparent to one skilled in the art having the benefit of the subject disclosure. One or more of the subject herbicides can be applied to a field/area prior to planting it with seeds of the subject invention. Such applications can be within 14 days, for example, of planting seeds of the subject invention. One or more of the subject herbicides can also be applied after planting prior to emergence. One or more of the subject herbicides can also be applied to the ground (for controlling weeds) or over the top of the weeds and/or over the top of transgenic plants of the subject invention. The subject three herbicides can be rotated or used in combination to, for example, control or prevent weeds that might to tolerant to one herbicide but not another. Various application times for the subject three types of herbicides can be used in various ways as would be known in the art.

Additionally, the subject event can be stacked with one or more additional herbicide tolerance traits, one or more additional input (e.g., insect resistance, fungal resistance, or stress tolerance, et al.) or output (e.g., increased yield, improved oil profile, improved fiber quality, et al.) traits, both transgenic and nontransgenic. Thus, the subject invention can be used to provide a complete agronomic package of improved crop quality with the ability to flexibly and cost effectively control any number of agronomic pests.

Methods to integrate a polynucleotide sequence within a specific chromosomal site of a plant cell via homologous recombination have been described within the art. For instance, site specific integration as described in U.S. Patent Application Publication No. 2009/0111188 A1, describes the use of recombinases or integrases to mediate the introduction of a donor polynucleotide sequence into a chromosomal target. In addition, International Patent Application No. WO 2008/021207, describes zinc finger mediated-homologous recombination to integrate one or more donor polynucleotide sequences within specific locations of the genome. The use of recombinases such as FLP/FRT as described in U.S. Pat. No. 6,720,475, or CRE/LOX as described in U.S. Pat. No. 5,658,772, can be utilized to integrate a polynucleotide sequence into a specific chromosomal site. Finally the use of meganucleases for targeting donor polynucleotides into a specific chromosomal location was described in Puchta et al., PNAS USA 93 (1996) pp. 5055-5060).

Other various methods for site specific integration within plant cells are generally known and applicable (Kumar et al., *Trends in Plant Sci.* 6(4) (2001) pp. 155-159). Furthermore, site-specific recombination systems which have been identified in several prokaryotic and lower eukaryotic organisms may be applied to use in plants. Examples of such systems include, but are not limited too; the R/RS recombinase system from the pSR1 plasmid of the yeast *Zygosaccharomyces rouxii* (Araki et al. (1985) J. Mol. Biol. 182: 191-203), and the Gin/gix system of phage Mu (Maeser and Kahlmann (1991) Mol. Gen. Genet. 230: 170-176).

In some embodiments of the present invention, it can be desirable to integrate or stack a new transgene(s) in proximity to an existing transgenic event. The transgenic event can be considered a preferred genomic locus which was selected based on unique characteristics such as single insertion site, normal Mendelian segregation and stable expression, and a superior combination of efficacy, including herbicide tolerance and agronomic performance in and across multiple environmental locations. The newly integrated transgenes should maintain the transgene expression characteristics of the existing transformants. Moreover, the development of assays for the detection and confirmation of the newly integrated event would be overcome as the genomic flanking sequences and chromosomal location of the newly integrated event are already identified. Finally, the integration of a new transgene into a specific chromosomal location which is linked to an existing transgene would expedite the introgression of the transgenes into other genetic backgrounds by sexual out-crossing using conventional breeding methods.

In some embodiments of the present invention, it can be desirable to excise polynucleotide sequences from a transgenic event. For instance transgene excision as described in Provisional U.S. Patent Application No. 61/297,628, describes the use of zinc finger nucleases to remove a polynucleotide sequence, consisting of a gene expression cassette, from a chromosomally integrated transgenic event. The polynucleotide sequence which is removed can be a selectable marker. Upon excision and removal of a polynucleotide sequence the modified transgenic event can be retargeted by the insertion of a polynucleotide sequence. The excision of a polynucleotide sequence and subsequent retargeting of the modified transgenic event provides advantages such as re-use of a selectable marker or the ability to overcome unintended changes to the plant transcriptome which results from the expression of specific genes.

The subject invention discloses herein a specific site on chromosome 15 in the soybean genome that is excellent for insertion of heterologous nucleic acids. Also disclosed is a 5' flanking sequence and a 3' flanking sequence, which can also be useful in identifying and/or targeting the location of the insertion/targeting site on chromosome 15. Thus, the subject invention provides methods to introduce heterologous nucleic acids of interest into this pre-established target site or in the vicinity of this target site. The subject invention also encompasses a soybean seed and/or a soybean plant comprising any heterologous nucleotide sequence inserted at the disclosed target site or in the general vicinity of such site. One option to accomplish such targeted integration is to excise and/or substitute a different insert in place of the pat expression cassette exemplified herein. In this general regard, targeted homologous recombination, for example and without limitation, can be used according to the subject invention.

As used herein, gene event or trait "stacking" is combining desired traits into one transgenic line. Plant breeders stack transgenic traits by making crosses between parents that each have a desired trait and then identifying offspring that haw both of these desired traits. Another way to stack genes is by transferring two or more genes into the cell nucleus of a plant at the same time during transformation. Another way to stack genes is by re-transforming a transgenic plant with another gene of interest. For example, gene stacking can be used to combine two or more different traits, including for example, two or more different insect traits, insect resistance trait(s) and disease resistance trait(s), two or more herbicide resistance traits, and/or insect resistance trait(s) and herbicide resistant trait(s). The use of a selectable marker in addition to a gene of interest can also be considered gene stacking.

"Homologous recombination" refers to a reaction between any pair of nucleotide sequences having corresponding sites containing a similar nucleotide sequence through which the two nucleotide sequences can interact (recombine) to form a new, recombinant DNA sequence. The sites of similar nucleotide sequence are each referred to herein as a "homology sequence." Generally, the frequency of homologous recombination increases as the length of the homology sequence increases. Thus, while homologous recombination can occur between two nucleotide sequences that are less than identical, the recombination frequency (or efficiency) declines as the divergence between the two sequences increases. Recombination may be accomplished using one homology sequence on each of the donor and target molecules, thereby generating a "single-crossover" recombination product. Alternatively, two homology sequences may be placed on each of the target and donor nucleotide sequences. Recombination between two homology sequences on the donor with two homology sequences on the target generates a "double-crossover" recombination product. If the homology sequences on the donor molecule flank a sequence that is to be manipulated (e.g., a sequence of interest), the double-crossover recombination with the target molecule will result in a recombination product wherein the sequence of interest replaces a DNA sequence that was originally between the homology sequences on the target molecule. The exchange of DNA sequence between the target and donor through a double-crossover recombination event is termed "sequence replacement."

The subject event enables transgenic expression of three different herbicide tolerance proteins resulting in tolerance to combinations of herbicides that would control nearly all broadleaf and grass weeds. This multi-herbicide tolerance trait expression cassette/transgenic insert can be stacked with other herbicide tolerance traits (e.g., glyphosate resistance, glufosinate resistance, imidazolinone resistance, dicamba resistance, HPPD resistance, bromoxynil resistance, et al.), and insect resistance traits (such as Cry1F, Cry1Ab, Cry1Ac, Cry 34/45, Cry1Be, Cry1Ca, Cry1Da, Cry1Ea, Cry1Fa, vegetative insecticidal proteins ("VIPS")—including VIP3A, and the like), for example. Additionally, the herbicide tolerance proteins in the expression cassette/transgenic insert of the subject invention can serve as one or more selectable marker sto aid in selection of primary transformants of plants genetically engineered with a second gene or group of genes.

These combinations of traits give rise to novel methods of controlling weeds (and like) species, due to the newly acquired resistance or inherent tolerance to herbicides (e.g., glyphosate). Thus, novel methods for controlling weeds using Event pDAB8264.42.32.1 are within the scope of the invention.

The use of the subject transgenic traits, stacked or transformed individually into crops, provides a tool for controlling other herbicide tolerant volunteer crops that do not contain genes for conferring tolerance to phenoxy, pyridyloxy, glyphosate and/or glufosinate herbicides.

A preferred plant, or a seed, of the subject invention comprises in its genome the insert sequences, as identified herein, together with at least 20-500 or more contiguous flanking nucleotides on both sides of the insert, as described herein. Unless indicated otherwise, reference to flanking sequences refers to those identified with respect to SEQ ID NO:1 and SEQ ID NO:2. Again, the subject events include heterologous DNA inserted between the subject flanking genomic sequences immediately adjacent to the inserted DNA. All or part of these flanking sequences could be expected to be transferred to progeny that receives the inserted DNA as a result of a sexual cross of a parental line that includes the event.

The subject invention includes tissue cultures of regenerable cells of a plant of the subject invention. Also included is a plant regenerated from such tissue culture, particularly where said plant is capable of expressing all the morphological and physiological properties of an exemplified variety. Preferred plants of the subject invention have all the physiological and morphological characteristics of a plant grown from the deposited seed. This invention further comprises progeny of such seed and seed possessing the quality traits of interest.

Manipulations (such as mutation, further transfection, and further breeding) of plants or seeds, or parts thereof, may lead to the creation of what may be termed "essentially derived" varieties. The International Union for the Protection of New Varieties of Plants (UPOV) has provided the following guideline for determining if a variety has been essentially derived from a protected variety:

[A] variety shall be deemed to be essentially derived from another variety ("the initial variety") when
(i) it is predominantly derived from the initial variety, or from a variety that is itself predominantly derived from the initial variety, while retaining the expression of the essential characteristics that result from the genotype or combination of genotypes of the initial variety;

(ii) it is clearly distinguishable from the initial variety; and (iii) except for the differences which result from the act of derivation, it conforms to the initial variety in the expression of the essential characteristics that result from the genotype or combination of genotypes of the initial variety.

UPOV, Sixth Meeting with International Organizations, Geneva, Oct. 30, 1992; document prepared by the Office of the Union.

As used herein, a "line" is a group of plants that display little or no genetic variation between individuals for at least one trait. Such lines may be created by several generations of self-pollination and selection, or vegetative propagation from a single parent using tissue or cell culture techniques.

As used herein, the terms "cultivar" and "variety" are synonymous and refer to a line which is used for commercial production.

"Stability" or "stable" means that with respect to the given component, the component is maintained from generation to generation and, preferably, at least three generations at substantially the same level, e.g., preferably ±15%, more preferably ±10%, most preferably ±5%. The stability may be affected by temperature, location, stress and the time of planting. Comparison of subsequent generations under field conditions should produce the component in a similar manner.

"Commercial Utility" is defined as having good plant vigor and high fertility, such that the crop can be produced by farmers using conventional farming equipment, and the oil with the described components can be extracted from the seed using conventional crushing and extraction equipment. To be commercially useful, the yield, as measured by seed weight, oil content, and total oil produced per acre, is within 15% of the average yield of an otherwise comparable commercial soybean variety without the premium value traits grown in the same region.

"Agronomically elite" means that a line has desirable agronomic characteristics such as yield, maturity, disease resistance, and the like, in addition to the herbicide tolerance due to the subject event(s). Agronomic traits, taken individually or in any combination, as set forth in Examples, below, in a plant comprising an event of the subject invention, are within the scope of the subject invention. Any and all of these agronomic characteristics and data points can be used to identify such plants, either as a point or at either end or both ends of a range of characteristics used to define such plants.

As one skilled in the art will recognize in light of this disclosure, preferred embodiments of detection kits, for example, can include probes and/or primers directed to and/or comprising "junction sequences" or "transition sequences" (where the soybean genomic flanking sequence meets the insert sequence). For example, this includes polynucleotide probes, primers, and/or amplicons designed to identify one or both junction sequences (where the insert meets the flanking sequence), as indicated in the Table 1. One common design is to have one primer that hybridizes in the flanking region, and one primer that hybridizes in the insert. Such primers are often each about at least 15 residues in length. With this arrangement, the primers can be used to generate/amplify a detectable amplicon that indicates the presence of an event of the subject invention. These primers can be used to generate an amplicon that spans (and includes) a junction sequence as indicated above.

The primer(s) "touching down" in the flanking sequence is typically not designed to hybridize beyond about 200 bases or so beyond the junction. Thus, typical flanking primers would be designed to comprise at least 15 residues of either strand within 200 bases into the flanking sequences from the beginning of the insert. That is, primers comprising a sequence of an appropriate size from (or hybridizing to) residues within 100 to 200-500 or so bases from either or both junction sequences identified above are within the scope of the subject invention. Insert primers can likewise be designed anywhere on the insert, but residues on the insert (including the complement) within 100 to 200-500 or so bases in from the junction sequence(s) identified above, can be used, for example, non-exclusively for such primer design.

One skilled in the art will also recognize that primers and probes can be designed to hybridize, under a range of standard hybridization and/or PCR conditions, to segments of sequences exemplified herein (or complements thereof), wherein the primer or probe is not perfectly complementary to the exemplified sequence. That is, some degree of mismatch can be tolerated. For an approximately 20 nucleotide primer, for example, typically one or two or so nucleotides do not need to bind with the opposite strand if the mismatched base is internal or on the end of the primer that is opposite the amplicon. Various appropriate hybridization conditions are provided below. Synthetic nucleotide analogs, such as inosine, can also be used in probes. Peptide nucleic acid (PNA) probes, as well as DNA and RNA probes, can also be used. What is important is that such probes and primers are diagnostic for (able to uniquely identify and distinguish) the presence of an event of the subject invention.

It should be noted that errors in PCR amplification can occur which might result in minor sequencing errors, for example. That is, unless otherwise indicated, the sequences listed herein were determined by generating long amplicons from soybean genomic DNAs, and then cloning and sequencing the amplicons. It is not unusual to find slight differences and minor discrepancies in sequences generated and determined in this manner, given the many rounds of amplification that are necessary to generate enough amplicon for sequencing from genomic DNAs. One skilled in the art should recognize and be put on notice that any adjustments needed due to these types of common sequencing errors or discrepancies are within the scope of the subject invention.

It should also be noted that it is not uncommon for some genomic sequence to be deleted, for example, when a sequence is inserted during the creation of an event. Thus, some differences can also appear between the subject flanking sequences and genomic sequences listed in GENBANK, for example.

Components of the "insert" are illustrated in the Figures and are discussed in more detail below in the Examples. The DNA polynucleotide sequences of these components, or fragments thereof, can be used as DNA primers or probes in the methods of the present invention.

In some embodiments of the invention, compositions and methods are provided for detecting the presence of the transgene/genomic insertion region, in plants and seeds and the like, from a soybean plant. DNA sequences are provided that comprise the subject transgene/genomic insertion region junction sequence provided herein, segments comprising a junction sequence identified herein, and complements of any such exemplified sequences and any segments thereof. The insertion region junction sequence spans the junction between heterologous DNA inserted into the genome and the DNA from the soybean cell flanking the insertion site. Such sequences can be diagnostic for the given event.

Based on these insert and border sequences, event-specific primers can be generated. PCR analysis demonstrated that soybean lines of the subject invention can be identified in different soybean genotypes by analysis of the PCR amplicons generated with these event-specific primer sets. These and other related procedures can be used to uniquely identify these soybean lines. Thus, PCR amplicons derived from such primer pairs are unique and can be used to identify these soybean lines.

In some embodiments, DNA sequences that comprise a contiguous fragment of the novel transgene/genomic insertion region are an aspect of this invention. Included are DNA sequences that comprise a sufficient length of polynucleotides of transgene insert sequence and a sufficient length of polynucleotides of soybean genomic sequence from one or more of the aforementioned soybean plants and/or sequences that are useful as primer sequences for the production of an amplicon product diagnostic for one or more of these soybean plants.

Related embodiments pertain to DNA sequences that comprise at least 2, 3, 4, 5, 6, 7, 8, 9, 10, 11, 12, 13, 14, 15, 16, 17, 18, 19, 20, 21, 22, 23, 24, 25, or more contiguous nucleotides of a transgene portion of a DNA sequence identified herein, or complements thereof, and a similar length of flanking soybean DNA sequence (such as SEQ ID NO:1 and SEQ ID NO:2 and segments thereof) from these sequences, or complements thereof. Such sequences are useful as DNA primers in DNA amplification methods. The amplicons produced using these primers are diagnostic for any of the soybean events referred to herein. Therefore, the invention also includes the amplicons produced by such DNA primers and homologous primers.

This invention also includes methods of detecting the presence of DNA, in a sample, that corresponds to the soybean event referred to herein. Such methods can comprise: (a) contacting the sample comprising DNA with a primer set that, when used in a nucleic acid amplification reaction with DNA from at least one of these soybean events, produces an amplicon that is diagnostic for said event(s); (b) performing a nucleic acid amplification reaction, thereby producing the amplicon; and (c) detecting the amplicon.

Further detection methods of the subject invention include a method of detecting the presence of a DNA, in a sample, corresponding to said event, wherein said method comprises: (a) contacting the sample comprising DNA with a probe that hybridizes under stringent hybridization conditions with DNA from at least one of said soybean events and which does not hybridize under the stringent hybridization conditions with a control soybean plant (non-event-of-interest DNA); (b) subjecting the sample and probe to stringent hybridization conditions; and (c) detecting hybridization of the probe to the DNA.

In still further embodiments, the subject invention includes methods of producing a soybean plant comprising Event pDAB8264.42.32.1, wherein said method comprises the steps of: (a) sexually crossing a first parental soybean line (comprising an expression cassettes of the present invention, which confers said herbicide resistance trait to plants of said line) and a second parental soybean line (that lacks this herbicide tolerance trait) thereby producing a plurality of progeny plants; and (b) selecting a progeny plant by the use of molecular markers. Such methods may optionally comprise the further step of back-crossing the progeny plant to the second parental soybean line to producing a true-breeding soybean plant that comprises said herbicide tolerance trait.

According to another aspect of the invention, methods of determining the zygosity of progeny of a cross with said event is provided. Said methods can comprise contacting a sample, comprising soybean DNA, with a primer set of the subject invention. Said primers, when used in a nucleic-acid amplification reaction with genomic DNA from at least one of said soybean events, produces a first amplicon that is diagnostic for at least one of said soybean events. Such methods further comprise performing a nucleic acid amplification reaction, thereby producing the first amplicon; detecting the first amplicon; and contacting the sample comprising soybean DNA with said primer set (said primer set, when used in a nucleic-acid amplification reaction with genomic DNA from soybean plants, produces a second amplicon comprising the native soybean genomic DNA homologous to the soybean genomic region; and performing a nucleic acid amplification reaction, thereby producing the second amplicon. The methods further comprise detecting the second amplicon, and comparing the first and second amplicons in a sample, wherein the presence of both amplicons indicates that the sample is heterozygous for the transgene insertion.

DNA detection kits can be developed using the compositions disclosed herein and methods well known in the art of DNA detection. The kits are useful for identification of the subject soybean event DNA in a sample and can be applied to methods for breeding soybean plants containing this DNA. The kits contain DNA sequences homologous or complementary to the amplicons, for example, disclosed herein, or to DNA sequences homologous or complementary to DNA contained in the transgene genetic elements of the subject events. These DNA sequences can be used in DNA amplification reactions or as probes in a DNA hybridization method. The kits may also contain the reagents and materials necessary for the performance of the detection method.

A "probe" is an isolated nucleic acid molecule to which is attached a conventional detectable label or reporter molecule (such as a radioactive isotope, ligand, chemiluminescent agent, or enzyme). Such a probe is complementary to a strand of a target nucleic acid, in the case of the present invention, to a strand of genomic DNA from one of said soybean events, whether from a soybean plant or from a sample that includes DNA from the event. Probes according to the present invention include not only deoxyribonucleic or ribonucleic acids but also polyamides and other probe materials that bind specifically to a target DNA sequence and can be used to detect the presence of that target DNA sequence. An "isolated" polynucleotide connotes that the polynucleotide is in a non-natural state—operably linked to a heterologous promoter, for example. A "purified" protein likewise connotes that the protein is in a non-natural state.

"Primers" are isolated/synthesized nucleic acids that are annealed to a complementary target DNA strand by nucleic acid hybridization to form a hybrid between the primer and the target DNA strand, and then extended along the target DNA strand by a polymerase, e.g., a DNA polymerase. Primer pairs of the present invention refer to their use for amplification of a target nucleic acid sequence, e.g., by the polymerase chain reaction (PCR) or other conventional nucleic-acid amplification methods.

Probes and primers are generally 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, or 500 polynucleotides or more in length. Such probes and primers hybridize specifically to a target sequence under high stringency hybridization conditions. Preferably, probes and primers according to the present invention have complete sequence similarity with the target sequence, although probes differing from the target sequence and that retain the ability to hybridize to target sequences maybe designed by conventional methods.

Methods for preparing and using probes and primers are described, for example, in Molecular Cloning: A Laboratory Manual, 2nd ed., vol. 1-3, ed. Sambrook et al., Cold Spring Harbor Laboratory Press, Cold Spring Harbor, N.Y., 1989. PCR-primer pairs can be derived from a known sequence, for example, by using computer programs intended for that purpose.

Primers and probes based on the flanking DNA and insert sequences disclosed herein can be used to confirm (and, if necessary, to correct) the disclosed sequences by conventional methods, e.g., by re-cloning and sequencing such sequences.

The nucleic acid probes and primers of the present invention hybridize under stringent conditions to a target DNA sequence. Any conventional nucleic acid hybridization or amplification method can be used to identify the presence of DNA from a transgenic event in a sample. Nucleic acid molecules or fragments thereof are capable of specifically hybridizing to other nucleic acid molecules under certain circumstances. As used herein, two nucleic acid molecules are said to be capable of specifically hybridizing to one another if the two molecules are capable of forming an anti-parallel, double-stranded nucleic acid structure. A nucleic acid molecule is said to be the "complement" of another nucleic acid molecule if they exhibit complete complementarity. As used herein, molecules are said to exhibit "complete complementarity" when every nucleotide of one of the molecules is complementary to a nucleotide of the other. Two molecules are said to be "minimally complementary" if they can hybridize to one another with sufficient stability to permit them to remain annealed to one another under at least conventional "low-stringency" conditions. Similarly, the molecules are said to be "complementary" if they can hybridize to one another with sufficient stability to permit them to remain annealed to one another under conventional "high-stringency" conditions. Conventional stringency conditions are described by Sambrook et al., 1989. Departures from complete complementarity are therefore permissible, as long as such departures do not completely preclude the capacity of the molecules to form a double-stranded structure. In order for a nucleic acid molecule to serve as a primer or probe it need only be sufficiently complementary in sequence to be able to form a stable double-stranded structure under the particular solvent and salt concentrations employed.

As used herein, a substantially homologous sequence is a nucleic acid sequence that will specifically hybridize to the complement of the nucleic acid sequence to which it is being compared under high stringency conditions. The term "stringent conditions" is functionally defined with regard to the hybridization of a nucleic-acid probe to a target nucleic acid (i.e., to a particular nucleic-acid sequence of interest) by the specific hybridization procedure discussed in Sambrook et al., 1989, at 9.52-9.55. See also, Sambrook et al., 1989 at 9.47-9.52 and 9.56-9.58. Accordingly, the nucleotide sequences of the invention may be used for their ability to selectively form duplex molecules with complementary stretches of DNA fragments.

Depending on the application envisioned, one can use varying conditions of hybridization to achieve varying degrees of selectivity of probe towards target sequence. For applications requiring high selectivity, one will typically employ relatively stringent conditions to form the hybrids, e.g., with regards to endpoint TAQMAN and real-time PCR applications, one will select 1.5 mM to about 4.0 mM MgCl2 at temperature of about 60° C. to about 75° C. and may vary hold times, as described herein, for increasing stringency. For other hybridization techniques one will typically employ relatively low salt and/or high temperature conditions, such as provided by about 0.02 M to about 0.15 M NaCl at temperatures of about 50° C. to about 70° C. Stringent conditions, for example, could involve washing the hybridization filter at least twice with high-stringency wash buffer (0.2×SSC, 0.1% SDS, 65° C.). Appropriate stringency conditions which promote DNA hybridization, for example, 6.0× sodium chloride/sodium citrate (SSC) at about 45° C., followed by a wash of 2.0×SSC at 50° C. are known to those skilled in the art. For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C. Both temperature and salt may be varied, or either the temperature or the salt concentration may be held constant while the other variable is changed. Such selective conditions tolerate little, if any, mismatch between the probe and the template or target strand. Detection of DNA sequences via hybridization is well-known to those of skill in the art, and the teachings of U.S. Pat. Nos. 4,965,188 and 5,176,995 are exemplary of the methods of hybridization analyses.

In a particularly preferred embodiment, a nucleic acid of the present invention will specifically hybridize to one or more of the primers (or amplicons or other sequences) exemplified or suggested herein, including complements and fragments thereof, under high stringency conditions. In one aspect of the present invention, a marker nucleic acid molecule of the present invention has the nucleic acid sequence as set forth herein in one of the exemplified sequences, or complements and/or fragments thereof.

In another aspect of the present invention, a marker nucleic acid molecule of the present invention shares between 80% and 100% or 90% and 100% sequence identity with such nucleic acid sequences. In a further aspect of the present invention, a marker nucleic acid molecule of the present invention shares between 95% and 100% sequence identity with such sequence. Such sequences may be used as markers in plant breeding methods to identify the progeny of genetic crosses. The hybridization of the probe to the target DNA molecule can be detected by any number of methods known to those skilled in the art, these can include, but are not limited to, fluorescent tags, radioactive tags, antibody based tags, and chemiluminescent tags.

Regarding the amplification of a target nucleic acid sequence (e.g., by PCR) using a particular amplification primer pair, "stringent conditions" are conditions that permit the primer pair to hybridize only to the target nucleic-acid sequence to which a primer having the corresponding wild-type sequence (or its complement) would bind and preferably to produce a unique amplification product, the amplicon.

The term "specific for (a target sequence)" indicates that a probe or primer hybridizes under stringent hybridization conditions only to the target sequence in a sample comprising the target sequence.

As used herein, "amplified DNA" or "amplicon" refers to the product of nucleic-acid amplification of a target nucleic acid sequence that is part of a nucleic acid template. For example, to determine whether the soybean plant resulting from a sexual cross contains transgenic event genomic DNA from the soybean plant of the present invention, DNA extracted from a soybean plant tissue sample may be subjected to nucleic acid amplification method using a primer pair that includes a primer derived from flanking sequence in the genome of the plant adjacent to the insertion site of inserted heterologous DNA, and a second primer derived from the inserted heterologous DNA to produce an amplicon that is diagnostic for the presence of the event DNA. The amplicon is of a length and has a sequence that is also diagnostic for the event. The amplicon may range in length from the combined length of the primer pairs plus one nucleotide base pair, and/or the combined length of the primer pairs plus about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, or 500, 750, 1000, 1250, 1500, 1750, 2000, or more nucleotide base pairs (plus or minus any of the increments listed above). Alternatively, a primer pair can be derived from flanking sequence on both sides of the inserted DNA so as to produce an amplicon that includes the entire insert nucleotide sequence. A member of a primer pair derived from the plant genomic sequence may be located a distance from the inserted DNA sequence. This distance can range from one nucleotide base pair up to about twenty thousand nucleotide base pairs. The use of the term "amplicon" specifically excludes primer dimers that may be formed in the DNA thermal amplification reaction.

Nucleic-acid amplification can be accomplished by any of the various nucleic-acid amplification methods known in the art, including the polymerase chain reaction (PCR). A variety of amplification methods are known in the art and are described, inter alia, in U.S. Pat. No. 4,683,195 and U.S. Pat. No. 4,683,202. PCR amplification methods have been developed to amplify up to 22 kb of genomic DNA. These methods as well as other methods known in the art of DNA amplification may be used in the practice of the present invention. The sequence of the heterologous transgene DNA insert or flanking genomic sequence from a subject soybean event can be verified (and corrected if necessary) by amplifying such sequences from the event using primers derived from the sequences provided herein followed by standard DNA sequencing of the PCR amplicon or of the cloned DNA.

The amplicon produced by these methods may be detected by a plurality of techniques. Agarose gel electrophoresis and staining with ethidium bromide is a common well known method of detecting DNA amplicons. Another such method is Genetic Bit Analysis where an DNA oligonucleotide is designed which overlaps both the adjacent flanking genomic DNA sequence and the inserted DNA sequence. The oligonucleotide is immobilized in wells of a microwell plate. Following PCR of the region of interest (using one primer in the inserted sequence and one in the adjacent flanking genomic sequence), a single-stranded PCR product can be hybridized to the immobilized oligonucleotide and serve as a template for a single base extension reaction using a DNA polymerase and labeled ddNTPs specific for the expected next base. Readout may be fluorescent or ELISA-based. A signal indicates presence of the insert/flanking sequence due to successful amplification, hybridization, and single base extension.

Another method is the Pyrosequencing technique as described by Winge (Innov. Pharma. Tech. 00:18-24, 2000). In this method an oligonucleotide is designed that overlaps the adjacent genomic DNA and insert DNA junction. The oligonucleotide is hybridized to single-stranded PCR product from the region of interest (one primer in the inserted sequence and one in the flanking genomic sequence) and incubated in the presence of a DNA polymerase, ATP, sulfurylase, luciferase, apyrase, adenosine 5' phosphosulfate and luciferin. DNTPs are added individually and the incorporation results in a light signal that is measured. A light signal indicates the presence of the transgene insert/flanking sequence due to successful amplification, hybridization, and single or multi-base extension.

Fluorescence Polarization is another method that can be used to detect an amplicon of the present invention. Following this method, an oligonucleotide is designed which overlaps the genomic flanking and inserted DNA junction. The oligonucleotide is hybridized to single-stranded PCR product from the region of interest (one primer in the inserted DNA and one in the flanking genomic DNA sequence) and incubated in the presence of a DNA polymerase and a fluorescent-labeled ddNTP. Single base extension results in incorporation of the ddNTP. Incorporation can be measured as a change in polarization using a fluorometer. A change in polarization indicates the presence of the transgene insert/flanking sequence due to successful amplification, hybridization, and single base extension.

TAQMAN (PE Applied Biosystems, Foster City, Calif.) is a method of detecting and quantifying the presence of a DNA sequence. Briefly, a FRET oligonucleotide probe is designed that overlaps the genomic flanking and insert DNA junction. The FRET probe and PCR primers (one primer in the insert DNA sequence and one in the flanking genomic sequence) are cycled in the presence of a thermostable polymerase and dNTPs. During specific amplification, Taq DNA polymerase cleans and releases the fluorescent moiety away from the quenching moiety on the FRET probe. A fluorescent signal indicates the presence of the flanking/transgene insert sequence due to successful amplification and hybridization.

Molecular Beacons have been described for use in sequence detection. Briefly, a FRET oligonucleotide probe is designed that overlaps the flanking genomic and insert DNA junction. The unique structure of the FRET probe results in it containing secondary structure that keeps the fluorescent and quenching moieties in close proximity. The FRET probe and PCR primers (one primer in the insert DNA sequence and one in the flanking genomic sequence) are cycled in the presence of a thermostable polymerase and dNTPs. Following successful PCR amplification, hybridization of the FRET probe to the target sequence results in the removal of the probe secondary structure and spatial separation of the fluorescent and quenching moieties. A fluorescent signal results. A fluorescent signal indicates the presence of the flanking genomic/transgene insert sequence due to successful amplification and hybridization.

Having disclosed a location in the soybean genome that is excellent for an insertion, the subject invention also includes a soybean seed and/or a soybean plant comprising at least one non-aad12/pat/2mepsps coding sequence in or around the general vicinity of this genomic location. One option is to substitute a different insert in place of the insert exemplified herein. In these general regards, targeted homologous recombination, for example, can be used according to the subject invention. This type of technology is the subject of, for example, WO 03/080809 A2 and the corresponding published U.S. application (U.S. 2003/0232410). Thus, the subject invention includes plants and plant cells comprising a heterologous insert (in place of or with multi-copies of the exemplified insert), flanked by all or a recognizable part of the flanking sequences identified herein as SEQ ID NO:1 and SEQ ID NO:2. An additional copy (or additional copies) of the exemplified insert or any of its components could also be targeted for insertion in this/these manner(s).

All patents, patent applications, provisional applications, and publications referred to or cited herein are incorporated by reference in their entirety to the extent they are not inconsistent with the explicit teachings of this specification.

The following examples are included to illustrate procedures for practicing the invention and to demonstrate certain preferred embodiments of the invention. These examples should not be construed as limiting. It should be appreciated by those of skill in the art that the techniques disclosed in the following examples represent specific approaches used to illustrate preferred modes for its practice. However, those of skill in the art should, in light of the present disclosure, appreciate that many changes can be made in these specific embodiments while still obtaining like or similar results without departing from the spirit and scope of the invention. Unless otherwise indicated, all percentages are by weight and all solvent mixture proportions are by volume unless otherwise noted.

The following abbreviations are used unless otherwise indicated.

bp base pair
° C. degrees Celsius
DNA deoxyribonucleic acid
DIG digoxigenin
EDTA ethylenediaminetetraacetic acid
kb kilobase
μg microgram
μL microliter
mL milliliter
M molar mass
OLP overlapping probe
PCR polymerase chain reaction
PTU plant transcription unit
SDS sodium dodecyl sulfate
SOP standard operating procedure
SSC a buffer solution containing a mixture of sodium chloride and sodium citrate, pH 7.0
TBE a buffer solution containing a mixture of Tris base, boric acid and EDTA, pH 8.3
V volts

EXAMPLES

Example 1

Transformation and Selection of the 2mEPSPS and AAD-12 Soybean Event pDAB8264.42.32.1

Transgenic soybean (*Glycine max*) containing the Soybean Event pDAB8264.42.32.1 was generated through *Agrobacterium*-mediated transformation of soybean cotyledonary node explants. The disarmed *Agrobacterium* strain EHA101 (Hood et al., 1993), carrying the binary vector pDAB8264 (FIG. 1) containing the selectable marker, pat v6, and the genes of interest, aad-12 v1 and 2mEPSPS v1, within the T-strand DNA region, was used to initiate transformation.

*Agrobacterium*-mediated transformation was carried out using a modified procedure of Zeng et al. (2004). Briefly, soybean seeds (cv Maverick) were germinated on basal media and cotyledonary nodes were isolated and infected with *Agrobacterium*. Shoot initiation, shoot elongation, and rooting media were supplemented with cefotaxime, timentin and vancomycin for removal of *Agrobacterium*. Glufosinate selection was employed to inhibit the growth of non-transformed shoots. Selected shoots were transferred to rooting medium for root development and then transferred to soil mix for acclimatization of plantlets.

Terminal leaflets of selected plantlets were leaf painted with glufosinate to screen for putative transformants. The screened plantlets were transferred to the greenhouse, allowed to acclimate and then leaf-painted with glufosinate to reconfirm tolerance and deemed to be putative transformants. The screened plants were sampled and molecular analyses for the confirmation of the selectable marker gene and/or the gene of interest were carried out. $T_0$ plants were allowed to self fertilize in the greenhouse to give rise to $T_1$ seed.

This event, Soybean Event pDAB8264.42.32.1, was generated from an independent transformed isolate. The $T_1$ plants were backcrossed and introgressed into elite varieties over subsequent generations. The event was selected based on its unique characteristics such as single insertion site, normal Mendelian segregation, stable expression, and a superior combination of efficacy, including herbicide tolerance and agronomic performance. The following examples contain the data which were used to characterize Soybean Event pDAB8264.42.32.1.

Example 2

Characterization of Protein Expression in Soybean Event pDAB8264.42.32.1

The biochemical properties of the recombinant AAD-12, 2mEPSPS and PAT proteins expressed in Soybean Event pDAB8264.42.32.1 were characterized. Quantitative enzyme-linked immunosorbent assay (ELISA) is a biochemical assay known within the art that can be used to characterize the biochemical properties of the proteins and confirm expression of these proteins in the soybean events.

Example 2.1

Expression of the PAT Protein in Plant Tissues

Levels of PAT protein were determined in Soybean Event pDAB8264.42.32.1. The soluble, extractable PAT protein was measured using a quantitative enzyme-linked immunosorbent assay (ELISA) method from soybean leaf tissue.

Samples of soybean tissues were isolated from the test plants and prepared for expression analysis. The PAT protein was extracted from soybean plant tissues with a phosphate buffered saline solution containing the detergent Tween-20 (PBST) containing 1% Polyvinylpyrrolidone (PVP). The plant tissue was centrifuged; the aqueous supernatant was collected, diluted with appropriate buffer as necessary, and analyzed using a PAT ELISA kit in a sandwich format. The kit was used following the manufacturer's suggested protocol (Envirologix, Portland, Me.). This assay measured the expressed PAT protein.

Detection analysis was performed to investigate the expression stability and inheritability both vertically (between generations) and horizontally (between lineages within a generation) in Soybean Event pDAB8264.42.32.1. From $T_3$ to $T_5$ generations of Soybean Event pDAB8264.42.32.1, expression was stable and consistent across all lineages.

Example 2.2

Expression of the AAD-12 and 2mEPSPS Protein in Plant Tissues

Levels of AAD-12 and 2mEPSPS proteins were determined in Soybean Event pDAB8264.42.32 .1. The soluble, extractable proteins were measured using a quantitative enzyme-linked immunosorbent assay (ELISA) method from soybean leaf tissue.

Samples of soybean tissues were isolated from the test plants and prepared for expression analysis. The AAD-12 and 2mEPSPS proteins were extracted from soybean plant tissues with a phosphate buffered saline solution containing the detergent Tween-20 (PBST) containing 1% Bovine Serum Albumin (BSA). The plant tissue was centrifuged; the aqueous supernatant was collected, diluted with appropriate buffer as necessary, and analyzed using the AAD-12 and GA21 ELISA kits, respectively, in a sandwich format. The kit was used following the manufacturer's suggested protocol (AAD-12: catalog number 20-0161, Beacon Analytical Systems, Inc., Saco, Me.; 2mEPSPS: catalog #7020100, Strategic Diagnostics, Newark, Del.). From $T_4$ to $T_6$ generations of Soybean Event pDAB8264.42.32.1, AAD-12 and 2mEPSPS expression was stable and consistent across all lineages.

Example 2.3

Expression Efficacy Studies

Field expression level studies at V3 plant stage were performed on Soybean Event pDAB8264.42.32.1. Expression level studies were performed on all the sprayed treatments as well as for the unsprayed plots. These experiments were completed using the protocols described previously. Expression values were similar for all the sprayed treatments as well as for the plots sprayed and unsprayed with different combinations of herbicides (Table 2). No significant injury was observed on the plants at any point of the study.

TABLE 2

Herbicide treatment and concentrations of herbicides used in protein expression studies.

| Treat Number | Treatment Type |
| --- | --- |
| 1 | No Spray |
| 2 | Glufosinate, 822 g ae/ha |
| 3 | 2,4-D 2240 g ae/ha |
| 4 | Glyphosate 2240 g ae/ha |
| 5 | Glyphosate + 2,4-D each at 1120 g ae/ha |
| 6 | Glyphosate + 2,4-D each at 2240 g ae/ha |

Example 3

Cloning and Characterization of DNA Sequence in the Insert and the Flanking Border Regions of Soybean Event pDAB8264.42.32.1

To characterize and describe the genomic insertion site, the sequence of the flanking genomic T-DNA border regions of Soybean Event pDAB8264.42.32.1 were determined. Genomic sequence of Soybean Event pDAB8264.42.32.1 was confirmed, comprising 1,246 bp of 5' flanking border sequence (SEQ ID NO:1), and 504 bp of 3' flanking border sequence (SEQ ID NO:2). PCR amplification based on the Soybean Event pDAB8264.42.32.1 border sequences validated that the border regions were of soybean origin and that the junction regions are unique sequences for Soybean Event pDAB8264.42.32.1. The junction regions can be used for event-specific identification of Soybean Event pDAB8264.42.32.1. In addition, the T-strand insertion site was characterized by amplifying a genomic fragment corresponding to the region of the identified flanking border sequences from the genome of wild type, untransformed soybean. Comparison of Soybean Event pDAB8264.42.32.1 with the wild type genomic sequence revealed about 38 by deletion from the original locus. Overall, the characterization of the insert and border sequence of Soybean Event pDAB8264.42.32.1 indicated that an intact copy of the T-strand was present in the soybean genome.

TABLE 3

List of primers and their sequences used in the confirmation of soybean genomic DNA in Soybean Event pDAB8264.42.32.1.

| SEQ ID NO: | Primer Name | Size (bp) | Sequence (5'to 3') | Purpose |
|---|---|---|---|---|
| SEQ ID NO: 3 | 4232-WF1 | 25 | GATTTCTGCATCATTT ATGACCAGG | confirmation of 5' border genomic DNA, used with ED_v1_C1 |
| SEQ ID NO: 4 | 4232-WF3 | 25 | TGTAAATGCTTCACA ACATGAGTCA | confirmation of 5' border genomic DNA, used with ED_v1_C |
| SEQ ID NO: 5 | 4232-WF4 | 25 | ATGTAAATGCTTCAC AACATGAGTC | confirmation of 5' border genomic DNA, used with ED_v1_C1 |
| SEQ ID NO: 6 | 4232-WR1 | 26 | TTTCTACAGCTAGCA CAACAAGACCT | confirmation of 3' border genomic DNA, used with PAT_11 |
| SEQ ID NO: 7 | 4232-WR2 | 28 | CGTATCTGATACTAA CCAGTTCGAATTC | confirmation of 3' border genomic DNA, used with PAT_11 |
| SEQ ID NO: 8 | 4232-WR3 | 25 | AAGAGATACGAAGCG TTTCGCTATT | confirmation of 3' border genomic DNA, used with PAT_11 |
| SEQ ID NO: 9 | 4232-WR4 | 26 | AAACACTACTACCAG AAACCAAGTGT | confirmation of 3' border genomic DNA, used with PAT_11 |
| SEQ ID NO: 10 | ED_v1_C1 | 26 | GAGTAAAGGAGACCG AGAGGATGGTT | confirmation of 5' border genomic 4232-WF1, 4232-WF3, or 4232-WF4, |
| SEQ ID NO: 11 | PAT_11 | 24 | ACAGAGCCACAAACA CCACAAGAG | confirmation of 3' border genomic DNA, used with 4232-WR1, 4232-WR2, 4232-WR3, or 4232-WR4 |

TABLE 4

Conditions for standard PCR amplification of the border regions and event-specific sequences in Soybean Event pDAB8264.42.32.1

| Target Sequence | Primer Set | PCR Mixture | Pre-denature (° C./min) | Denature (° C./sec.) | Anneal (° C./sec.) | Extension (° C./min:sec) | Final Extension (° C./min) |
|---|---|---|---|---|---|---|---|
| 5' border | 4232-WF1/ED_v1_C1 | D | 95/3 | 98/10 | 63/30 32 cycles | 68/4:00 | 72/10 |
| 5' border | 4232-WF3/ED_v1_C1 | D | 95/3 | 98/10 | 63/30 32 cycles | 68/4:00 | 72/10 |
| 5' border | 4232-WF4/ED_v1_C1 | D | 95/3 | 98/10 | 63/30 32 cycles | 68/4:00 | 72/10 |
| 3' border | 4232-WR1/PAT_11 | D | 95/3 | 98/10 | 63/30 32 cycles | 68/4:00 | 72/10 |
| 3' border | 4232-WR2/PAT_11 | D | 95/3 | 98/10 | 63/30 32 cycles | 68/4:00 | 72/10 |
| 3' border | 4232-WR3/PAT_11 | D | 95/3 | 98/10 | 63/30 32 cycles | 68/4:00 | 72/10 |
| 3' border | 4232-WR4/PAT_11 | D | 95/3 | 98/10 | 63/30 32 cycles | 68/4:00 | 72/10 |
| Across the insert locus | 4232-WF1/4232-WR1 | D | 95/3 | 98/10 | 63/30 32 cycles | 68/4:00 | 72/10 |
| Across the insert locus | 4232-WF1/4232-WR2 | D | 95/3 | 98/10 | 63/30 32 cycles | 68/4:00 | 72/10 |

TABLE 5

PCR mixture for standard PCR amplification of the border regions and event specific sequences in Soybean Event pDAB8264.42.32.1

| Reagent | 1 x reaction (μL) | Reagent | 1 x reaction (μL) |
|---|---|---|---|
| PCR Mixture A | | PCR Mixture B | |
| H20 | 0.8 | H20 | 14.6 |
| AccPrime pfx SuperMix | 20 | 10X LA Taq buffer | 2 |
| — | — | MgCl2 (25 mM) | 0.6 |
| — | — | dNTP (2.5 μM) | 1.6 |
| 10 μM primer | 0.2 | 10 μM primer | 0.1 |
| gDNA digestion | 1 | gDNA digestion | 1 |
| — | — | LA Taq (5 U/μL) | 0.1 |
| rxn vol: | 22 | rxn vol: | 20 |
| PCR Mixture C | | PCR Mixture D | |
| H20 | 28 | H20 | 11.6 |
| 10X PCR buffer II (Mg-plus) | 5 | 10X PCR buffer II (Mg-plus) | 2 |
| MgCl₂[25 mM] | 1.5 | MgCl₂[25 mM] | 0.6 |
| dNTP[2.5 mM] | 8 | dNTP[2.5 mM] | 3.2 |
| Adaptor PCR primer (10 μM) | 1 | primer1 (10 μM) | 0.4 |
| GOI nested primer (10 μM) | 1 | primer2 (10 μM) | 0.4 |
| DNA binded Beads | 5 | DNA Template | 0.2 |
| LA Taq (5 U/μL) | 0.5 | LA Taq (5 U/μL) | 1.6 |
| rxn vol: | 50 | rxn vol: | 20 |

Example 3.1

Confirmation of Soybean Genomic Sequences

The 5' and 3' flanking borders aligned to a *Glycine max* whole genome shotgun sequence from chromosome 15, indicating that the transgene of Soybean Event pDAB8264.42.32.1 was inserted in soybean genome chromosome 15. To confirm the insertion site of Soybean Event pDAB8264.42.32.1 transgene from the soybean genome, PCR was carried out with different pairs of primers (FIG. 2, Table 3, Table 4 and Table 5). Genomic DNA from Soybean Event pDAB8264.42.32.1 and other transgenic or non-transgenic soybean lines was used as a template. Thus, to confirm if the 5' border sequences are correct 2mEPSPS v1 specific primers, for example ED_v1_C1, and primers designed according to the cloned 5' end border sequence and/or its alignment sequence on soybean genome chromosome 15, designated 4232-WF1, 4232-WF3 and 4232-WF4, were used for amplifying the DNA segment that spans the 2mEPSPS v1 gene to 5' end border sequence. Similarly, for confirmation of the cloned 3' end border sequence, a pat specific primer, for example PAT_11, and four primers designed according to the cloned 3' end border sequence and/or its alignment sequence on soybean genome chromosome 15, designated 4232-WR1, 4232-WR2, 4232-WR3 and 4232-WR4, were used for amplifying DNA segments that span the pat gene to the 3' end border sequence. DNA fragments with predicted sizes were amplified only from the genomic DNA of Soybean Event pDAB8264.42.32.1 with each primer pair, one primer located on the flanking border of Soybean Event pDAB8264.42.32.1 and one transgene specific primer, but not from DNA samples from other transgenic soybean lines or non-transgenic control. The results indicate that the cloned 5' and 3' border sequences are the flanking border sequences of the T-strand insert for Soybean Event pDAB8264.42.32.1.

Figure 3:
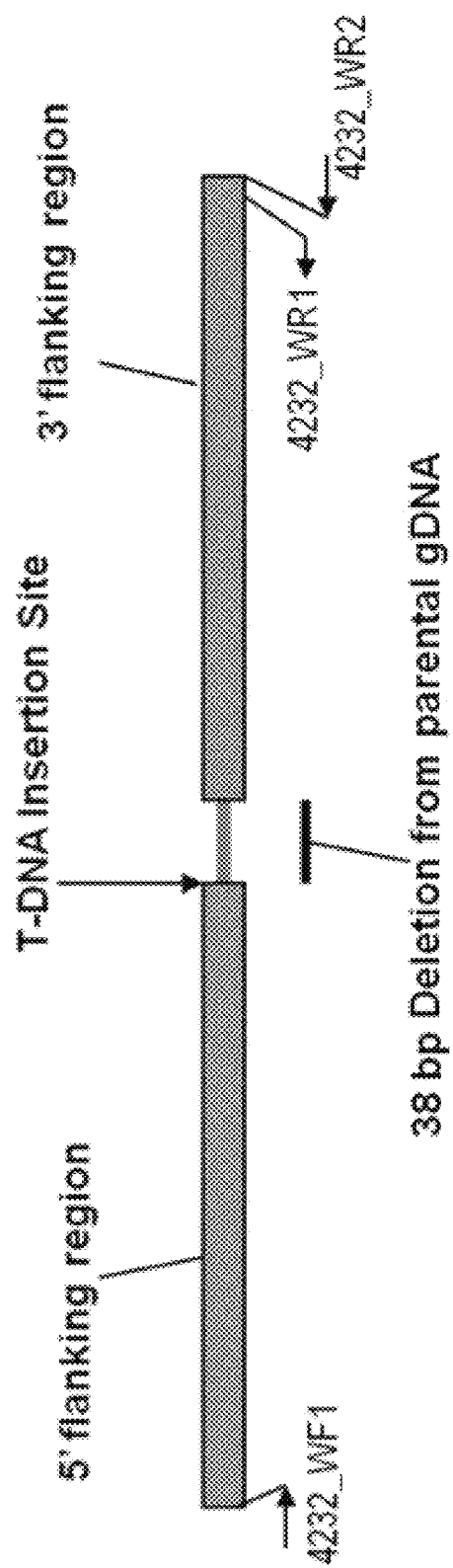
FIG. 3: is a schematic diagram depicting primer locations for confirming the untransformed and genomic DNA where soybean event pDAB8264.42.32.1.

To further confirm the genomic sited of the T-strand DNA insertion in the soybean genome, a PCR amplification spanning the soybean border sequences was completed on genomic DNA which did not contain the T-strand insert for Soybean Event pDAB8264.42.32.1. One primer designed according to the 5' end border sequence, 4232-WF1, and two primers for the 3' end border sequence, 4232-WR1 and 4232-WR2, were used to amplify the 5' end border sequence and the 3' border sequence DNA segments where the pDAB8264 T-strand integrated. As expected, PCR amplification with the primer pair of 4232-WF1 and 4232-WR1 amplified an approximately 2.4 kb DNA fragment from the genomic DNA of the non-transgenic soybean controls and other soybean transgenic lines but not from Soybean Event pDAB8264.42.32.1. Similarly, PCR reactions completed with the primer pair of 4232-WF1 and 4232-WR2 produced an approximately 2.5 kb DNA fragment from the genomic DNA of the non-transgenic soybean controls and other soybean transgenic lines but not from Soybean Event pDAB8264.42.32.1. Aligning the identified 5' and 3' border sequences of Soybean Event pDAB8264.42.32.1 with a *Glycine max* whole genome shotgun sequence from chromosome 15 revealed a 38 bp deletion from the original genomic locus. (FIG. 3). These results demonstrated that the transgene of Soybean Event pDAB8264.42.32.1 was inserted into the site of soybean genome chromosome 15.

Example 4

Soybean Event pDAB8264.42.32.1 Characterization via Southern Blot

Southern blot analysis was used to establish the integration pattern of Soybean Event pDAB8264.42.32.1. These experiments generated data which demonstrated the integration and integrity of the aad-12 v1 and 2mEPSPS v1 transgenes within the soybean genome. Soybean Event pDAB8264.42.32.1 was characterized as a full length, simple integration event containing a single copy of the aad-12 v1 and 2mEPSPS v1 PTU from plasmid pDAB8264.

Southern blot data suggested that a full length T-strand fragment inserted into the genome of Soybean Event pDAB8264.42.32.1. Detailed Southern blot analysis was conducted using a probe specific to the aad-12 v1 and 2mEPSPS v1 gene, contained in the T-strand integration region of pDAB8264, and descriptive restriction enzymes that have cleavage sites located within the plasmid and produce hybridizing fragments internal to the plasmid or fragments that span the junction of the plasmid with soybean genomic DNA (border fragments). The molecular weights indicated from the Southern hybridization for the combination of the restriction enzyme and the probe were unique for the event, and established its identification patterns. These analyses also showed that the plasmid fragment had been inserted into soybean genomic DNA without rearrangements of the aad-12 v1 and 2mEPSPS v1 PTU.

Example 4.1

Soybean Leaf Sample Collection and Genomic DNA (gDNA) Isolation

Genomic DNA was extracted from leaf tissue harvested from individual soybean plants containing Soybean Event pDAB8264.42.32.1. In addition, gDNA was isolated from a conventional soybean plant, Maverick, which contains the genetic background that is representative of the substance line, absent the aad-12 v1 and 2mEPSPS v1 genes. Individual genomic DNA was extracted from lyophilized leaf tissue following the standard CTAB method (Sambrook et al (1989)). Following extraction, the DNA was quantified with a spectrofluorometer using PICO GREEN reagent (Invitrogen, Carlsbad, Calif.). The DNA was then visualized on an agarose gel to confirm the concentrations from the PICO GREEN analysis and to determine the DNA quality.

Example 4.2

DNA Digestion and Separation

For Southern blot molecular characterization of Soybean Event pDAB8264.42.32.1, ten micrograms (10 μg) of genomic DNA was digested. Genomic DNA from the soybean pDAB8264.42.32.1 and non-transgenic soybean line Maverick was digested by adding approximately five units of selected restriction enzyme per μg of DNA and the corresponding reaction buffer to each DNA sample. Each sample was incubated at approximately 37° C. overnight. The restriction enzymes HindIII, NcoI, NsiI and PacI were used individually for the digests (New England Biolabs, Ipswich, Mass.). In addition, a positive hybridization control sample was prepared by combining plasmid DNA, pDAB8264, with genomic DNA from the non-transgenic soybean variety, Maverick. The plasmid DNA/genomic DNA cocktail was digested using the same procedures and restriction enzyme as the test samples. After the digestions were incubated overnight, 25 μL QUIK-PRECIP PLUS solution (EdgeBiosystems, Gaithersburg, Md.) was added and the digested DNA samples were precipitated with isopropanol. The precipitated DNA pellet was resuspended in 15 μL of 1× loading buffer (0.01% bromophenol blue, 10.0 mM EDTA, 10.0% glycerol, 1.0 mM Tris pH 7.5). The DNA samples and molecular size markers were then electrophoresed through 0.85% agarose gels with 0.4×TAE buffer at 35 volts for approximately 18-22 hours to achieve fragment separation. The gels were stained with ethidium bromide and the DNA was visualized under ultraviolet (UV) light.

Example 4.3

Southern Transfer and Membrane Treatment

Southern blot analysis was performed essentially as described by Memelink, et al. (1994). Briefly, following electrophoretic separation and visualization of the DNA fragments, the gels were depurinated with 0.25M HCl for approximately 20 minutes, and then exposed to a denaturing solution (0.4 M NaOH, 1.5 M NaCl) for approximately 30 minutes followed by neutralizing solution (1.5 M NaCl, 0.5 M Tris pH 7.5) for at least 30 minutes. Southern transfer was performed overnight onto nylon membranes using a wicking system with 10×SSC. After transfer the DNA was bound to the membrane by UV crosslinking following by briefly washing membrane with a 2×SSC solution. This process produced Southern blot membranes ready for hybridization.

Example 4.4

DNA Probe Labeling and Hybridization

The DNA fragments bound to the nylon membrane were detected using a labeled probe. Probes were generated by a PCR-based incorporation of a digoxigenin (DIG) labeled nucleotide, [DIG-11]-dUTP, into the DNA fragment amplified from plasmid pDAB8264 using primers specific to gene elements (Table 6). Generation of DNA probes by PCR synthesis was carried out using a PCR DIG PROBE SYNTHESIS KIT (Roche Diagnostics, Indianapolis, Ind.) following the manufacturer's recommended procedures.

Labeled probes were analyzed by agarose gel electrophoresis to determine their quality and quantity. A desired amount of labeled probe was then used for hybridization to the target DNA on the nylon membranes for detection of the specific fragments using the procedures essentially as described for DIG EASY HYB Solution (Roche Diagnostics, Indianapolis, Ind.). Briefly, nylon membrane blots containing fixed DNA were briefly washed with 2×SSC and pre-hybridized with 20-25 mL of pre-warmed DIG EASY HYB solution in hybridization bottles at approximately 45-55° C. for about 2 hours in a hybridization oven. The pre-hybridization solution was then decanted and replaced with ~15 mL of pre-warmed DIG EASY HYB solution containing a desired amount of specific probes denatured by boiling in a water bath for approximately five minutes. The hybridization step was then conducted at approximately 45-55° C. overnight in the hybridization oven.

At the end of the probe hybridization, DIG EASY HYB solutions containing the probes were decanted into clean tubes and stored at approximately −20° C. These probes could be reused twice according to the manufacturer's recommended procedure. The membrane blots were rinsed briefly and washed twice in clean plastic containers with low stringency wash buffer (2×SSC, 0.1% SDS) for approximately five minutes at room temperature, followed by washing twice with high stringency wash buffer (0.1×SSC, 0.1% SDS) for 15 minutes each at approximately 65° C. The membrane blots briefly washed with 1× Maleic acid buffer from the DIG WASH AND BLOCK BUFFER SET (Roche Diagnostics, Indianapolis, Ind.) for approximately 5 minutes. This was followed by blocking in a 1× blocking buffer for 2 hours and an incubation with anti-DIG-AP (alkaline phosphatase) antibody (Roche Diagnostics, Indianapolis, Ind.) in 1× blocking buffer also for a minimum of 30 minutes. After 2-3 washes with 1× washing buffer, specific DNA probes remain bound to the membrane blots and DIG-labeled DNA standards were visualized using CDP-STAR CHEMILUMINESCENT NUCLEIC ACID DETECTION SYSTEM (Roche Diagnostics, Indianapolis, Ind.) following the manufacturer's recommendation. Blots were exposed to chemiluminescent film for one or more time points to detect hybridizing fragments and to visualize molecular size standards. Films were developed with an ALL-PRO 100 PLUS film developer (Konica Minolta, Osaka, Japan) and images were scanned. The number and sizes of detected bands were documented for each probe. DIG-labeled DNA MOLECULAR WEIGHT MARKER II (DIG MWM II) and DIG-labeled DNA MOLECULAR WEIGHT MARKER VII (DIG MWM VII), visible after DIG detection as described, were used to determine hybridizing fragment size on the Southern blots.

TABLE 6

Location and length of probes used in Southern analysis.

| Probe Name | Genetic Element | Length (bp) |
|---|---|---|
| 2mEPSPS | 2mEPSPS v1 | 1238 |
| aad-12 | aad-12 v1 | 671 |
| specR | Spectinomycin resistance gene | 750 |
| OriRep | Ori Rep | 852 |
| trfA | Replication initiation protein trfA | 1119 |

Example 4.5

Southern Blot Results

Expected and observed fragment sizes with a particular digest and probe, based on the known restriction enzyme sites of the aad-12 v1 and 2mEPSPS v1 PTU, are given in Table 7. Two types of fragments were identified from these digests and hybridizations: internal fragments where known enzyme sites flank the probe region and are completely contained within the insertion region of the aad-12 v1 and 2mEPSPS v1 PTU, and border fragments where a known enzyme site is located at one end of the probe region and a second site is expected in the soybean genome. Border fragment sizes vary by event because, in most cases, DNA fragment integration sites are unique for each event. The border fragments provide a means to locate a restriction enzyme site relative to the integrated DNA and to evaluate the number of DNA insertions. Southern blot analyses completed on multiple generations of Soybean Event pDAB8264.42.32.1 produced data which suggested that a low copy, intact aad-12 v1 and 2mEPSPS v1 PTU from plasmid pDAB8264 was inserted into the soybean genome of Soybean Event pDAB8264.42.32.1.

TABLE 7

Predicted and observed hybridizing fragments in Southern blot analysis.

| DNA Probe | Restriction Enzymes | Samples | Expected Fragment Sizes (bp)[1] | Observed Fragment Size (bp)[2] |
|---|---|---|---|---|
| aad-12 | Hind III | pDAB8264 | 4731 | 4700 |
| | | Maverick | none | none |
| | | Soybean Event pDAB8264.42.32.1 | >4078 | 4100 |
| | Nco I | pDAB8264 | 7429 | 7400 |
| | | Maverick | none | none |
| | | Soybean Event pDAB8264.42.32.1 | >3690 | 6700 |
| | Nsi I | pDAB8264 | 4974 | 4900 |
| | | Maverick | none | none |
| | | Soybean Event pDAB8264.42.32.1 | 4974 | 4900 |
| 2mEPSPS | Hind III | pDAB8264 | 9322 | 9300 |
| | | Maverick | none | none |
| | | Soybean Event pDAB8264.42.32.1 | >4260 | 5300 |
| | Nco I | pDAB8264 | 5203 | 5200 |
| | | Maverick | none | none |
| | | Soybean Event pDAB8264.42.32.1 | >3749 | 18000 |

TABLE 7-continued

Predicted and observed hybridizing fragments
in Southern blot analysis.

| DNA Probe | Restriction Enzymes | Samples | Expected Fragment Sizes (bp)[1] | Observed Fragment Size (bp)[2] |
|---|---|---|---|---|
|  | Nsi I | pDAB8264 | 11044 | 11000 |
|  |  | Maverick | none | none |
|  |  | Soybean Event pDAB8264.42.32.1 | >5199 | 7500 |
|  | Pac I | pDAB8264 | 6768 | 6700 |
|  |  | Maverick | none | none |
|  |  | Soybean Event pDAB8264.42.32.1 | 6768 | 6700 |
| SpecR | Hind III | pDAB8264 | 9322 | 9300 |
|  |  | Maverick | none | none |
|  |  | Soybean Event pDAB8264.42.32.1 | none | none |
|  | Nco I | pDAB8264 | 5203 | 5200 |
|  |  | Maverick | none | none |
|  |  | Soybean Event pDAB8264.42.32.1 | none | none |
| OriRep | Nco I | pDAB8264 | 7429 | 7400 |
|  |  | Maverick | none | none |
|  |  | Soybean Event pDAB8264.42.32.1 | none | none |
| trfA | Hind III | pDAB8264 | 9322 | 9300 |
|  |  | Maverick | none | none |
|  |  | Soybean Event pDAB8264.42.32.1 | none | none |

[1]Expected fragment sizes are based on the plasmid map of pDAB8264.
[2]Observed fragment sizes are considered approximately from these analyses and are based on the indicated sizes of the DIG-labeled DNA Molecular Weight Marker II and Mark VII fragments.

The restriction enzymes HindIII and NcoI bind and cleave unique restriction sites in plasmid pDAB8264. Subsequently, these enzymes were selected to characterize the aad-12 v1 gene insert in Soybean Event pDAB8264.42.32.1. Border fragments of >4078 bp or >3690 bp were predicted to hybridize with the probe following HindIII or NcoI digestions, respectively (Table 7). Single aad-12 v1 hybridization bands of ~4100 bp and ~6700 were observed when Hind III or NcoI were used, respectively. The hybridization of the probe to bands of those sizes suggests the presence of a single site of insertion for the aad-12 v1 gene in the genome of Soybean Event pDAB8264.42.32.1. Restriction enzyme NsiI was selected to release a fragment which contains the aad-12 v1 plant transcription unit (PTU; promoter/gene/terminator) (Table 7). The predicted ~4900 bp fragment was observed with the probe following NsiI digestion. Results obtained with the enzyme digestion of the pDAB8264.42.32.1 samples followed by probe hybridization indicated that an intact aad-12 v1 PTU from plasmid pDAB8264 was inserted into the genome of Soybean Event pDAB8264.42.32.1.

The restriction enzymes HindIII NcoI and NsiI bind and cleave restriction sites in plasmid pDAB8264. Subsequently, these enzymes were selected to characterize the 2mEPSPS v1 gene insert in Soybean Event pDAB8264.42.32.1. Border fragments of >4260 bp, >3749 or >5199 bp were predicted to hybridize with the probe following the HindIII NcoI and NsiI digests, respectively (Table 7). Single 2mEPSPS v1 hybridization bands of ~5300 bp, 18000 and ~7500 bp were observed when HindIII NcoI and NsiI were used, respectively. The hybridization of the probe to bands of this size suggests the presence of a single site of insertion for the 2mEPSPS v1 gene in the genome of Soybean Event pDAB8264.42.32.1. Restriction enzyme PacI was selected to release a fragment which contains the 2mEPSPS v1 plant transcription unit (PTU; promoter/gene/terminator) (Table 7). The predicted ~6700 bp fragments were observed with the probe following the PacI digestions. Results obtained with the enzyme digestion of the Soybean Event pDAB8264.42.32.1 samples followed by probe hybridization indicated that an intact 2mEPSPS v1 PTU from plasmid pDAB8264 was inserted into the soybean genome of Soybean Event pDAB8264.42.32.1.

Example 4.6

Absence of Backbone Sequences

Southern blot analysis was also conducted to verify the absence of the spectinomycin resistance gene (specR), On Rep element and replication initiation protein trfA (trf A element) in Soybean Event pDAB8264.42.32.1. No specific hybridization to spectinomycin resistance, Ori Rep element or trf A element is expected in soybean event pDAB8264.42.32.1 samples when appropriate positive (pDAB8264 plasmid DNA added to Maverick genomic DNA) and negative (Maverick genomic DNA) controls are included for Southern analysis. Following HindIII or NcoI digestion and hybridization with the specR specific probe, one expected size band of ~9300 bp or ~5200 bp was observed in the positive control sample (pDAB8264 added to Maverick genomic DNA), respectively. The specR probe did not hybridize to samples of the negative control and Soybean Event pDAB8264.42.32.1. Similarly, one expected size band of ~7400 bp was detected in the positive control sample (pDAB8264 added to Maverick genomic DNA) but absent from the samples of the negative control and Soybean Event pDAB8264.42.32.1 after NcoI digestion and hybridization with the OriRep specific probe. In addition, only one expected size band of ~9,300 bp was detected in the positive control sample (pDAB8264 added to Maverick genomic DNA) but absent from the samples of the negative control and Soybean Event pDAB8264.42.32.1 after HindIII digestion and hybridization with the trfA specific probe. These data indicate the absence of the spectinomycin resistance gene, On Rep element and replication initiation protein trfA in Soybean Event pDAB8264.83.2.1.

Example 5

Agronomic and Yield Field Trial and Herbicide Tolerance

Replicated agronomic trials were run to assess the agronomic characteristics of Soybean Event pDAB8264.42.32.1. The majority of the field trials were planted at distinct geographical locations throughout the United States where the soybean variety which contains Soybean Event pDAB8264.42.32.1 is cultivated. Three sets of experiments were completed. The first series of experiments compared the agronomic efficacy Soybean Event pDAB8264.42.32.1 plants sprayed with the herbicides 2,4-D and glyphosate as compared to Soybean Event pDAB8264.42.32.1 plants that were not sprayed with herbicides. The second series of experiments compared the agronomic efficacy of Soybean Event pDAB8264.42.32.1 plants with the near isoline Maverick control plants. Finally, a third series of experiments were complete to test the tolerance of Soybean Event pDAB8264.42.32.1 plants to applications of glufosinate.

The first experiments compared Soybean Event pDAB8264.42.32.1 plants that were sprayed with 2,4-D dimethylamine salt at 1120 g ae/ha (Weedar 64, Nufarm, Burr Ridge, Ill.) and glyphosate at 1120 g ae/ha (Durango, Dow AgroSciences, Indianapolis, Ind.), to Soybean Event pDAB8264.42.32.1 plants that were not sprayed. Herbicide treatments were applied at the V3 and R2 growth stages. The field trial, consisting of sprayed and un-sprayed sections, were set up as a randomized complete block designs for two separate growing years. The 2010 field trial consisted of two replications per twenty five entries in each block, and the 2011 field trial consisted of four replications per twenty six entries in each block. For both experiments, each plot consisted of two rows, 12.5 feet long, planted 30 inches apart with a 2.5 foot alley between plots. Throughout the season, field plots were maintained under normal agronomic practices and kept free from weeds. Throughout the season a number of agronomic characteristics were measured. These characteristics and the growth stage when the data were collected are listed in Table 8.

TABLE 8

List of agronomic characteristics measured in field trials to compare Soybean Even pDAB8264.42.32.1 with Maverick.

| Agronomic characteristic or trait measured | Growth stage when measurement taken |
|---|---|
| Emergence: Stand count divided by the number of seeds planted in a one meter section multiplied by 100. | Calculated based on early stand count |
| Seedling vigor: Percent vigor with 0% representing a plot with all dead plants and 100% representing plots that look very healthy. | V1-V3 |
| Days to Flowering: Days from planting when 50% of the plants in the plot began to flower. | R1 |
| Stand count at R2: Number of plants in a representative one meter section of row at the R2 growth stage. | R2 |
| Disease incidence: Severity of disease in the plot rated on a scale of 0-100%. | R6 |
| Insect damage: Percentage of plant tissue in the plot damaged by insects. | R6 |
| Plant height: Average height in centimeters of the plants in each plot measured from the soil surface to the tip after leaves have fallen. | R8 |
| Lodging: Percent lodging at harvest time with 0% = no lodging and 100% = all plants in a plot flat on the ground. | R8 |
| Days to maturity: Days from planting when 95% of the pods in a plot reached their dry down color. | R8 |
| Shattering: Percentage of pods shattered per plot. | R8 |
| Yield: Bushels per acre adjusting to 13% moisture. | R8 |
| 100 seed weight: For each plot count out 100 seeds and record the weight in grams. | R8 |
| Seed Pigmentation: Rate the amount of light brown pigmentation on a scale of 1 to 5 | 1 = no light brown pigmentation to 5 = severe brown pigmentation. |
| Application 1 Injury 1 daa (%): Rate overall visual crop injury, chlorosis and necrosis at 6 to 24 hours after V3 chemical application. Look for any signs of epinasty which is typical of 2,4-D injury. This is exhibited as twisting or drooping of leaves and stems. | 0 to 100% SCALE (0 = no injury, 100 = complete plant death). |
| Application 1 Injury 7 daa (%): Rate overall visual crop injury, chlorosis and necrosis at 7 days after V3 chemical application. | 0 to 100% SCALE (0 = no injury, 100 = complete plant death). |
| Application 1 Injury 14 daa (%): Rate overall visual crop injury, chlorosis and necrosis at 14 days after V3 chemical application. | 0 to 100% SCALE (0 = no injury, 100 = complete plant death). |
| Application 2 Injury 1 daa (%): Rate overall visual crop injury, chlorosis and necrosis at 6 to 24 hours after R2 chemical application. Look for any signs of epinasty which is typical of 2,4-D injury. This is exhibited as twisting or drooping of leaves and stems. | 0 to 100% SCALE (0 = no injury, 100 = complete plant death). |

TABLE 8-continued

List of agronomic characteristics measured in field trials to compare Soybean Even pDAB8264.42.32.1 with Maverick.

| Agronomic characteristic or trait measured | Growth stage when measurement taken |
|---|---|
| Application 1 Injury 7 daa (%): Rate overall visual crop injury, chlorosis and necrosis at 7 days after R2 chemical application. | 0 to 100% SCALE (0 = no injury, 100 = complete plant death). |
| Application 1 Injury 14 daa (%): Rate overall visual crop injury, chlorosis and necrosis at 14 days after R2 chemical application. | 0 to 100% SCALE (0 = no injury, 100 = complete plant death). |

At the end of the growing season, data from all locations were combined and an across location analysis was performed. Data analysis was carried out and least square means from the analysis are reported for the different crop characteristics in Table 9. For variables where a significant entry effect was measured a subsequent mean separation was performed using Student's T test to make the comparison between sprayed and unsprayed Soybean Event pDAB8264.42.32.1 plants. The probability level for determining significance was set at p=0.05. Soybean Event pDAB8264.42.32.1 showed tolerance to the 2,4-D and glyphosate tank mix. In contrast, none of the Maverick plants that were sprayed with the 2,4-D and glyphosate tank mix were tolerant to the herbicide treatments.

TABLE 9

Least square means from the across location analysis comparing Soybean Event pDAB8264.42.32.1 sprayed plants to unsprayed plants over the years of 2010 and 2011. For each trait, values not followed by the same letter are different according to the Student's T test.

| Agronomic Characteristic or Trait | Soybean Event pDAB8264.42.32.1 | | | |
|---|---|---|---|---|
| | Sprayed | | Non-sprayed | |
| Emergence (%) | 70.3 | A | 71.4 | A |
| Vigor V1-V3 (%) | 48.0 | A | 48.8 | A |
| Application 1 Injury 1 daa (%) | 1.6 | A | 0.0 | B |
| Application 1 Injury 7 daa (%) | 1.0 | A | 0.0 | B |
| Application 1 Injury 14 daa (%) | 0.0 | A | 0.0 | A |
| Days to flower (days from planting) | 40.1 | A | 39.8 | A |
| Stand count R2 | 20.1 | A | 20.7 | A |
| Application 2 Injury 1 daa (%) | 3.4 | A | 0.1 | B |
| Application 2 Injury 7 daa (%) | 2.3 | A | 0.0 | B |
| Application 2 Injury 14 daa (%) | 1.3 | A | 0.1 | A |
| Disease incidence (%) | 7.9 | A | 3.4 | B |
| Insect damage (%) | 10.1 | A | 8.7 | A |
| Height (cm) | 111.1 | A | 108.2 | A |
| Maturity (days from planting) | 115.9 | A | 115.1 | A |
| Lodging (%) | 15.2 | A | 12.8 | A |
| Shattering (%) | 0.4 | A | 0.1 | A |
| Yield (bu/acre) | 44.6 | A | 42.9 | A |
| 100 seed weight (g) | 12.4 | A | 11.9 | B |
| Seed pigmentation (1 (none) to 5 (severe) | 2.1 | A | 1.9 | A |

Soybean Event pDAB8264.42.32.1 provided robust tolerance to the tank mix applications of glyphosate and 2,4-D at both the V3 and R2 stages of growth development. Although there was a slight injury when the herbicides were initially applied, the plants were not significantly injured and grew-out of the injury response by 14 days after application. All traits measured with the exception of 100 seed weight and disease incidence exhibited parity between Soybean Event pDAB8264.42.32.1 plants treated with herbicides and Soybean Event pDAB8264.42.32.1 plants that were not treated with herbicides. As such, the application of field rates of 2,4-D and glyphosate to Soybean Event pDAB8264.42.32.1 plants does not result in any meaningful change of agronomic characteristics or traits that would be deleterious to the agronomic performance of Soybean Event pDAB8264.42.32.1 plants.

The second experiments compared the agronomic performance for select agronomic characteristics between Soybean Event pDAB8264.42.32.1 and near isoline Maverick control plants. The field trials were set up as a randomized complete block designs for two separate growing years. The 2010 field trial consisted of two replications per twenty five entries in each block, and the 2011 field trial consisted of four replications per twenty six entries in each block. For both experiments, each plot consisted of two rows, 12.5 feet long, planted 30 inches apart with a 2.5 foot alley between plots. Throughout the season, field plots were maintained under normal agronomic practices and kept free from weeds. Throughout the season a number of agronomic characteristics were measured. These characteristics and the growth stage when the data were collected are listed in Table 8.

At the end of the growing season, data from all locations were combined and an across location analysis was performed. Data analysis was carried out and least square means from the analysis are reported for the different crop characteristics in Table 10. For variables where a significant entry effect was measured a subsequent mean separation was performed using Student's T test to make the comparison between Maverick and Soybean Event pDAB8264.42.32.1. The probability level for determining significance was set at p=0.05.

TABLE 10

Least square means from the across location analysis comparing Soybean Event pDAB8264.42.32.1 plants with Maverick plants over the years of 2010 and 2011. For each trait, values not followed by the same letter are different according to the Student's T test.

| Agronomic Characteristics or Traits | Maverick | | Soybean Event pDAB8264.42.32.1 | |
|---|---|---|---|---|
| Emergence (%) | 72.5 | A | 72.2 | A |
| Vigor V1 (1 poor-9 good) | 48.2 | A | 49.2 | A |
| Days to flower (days from planting) | 42.3 | A | 42.1 | A |
| Stand R1 | 19.6 | A | 20.8 | A |
| Disease incidence (%) | 6.4 | A | 7.0 | A |
| Insect damage (%) | 12.8 | A | 12.9 | A |
| Height (cm) | 114.6 | A | 112.5 | A |
| Maturity (days from planting) | 119.7 | A | 119.0 | A |
| Lodging (%) | 15.8 | A | 14.0 | A |
| Shattering | 0.1 | A | 0.4 | A |
| Yield (bu/acre) | 47.2 | A | 45.7 | A |
| 100 seed weight | 13.0 | A | 12.6 | A |
| Seed pigmentation (1 (none) to 5 (severe)) | 1.3 | B | 1.8 | A |

All traits measured with the exception of seed pigmentation exhibited parity between Soybean Event pDAB8264.42.32.1 and Maverick. Soybean Event pDAB8264.42.32.1 plants resulted in a seed pigmentation rating of 1.8 as compared to the Maverick plants which resulted in a seed pigmentation rating of 1.3. This difference is not a severe difference for producers, and does not impair crop performance, nor would this difference result in a meaningful agronomic difference which would impair crop performance. The results indicate that Soybean Event pDAB8264.42.32.1 may develop differently than Maverick for some agronomic characteristics, but the difference is minimal and not outside the normal range of commercially grown soybeans.

To test the glufosinate herbicide tolerance of Soybean Event pDAB8264.42.32.1 the event was planted in an efficacy trial in Indiana for the 2010 growing season. The cultivar Maverick, which was originally transformed to produce soybean event pDAB9582.816.15.1, was planted in each nursery and included as a control in the experiments. The event was randomized with other events that were at the same stage of testing and consisted of four replications. Maverick was included as the non-transformed control. The trial was set up as a modified split-plot design with treatments as whole plots and events as subplots. A glufosinate treatment applied at 822 g ae/ha and a non-sprayed control treatment were applied to the soybean plants. Treatments were applied at the V5 and R2 growth stages. Herbicide tolerance was measured by assessing plants for injury at 6 hours and 7 days following treatment. Injury was assessed by visually looking for chlorosis, leaf necrosis and plant death. Soybean Event pDAB8264.42.32.1 exhibited robust tolerance to the glufosinate herbicide application. In contrast, none of the Maverick plants were tolerant to the herbicide treatments.

Example 6

Event Specific TaqMan Assay

Figure 4:
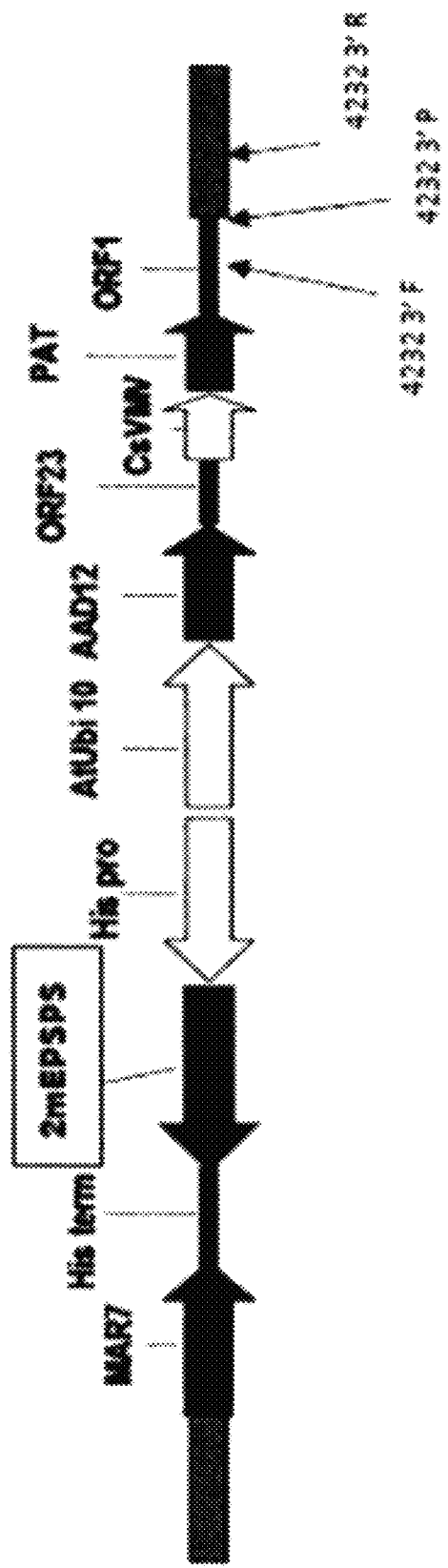
FIG. 4: is a schematic diagram depicting primer locations for the TAQMAN assay detection of soybean Event pDAB8264.42.32.1.

An event specific TAQMAN assay was developed to detect the presence of Soybean Event pDAB8264.42.32.1 and to determine zygosity status of plants in breeding populations. Soybean Event pDAB8264.42.32.1 contains the T-strand of the binary vector pDAB8264 (FIG. 4). For specific detection of Soybean Event pDAB8264.42.32.1, specific TAQMAN primers and probes were designed according to the DNA sequences located in the 5' (SEQ ID NO:19) or 3' (SEQ ID NO:20) insert-to-plant junction (FIG. 4). One event specific assay for Soybean Event pDAB8264.42.32.1 was designed to specifically detect a 131 bp DNA fragment that spans the 3' integration junction using two primers and a target-specific MGB probe synthesized by Applied Biosystems (ABI) containing the FAM reporter at its 5' end. Specificity of this TAQMAN detection method for Soybean Event pDAB8264.42.32.1 was tested against 11 different events which contain the 2mEPSPS v1 and aad-12 v1 PTUs and a control non-transgenic soybean variety (Maverick) in duplex format with the soybean specific endogenous reference gene, GMFL01-25-J19 (*Glycine max* cDNA, GenBank: AK286292.1).

Example 6.1 gDNA Isolation

Genomic DNA (gDNA) samples of 11 different soybean events and non-transgenic soybean varieties were tested in this study. Genomic DNA was extracted using modified Qiagen MAGATTRACT PLANT DNA kit (Qiagen, Valencia, Calif.). Fresh soybean leaf discs, 8 per sample, were used for gDNA extraction. Samples were diluted with DNase-free water resulting in a concentration of approximately 10 ng/μL for the purpose of this study.

Example 6.2

TaqMan Assay and Results

Specific TAQMAN primers and probe were designed for a Soybean Event pDAB8264.42.32.1 specific TAQMAN assay. These reagents can be used with the conditions listed below to detect the Soybean Event pDAB8264.42.32.1. Table 11 lists the primer and probe sequences that were developed specifically for the detection of Soybean Event pDAB8264.42.32.1.

TABLE 11

TAQMAN PCR primers and probes.

Event Target Reaction

| Name | Description | Sequence |
|---|---|---|
| SEQ ID NO: 12 | 4232_3'F Event specific forward Primer | CGCAATGTGTTATTAAGTTGTCTAAGC |
| SEQ ID NO: 13 | 4232_3'R Event specific reverse Primer | CTCTATCGGTTTAATTGGGATCCTAT |
| SEQ ID NO: 14 | 4232_3'P Event specific probe used with 4232_3'F and 4232_3'R | 5'FAM/ATGCCAATTACCAACAAT-MGB |

Reference Target Reaction

| Name | Description | Sequence |
|---|---|---|
| SEQ ID NO: 15 | GMS116 F Forward Primer | GTAATATGGGCTCAGAGGAATGGT |
| SEQ ID NO: 16 | GMS116 R Reverse Primer | ATGGAGAAGAACATTGGAATTGC |
| SEQ ID NO: 17 | GMS116 Probe | 5'HEX/CCATGGCCCGGTACCATCTGGTC/3BHQ_1/3' |

The multiplex PCR conditions for amplification are as follows: 1× Roche PCR Buffer, 0.4 µM event specific forward primer, 0.4 µM event specific reverse primer, 0.4 µM Primer GMS116 F, 0.4 µM Primer GMS116 R, 0.2 µM Event specific probe, 0.2 µM GMS116 Probe, 0.1% PVP, 6-20 ng gDNA in a total reaction of 10 µL. The cocktail was amplified using the following conditions: i) 95° C. for 10 min., ii) 95° C. for 10 sec, iii) 60° C. for 40 sec, iv) repeat step ii-iii for 40 cycles, v) 40° C. hold. The Real time PCR was carried out on the ROCHE LIGHTCYCLER 480. Data analysis was based on measurement of the crossing point (Cp value) determined by LIGHTCYCLER 480 software, which is the PCR cycle number in which the rate of change in fluorescence reaches its maximum.

The TAQMAN detection method for Soybean Event pDAB8264.42.32.1 was tested against 11 different events which contain the 2mEPSPS v1 and aad-12 v1 PTUs and a non-transgenic soybean variety in duplex format with soybean specific endogenous reference gene, GMFL01-25-J19 (GenBank: AK286292.1). The assay specifically detected the Soybean Event pDAB8264.42.32.1 and did not produce or amplify any false-positive results from the controls (i.e. the 11 different events which contain the 2mEPSPS v1 and aad-12 v1 PTUs and a non-transgenic soybean variety). The event specific primers and probes can be used for the detection of the Soybean Event pDAB8264.42.32.1 and these conditions and reagents are applicable for zygosity assays.

Example 7

Expected Sequence of Soybean Event pDAB8264.42.32.1

SEQ ID NO:18 provides the expected sequence of soybean event pDAB8264.42.32.1. This sequence contains the 5' genomic flanking sequence, the expected T-strand insert of pDAB8264 and 3' genomic flanking sequences. With respect to SEQ ID NO:18, residues 1-1246 are 5' genomic flanking sequence, residues 1247-11507 are residues of the pDAB8264 T-strand insert, and residues 11508-12011 are 3' genomic flanking sequence. The junction sequence or transition with respect to the 5' end of the insert thus occurs at residues 1246-1247 of SEQ ID NO:18. The junction sequence or transition with respect to the 3' end of the insert thus occurs at residues 11507-11508 of SEQ ID NO:18.

It should be noted that SEQ ID NO:18 is the expected representation of Soybean Event pDAB8264.42.32.1 and was assembled from an alignment of SEQ ID NO:19, SEQ ID NO:20, and the t-strand of pDAB8264. The actual sequence of the T-strand insert of Soybean Event pDAB8264.42.32.1 may slightly deviate from SEQ ID NO:18 (e.g., residues 1247-11507). During the transformation process of introducing an T-stand insert into the genome of plant cells, it is not uncommon for some deletions or other alterations of the insert to occur. Moreover, errors in PCR amplification can occur which might result in minor sequencing errors. For example, flanking sequences listed herein were determined by generating amplicons from soybean genomic DNAs, and then cloning and sequencing the amplicons. It is not unusual to find slight differences and minor discrepancies in sequences generated and determined in this manner, given the many rounds of amplification that are necessary to generate enough amplicon for sequencing from genomic DNAs. One skilled in the art should recognize and be put on notice that any adjustments needed due to these types of common sequencing errors or discrepancies are within the scope of the subject invention. Thus, the relevant segment of the plasmid sequence provided herein might comprise some minor variations. Thus, a plant comprising a polynucleotide having some range of identity with the subject insert sequence is within the scope of the subject invention. Identity to the sequence of SEQ ID NO:18, or any segment thereof as discussed herein, can be a polynucleotide sequence having at least 90%, 91%, 92%, 93%, 94%, 95%, 96%, 97%, 98%, 99%, or greater sequence identity with a sequence exemplified or described herein. The sequence of the flanking sequences plus insert sequence can be confirmed with reference to the deposited seed. Thus, some differences between SEQ ID NO:18 and the actual T-strand insert of Soybean Event pDAB8264.42.32.1 may be identified and are within the scope of the present invention.

Example 8

Use of Soybean Event pDAB8264.42.32.1 Insertion Site for Targeted Integration

Consistent agronomic performance of the transgene of Soybean Event pDAB8264.42.32.1 over several generations under field conditions suggests that these identified regions around the Soybean Event pDAB8264.42.32.1 insertion site on chromosome 15 provide good genomic locations for the targeted integration of other transgenic genes of interest. Such targeted integration overcomes the problems with so-called "position effect," and the risk of creating a mutation in the genome upon integration of the transgene into the host. Further advantages of such targeted integration include, but are not limited to, reducing the large number of transformation events that must be screened and tested before obtaining a transgenic plant that exhibits the desired level of transgene expression without also exhibiting abnormalities resulting from the inadvertent insertion of the transgene into an important locus in the host genome. Moreover, such targeted integration allows for stacking transgenes rendering the breeding of elite plant lines with both genes more efficient.

Using the disclosed teaching, a skilled person is able to target polynucleic acids of interest to the same insertion site as that in Soybean Event pDAB8264.42.32.1 or to a site in close proximity to the insertion site in Soybean Event pDAB8264.42.32.1. One such method is disclosed in International Patent Application No. W02008/021207, herein incorporated by reference in its entirety.

Briefly, up to 20 Kb of the genomic sequence flanking 5' to the insertion site and up to 20 Kb of the genomic sequence flanking 3' to the insertion site SEQ ID NO:18 are used to flank the gene or genes of interest that are intended to be inserted into a genomic of Soybean Event pDAB8264.42.32.1 via homologous recombination. The gene or genes of interest can be placed exactly as in the Soybean Event pDAB8264.42.32.1 insertion site or can be placed anywhere within the 20 Kb regions around the Soybean Event pDAB8264.42.32.1 insertion sites to confer consistent level of transgene expression without detrimental effects on the plant. The DNA vectors containing the gene or genes of interest and flanking sequences can be delivered into plant cells via one of the several methods known to those skilled in the art, including but not limited to *Agrobacterium*-mediated transformation. The insertion of the donor DNA vector into the Soybean Event pDAB8264.42.32.1 target site can be further enhanced by one of the several methods, including but not limited to the co-expression or up-regulation of recombination enhancing genes or down-regulation of endogenous recombination suppression genes.

Furthermore, it is known in the art that double stranded cleavage of specific sequences in the genome can be used to increase homologous recombination frequency, therefore insertion into the Soybean Event pDAB8264.42.32.1 insertion site and its flanking regions can be enhanced by expression of natural or designed sequence-specific endonucleases for cleaving these sequences. Thus, using the teaching provided herein, any heterologous nucleic acid can be inserted at a target site located between or in proximity of SEQ ID NO:1 and SEQ ID NO:2, and in some instances within or in proximity to SEQ ID NO:18.

Example 9

Excision of the pat Gene Expression Cassette from Soybean Event pDAB8264.42.32.1

The removal of a selectable marker gene expression cassette can be advantageous for targeted insertion into Soybean Event pDAB8264.42.32.1. The removal of the pat selectable marker from Soybean Event pDAB8264.42.32.1 allows for the re-use of the pat selectable marker in targeted integration of polynucleic acids within the genomic location of Soybean Event pDAB8264.42.32.1 in subsequent generations of soybean.

Using the disclosed teaching, a skilled person is able to excise polynucleic acids of interest from Soybean Event pDAB8264.42.32.1. One such method is disclosed in U.S. patent filing Ser. No. 13/011,666, herein incorporated by reference in its entirety.

Briefly, sequence-specific endonucleases such as zinc finger nucleases are designed which recognize, bind and cleave specific DNA sequences that flank a gene expression cassette. The zinc finger nucleases are delivered into the plant cell by crossing a parent plant which contains transgenic zinc finger nuclease expression cassettes to a second parent plant which contains Soybean Event pDAB8264.42.32.1. The resulting progeny are grown to maturity and analyzed for the loss of the pat expression cassette via leaf painting with a herbicide which contains glufosinate. Progeny plants which are not resistant to the herbicide are confirmed molecularly and advanced for self-fertilization. The excision and removal of the pat expression cassette is molecularly confirmed in the progeny obtained from the self-fertilization. Using the teaching provided herein, any heterologous nucleic acid can be excised from soybean chromosome 15 at a target site located between SEQ ID NO:1 and SEQ ID NO:2, preferably within SEQ ID NO:18.

The invention claimed is:

1. A transgenic soybean plant comprising a polynucleotide segment having SEQ ID NO:18 in its genome.

2. A soybean seed comprising a genome comprising Event pDAB8264.42.32.1 as present in representative seed deposited with American Type Culture Collection (ATCC) under Accession No. PTA-11993.

3. A soybean seed of the plant of claim 1, said seed comprising said polynucleotide segment.

4. A soybean plant produced by growing the seed of claim 3, said plant comprising said polynucleotide segment.

5. A progeny plant of the soybean plant of claim 4, said progeny plant comprising Event pDAB8264.42.32.1.

6. A method of making an expression cassette for a soybean plant, said method comprising producing a heterologous polynucleotide, operably linked to a promoter, and inserting said heterologous polynucleotide operably linked to said promoter into a segment of soybean genomic DNA to produce SEQ ID NO:18.

7. A part of the plant of claim 4, wherein said part is selected from the group consisting of pollen, an ovule, a flower, a shoot, a root, and a leaf, said part comprising said polynucleotide segment.

8. An isolated polynucleotide molecule, wherein said molecule has a sequence having SEQ ID NO:18.

9. An isolated polynucleotide, wherein said polynucleotide comprises a nucleotide sequence selected from the group consisting of SEQ ID NOs:18, 19, 20, and 21.

10. A method of breeding a soybean plant, said method comprising crossing a first soybean plant comprising a transgenic insert in genomic DNA of said first soybean plant, said transgenic insert having a sequence having SEQ ID NO:18, with a second soybean plant to produce a third soybean plant, and assaying said third soybean plant for the presence of said transgenic insert.

11. The method of claim 10, wherein said method is used for introgressing a herbicide tolerance trait into said third soybean plant, wherein said first soybean plant comprises SEQ ID NO:19 and SEQ ID NO:20, and wherein said third soybean plant is assayed for the presence of at least one of SEQ ID NO:19 and SEQ ID NO:20.

12. A method of controlling weeds, said method comprising applying at least one of an aryloxyalkanoate herbicide, a glyphosate herbicide, a bialaphos herbicide, a phosphinothricin herbicide, and a glufosinate herbicide to a field, said field comprising the plant of claim 1.

13. The method of claim 12, wherein said herbicide is applied simultaneously or sequentially.

14. The method of claim 12, wherein said aryloxyalkanoate herbicide is selected from the group consisting of 2,4-D, 2,4-DB, MCPA, and MCPB.

15. The method of claim 14, wherein said method comprises applying at least one additional herbicide to said field.

16. The method of claim 15, wherein said at least one additional herbicide is dicamba.

17. The method of claim 12, wherein said method comprises planting the seed of claim 3 in the field within 14 days of applying the herbicide.

18. The method of claim 12, wherein at least two of said herbicides are applied within the same growing season.

19. The method of claim 12, wherein said at least one herbicide is applied over the top of said plant.

20. A stably transformed dicot plant comprising a polynucleotide having a nucleic acid molecule comprising a sequence selected from the group consisting of SEQ ID NO:18, SEQ ID NO:19, and SEQ ID NO:20.

21. The stably transformed dicot plant of claim 20, wherein the dicot plant is from Glycine max.

22. The soybean plant of claim 1, wherein the soybean plant is resistant to at least one herbicide selected from the group consisting of an aryloxyalkanoate herbicide, a glyphosate herbicide, and a glufosinate herbicide, and wherein said soybean plant comprises residues 1247-11507 of said SEQ ID NO:18.

23. A plant cell comprising a polynucleotide segment having SEQ ID NO:18 in its genome.

24. An isolated polynucleotide having a sequence selected from the group consisting of SEQ ID NO:18, SEQ ID NO:19, SEQ ID NO:20, and the complements thereof.

25. A plant cell comprising Event pDAB8264.42.32.1, wherein said plant cell comprises a first junction sequence having SEQ ID NO:19 and a second junction sequence having SEQ ID NO:20, said expression cassette comprising:
   a. a first plant transcription unit which expresses a 2mepsps gene;
   b. a second plant transcription unit which expresses an aad-12 gene; and
   c. a third plant transcription unit which expresses a patv6 gene.

* * * * *